(12) United States Patent
Hashino et al.

(10) Patent No.: US 10,308,911 B2
(45) Date of Patent: *Jun. 4, 2019

(54) METHODS FOR GENERATING THE INNER EAR AND OTHER CRANIAL PLACODE-DERIVED TISSUES USING PLURIPOTENT STEM CELLS

(71) Applicant: Indiana University Research & Technology Corporation, Indianapolis, IN (US)

(72) Inventors: Eri Hashino, Indianapolis, IN (US); Gerry Oxford, Indianapolis, IN (US); Karl R. Koehler, Indianapolis, IN (US)

(73) Assignee: Indiana University Research & Technology Corporation, Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/446,552

(22) Filed: Mar. 1, 2017

(65) Prior Publication Data
US 2017/0240858 A1  Aug. 24, 2017

Related U.S. Application Data

(63) Continuation of application No. 14/398,664, filed as application No. PCT/US2013/039686 on May 6, 2013, now Pat. No. 9,624,468.

(60) Provisional application No. 61/791,567, filed on Mar. 15, 2013, provisional application No. 61/642,701, filed on May 4, 2012.

(51) Int. Cl.
C12N 5/0793 (2010.01)
C12N 5/071 (2010.01)
G01N 33/50 (2006.01)

(52) U.S. Cl.
CPC ........... *C12N 5/0627* (2013.01); *C12N 5/062* (2013.01); *G01N 33/5044* (2013.01); *G01N 33/5073* (2013.01); *C12N 2501/113* (2013.01); *C12N 2501/115* (2013.01); *C12N 2501/119* (2013.01); *C12N 2501/15* (2013.01); *C12N 2501/155* (2013.01); *C12N 2501/415* (2013.01); *C12N 2501/727* (2013.01); *C12N 2506/02* (2013.01); *C12N 2506/03* (2013.01); *C12N 2533/90* (2013.01)

(58) Field of Classification Search
CPC .............................. C12N 5/0627; C12N 5/06; C12N 2501/113; C12N 2501/119; C12N 2501/415; C12N 2501/727; C12N 2506/02; C12N 2506/03; C12N 2533/90; G01N 33/5044; G01N 33/5073
See application file for complete search history.

(56) References Cited

U.S. PATENT DOCUMENTS

2011/0097799 A1  4/2011  Stankewicz et al.
2014/0004556 A1  1/2014  Heller et al.

FOREIGN PATENT DOCUMENTS

WO   2008094597 A2   8/2008

OTHER PUBLICATIONS

Eiraku et al. "Self-organizing optic-cup morphogenesis in three-dimensional culture."Nature vol. 472, pp. 51-56 (Apr. 7, 2011) (Year: 2011).*
Kwon et al. "Identification of Early Requirements for Preplacodal Ectoderm and Sensory Organ Development."PLoS Genetics, 2010, 6(9):e1001133, pp. 1-14. (Year: 2010).*
Harvey et al. "NResponse to BMP4 signalling during ES cell differentiation defines intermediates of the ectoderm lineage." J Cell Sci 2010 123: 1796-1804 (Year: 2010).*
Zhang et al. "Distinct functions of BMP4 during different stages of mouse ES cell neural commitment."Development. Jul. 2010;137(13):2095-105 (Year: 2010).*
Leung et al. "Differential BMP signaling controls formation and differentiation of multipotent preplacodal ectoderm progenitors from human embryonic stem cells."Dev Biol. Jul. 15, 2013; 379(2): 208-220. (Year: 2013).*
Honda et al. "Generation of induced pluripotent stem cells in rabbits: potential experimental models for human regenerative medicine."J Biol Chem. Oct. 8, 2010;285(41):31362-9 (Year: 2010).*
Hideyuki Kobayashi, Toshihiro Tai, Koichi Nagao and Koichi Nakajima (2014). The Minipig—A New Tool in Stem Cell Research, Pluripotent Stem Cell Biology—Advances in Mechanisms, Methods and Models, Prof. Craig Atwood (Ed.), ISBN: 978-953-51-1590-8, InTech, DOI: 10.5772/57603. (Year: 2014).*
Keefer et al. "Challenges and prospects for the establishment of embryonic stem cell lines of domesticated ungulates." Anim Reprod Sci. Mar. 2007;98(1-2):147-68. (Year: 2007).*
Bermingham-McDonogh, et al., Regulated Reprogramming in the Regeneration of Sensory Receptor Cells, Neuron, 2011, 71:389-405.
Bernardo, et al., BRACHYURY and CDX2 Mediate BMP-Induced Differentiation of Human and Mouse Pluripotent Stem Cells Into Embryonic and Extraembryonic Lineages, Cell Stem Cell, 2011, 9:144-155.
Brigande, et al., Quo Vadis, Hair Cell Regeneration?, Nature Neuroscience, 2009, 12(6):679-685.
Chambers, et al., Highly Efficient Neural Conversion of Human ES and iPS Cells by Dual Inhibition of SMAD Signaling, Nat. Biotechnol., 2009, 27(3):275-280.

(Continued)

*Primary Examiner* — Titilayo Moloye
(74) *Attorney, Agent, or Firm* — Quarles & Brady LLP

(57) ABSTRACT

Disclosed herein are methods and compositions for generating cultures and isolated cell populations containing pre-placodal ectoderms cells, otic placode cells, and inner ear sensory hair cells derived from pluripotent cells by modulating TGFβ, BMP, and FGF signaling pathways under defined culture conditions. Also described are methods for obtaining non-otic placodal tissues from pluripotent stem cells. Methods for identifying agents that induce or enhance differentiation and generation of hair cells are also disclosed. Methods for identifying cytoprotective agents for hair cells are also described.

19 Claims, 27 Drawing Sheets

Specification includes a Sequence Listing.

(56) References Cited

OTHER PUBLICATIONS

Chen, et al., Restoration of Auditory Evoked Responses by Human ES Cell-Derived Otic Progenitors, Nature, 2012, 490(7419):278-282.
Coate, et al., Otic Mesenchyme Cells Regulate Spiral Ganglion Axon Fasciculation Through a Pou3f4/EphA4 Signaling Pathway, Neuron, 2012, 73:49-63.
Desai, et al., Comparative Morphology of Rodent Vestibular Periphery. I. Saccular and Utricular Maculae, J. Neurophysiol., 2005, 93:251-266.
Eiraku, et al., Self-Organized Formation of Polarized Cortical Tissues from ESCs and Its Active Manipulation by Extrinsic Signals, Cell Stem Cell, 2008, 3:519-532.
Gale, et al., FM1-43 Dye Behaves as a Permeant Blocker of the Hair-Cell Mechanotransducer Channel, Journal of Neuroscience, 2001, 21(18):7013-7025.
Geleoc, et al., Developmental Acquisition of Voltage-Dependent Conductances and Sensory Signaling in Hair Cells of the Embryonic Mouse Inner Ear, Journal of Neuroscience, 2004, 24(49):11148-11159.
Grocott, et al., The Peripheral Sensory Nervous System in the Vertebrate Head: A Gene Regulatory Perspective, Developmental Biology, 2012, 370:3-23.
Groves, et al., Shaping Sound in Space: The Regulation of Inner Ear Patterning, Development, 2012, 139:245-257.
Hu, et al., Inner Ear Hair Cells Produced in vitro by a Mesenchymal-to-epithelial Transition, PNAS, 2007, 104 (42):16675-16680.
Kamiya, et al., Intrinsic Transition of Embryonic Stem-Cell Differentiation into Neural Progenitors, Nature, 2011, 470:503-509.
Koehler, et al., Extended Passaging Increases the Efficiency of Neural Differentiation From Induced Pluripotent Stem Cells, BMC Neuroscience, 2011, 12:82, pp. 1-14.
Kondo, et al., Tlx3 Exerts Context-Dependent Transcriptional Regulation and Promotes Neuronal Differentiation from Embryonic Stem Cells, PNAS, 2008, 105(15):5780-5785.
Kopecky, et al., Regeneration of Hair Cells: Making Sense of All the Noise, Pharamaceuticals, 2011, 4:848-879.
Kwon, et al., Mesendodermal Signals Required for Otic Induction: Bmp-Antagonists Cooperate With Fgf and Can Facilitate Formation of Ectopic Otic Tissue, Developmental Dynamics, 2009, 238:1582-1594.
Kwon, et al., Identification of Early Requirements for Preplacodal Ectoderm and Sensory Organ Development, PLoS Genetics, 2010, 6(9):e1001133, pp. 1-14.
Ladher, et al., From Shared Lineage to Distinct Functions: The Development of the Inner Ear and Epibranchial Placodes, Development, 2010, 137:1777-1785.
Laine, et al., Cell Cycle Regulation in the Inner Ear Sensory Epithelia: Role of Cyclin D1 and Cyclin-Dependent Kinase Inhibitors, Developmental Biology, 2010, 337:134-146.
Li, A., et al., Architecture of the Mouse Utricle: Macular Organization and Hair Bundle Heights, J. Neurophysiol., 2008, 99:718-733.
Li, H., et al., Generation of Hair Cells by Stepwise Differentiation of Embryonic Stem Cells, PNAS, 2003, 100(23)13495-13500.
Lysakowski, et al., Molecular Microdomains in a Sensory Terminal, the Vestibular Calyx Ending, Journal of Neuroscience, 2011, 31(27):10101-10114.
Meyers, et al., Lighting up the Senses: FM1-43 Loading of Sensory Cells Through Nonselective Ion Channels, Journal of Neuroscience, 2003, 23(10):4054-4065.
Nakano, et al., Self-Formation of Optic Cups and Storable Stratified Neural Retina from Human ESCs, Cell Stem Cell, 2012, 10:771-785.
Oesterle, et al., Sox2 and Jagged1 Expression in Normal and Drug-Damaged Adult Mouse Inner Ear, JARO, 2008, 9:65-89.
Oshima, et al., Mechanosensitive Hair Cell-Like Cells from Embryonic and Induced Pluripotent Stem Cells, Cell, 2010, 141:704-716.
Ouji, et al., In Vitro Differentiation of Mouse Embryonic Stem Cells Into Inner Ear Hair Cell-Like Cells Using Stromal Cell Conditioned Medium, Cell Death and Disease, 2012, 3:e314, pp. 1-10.
Pieper, et al., Differential Distribution of Competence for Panplacodal and Neural Crest Induction to Non-Neural and Neural Ectoderm, Development, 2012, 139:1175-1187.
Reyes, et al., Glutamatergic Neuronal Differentiation of Mouse Embryonic Stem Cells After Transient Expression of Neurogenin 1 and Treatment with BDNF and GDNF: In Vitro and In Vivo Studies, Journal of Neuroscience, 2008, 28(48):12622-12631.
Schlosser, Induction and Specification of Cranial Placodes, Developmental Biology, 2006, 294:303-351.
Shi, et al., BMP4 Induction of Sensory Neurons from Human Embryonic Stem Cells and Reinnervation of Sensory Epithelium, European Journal of Neuroscience, 2007, 26:3016-3023.
Suga, et al., Self-Formation of Functional Adeno-hypophysis in Three-dimensional Culture, Nature, 2011, 480:57-62.
Warchol, et al., Expression of the Pax2 Transcription Factor is Associated with Vestibular Phenotype in the Avian Inner Ear, Develop. Neurobiol., 2009, 69:191-202.
PCT International Search Report and Written Opinion, PCT/US2013/039686, dated Jul. 17, 2013, 15 pages.
Eiraku, et al., Mouse Embryonic Stem Cell Culture for Generation of Three-Dimensional Retinal and Cortical Tissues, Nature Protocols, 2012 7:69-79.
Hama, et al., Scale: A Chemical Approach for Fluorescence Imaging and Reconstruction of Transparent Mouse Brain, Nature Neuroscience, 2011, 14:1481-1488.
Jegalian, et al., Homeotic Transformations in the Mouse Induced by Overexpression of a Human Hox3.3 Transgene, Cell, 1992, 71(6):901-910.
Wilson, et al., Induction of Epidermis and Inhibition of Neural Fate by Bmp-4, Nature, 1995, 376:331-333.
Ying, et al., The Ground State of Embryonic Stem Cell Self-Renewal, Nature, 2008, 453:519-523.
Nasu, et al. Robust Formation and Maintenance of Continuous Stratified Cortical Neuroepithelium by Laminin-Containing Matrix in Mouse ES Cell Culture, PLOS ONE, Dec. 2012, vol. 7, Issue 12, pp. 1-12.
Fujiwara et al. "Regulation of Mesodermal Differentiation of Mouse Embryonic Stem Cells by Basement Membranes," The Journal of Biological Chemistry, vol. 282, No. 40, pp. 29701-29711, Oct. 5, 2007, pp. 29701-29711.
Koehler and Hashino. "3D mouse embryonic stem cell culture for generating inner ear organoids."Nat Protoc. 2014;9(6)1299-44.
Koehler et al. Recapitulating Inner Ear Development with Pluripotent Stem Cells: Biology and Translation. In Development of Auditory and Vestibular Systems: Fourth Edition. 2014 (pp. 213-247).
Wiley et al. "cGMP production of patient-specific iPSCs and photoreceptor precursor cells to treat retinal degenerative blindness," Scientific Reports, 6:30742, Jul. 29, 2016, pp. 1-16.
Kleinman et al. "Matrigel: Basement membrane matrix with biological activity" Seminars in Cancer Biology 15 (2005) pp. 378-386.
Yurchenco et al. "Basal lamina assembly" Cell Biology, 1994, 6: pp. 674-681.

\* cited by examiner

FIG. 9
Outer epithelial thickening following LDN-193189 treatment is FGF-dependent (d6)
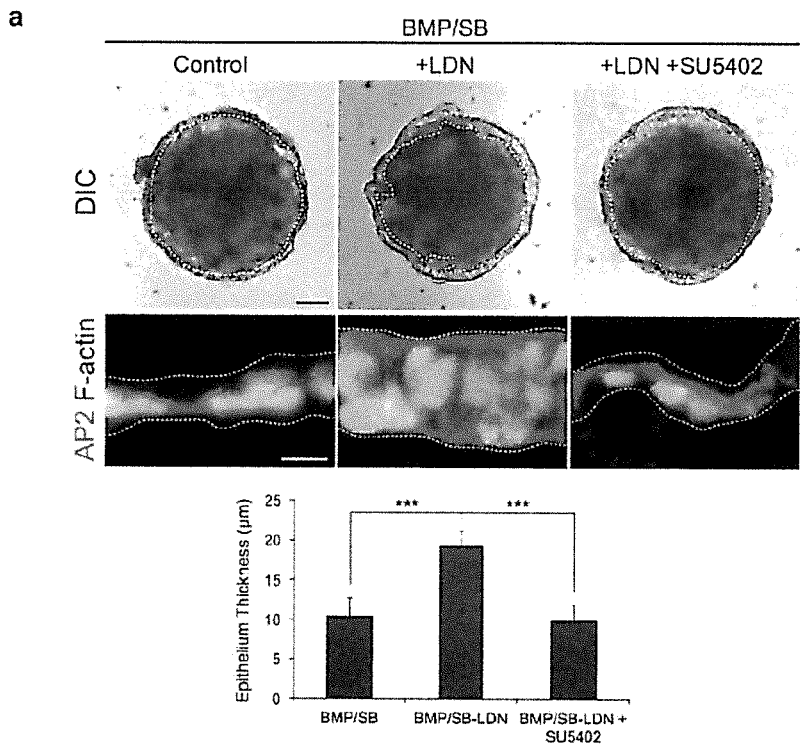
FGF2 induces Pax8 expression in a dose-dependent manner
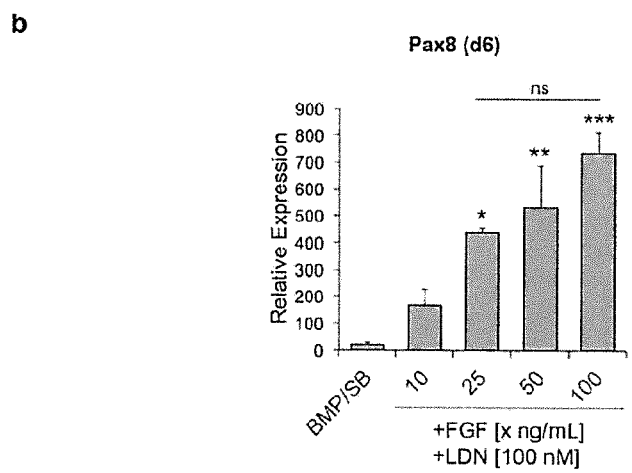

FIG. 11
BMP/SB-FGF/LDN aggregates contains Pax8+ neuroectoderm
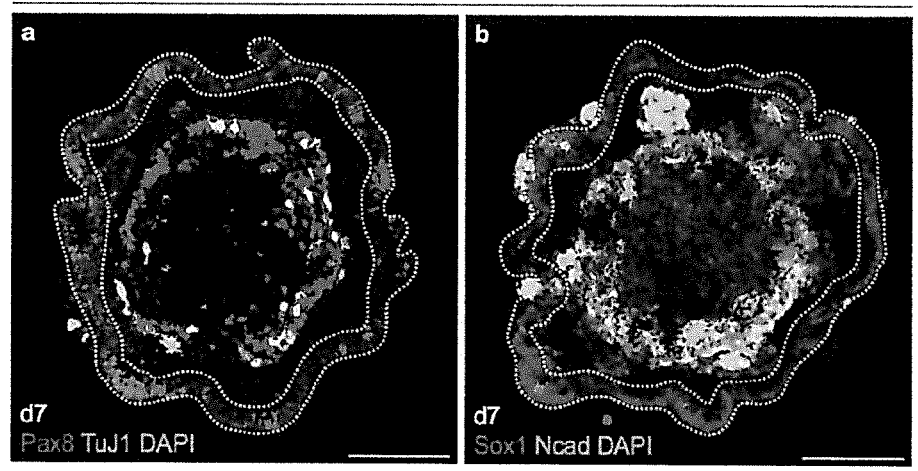
Markers of placodes anterior to the OEPD are absent in the epithelium following BMP/SB-FGF/LDN treatment
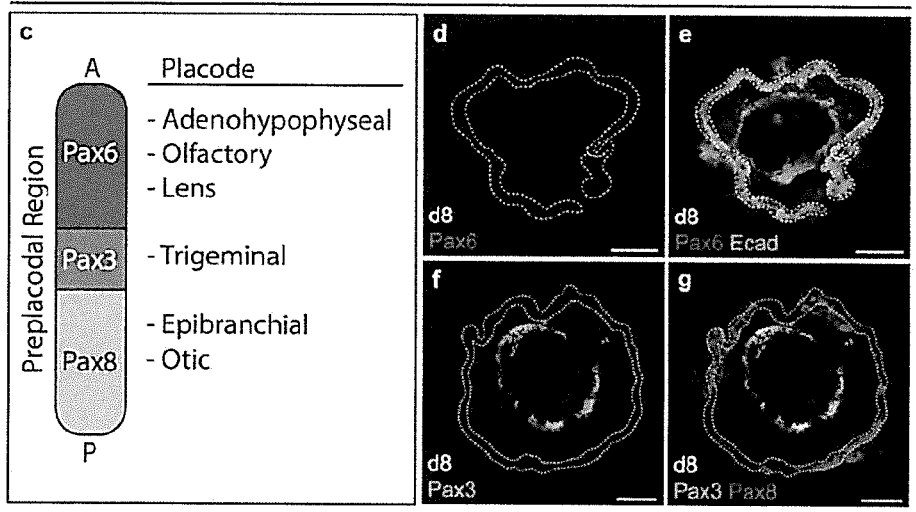

FIG. 12
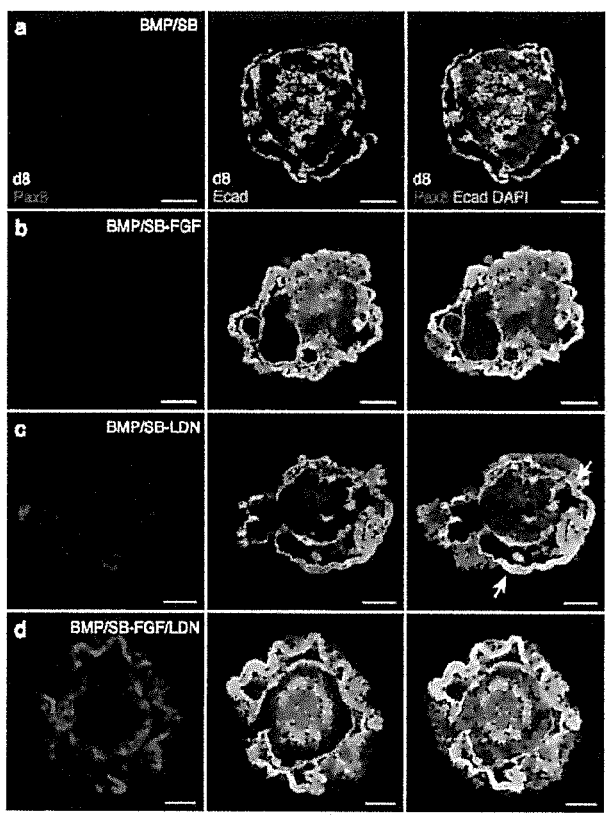
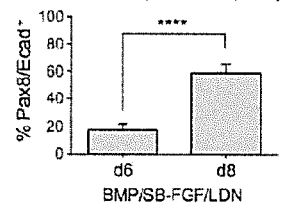
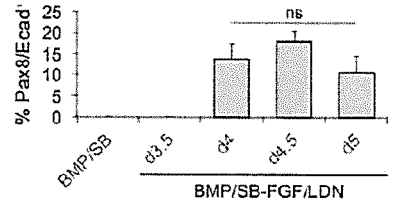

FIG. 13
Cellular re-organization during days 8-12 (BMP/SB-FGF/LDN sections only)
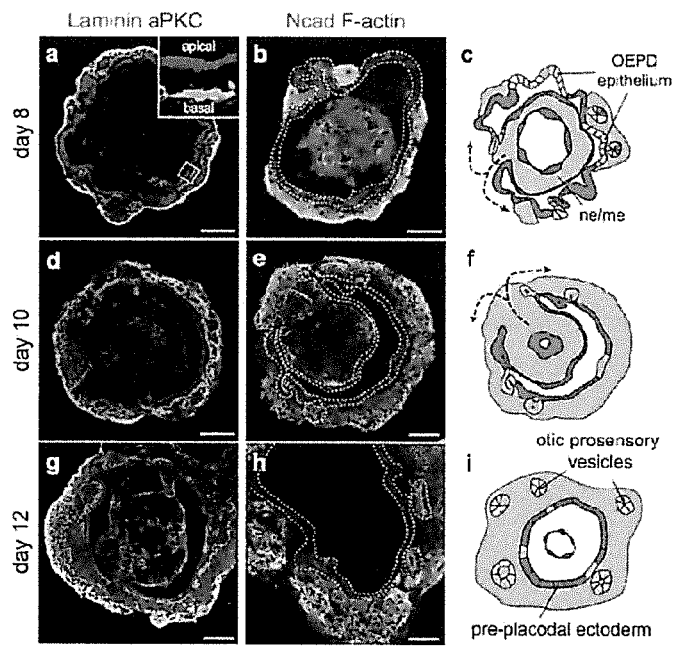
The degree of cellular re-organization differs between conditions
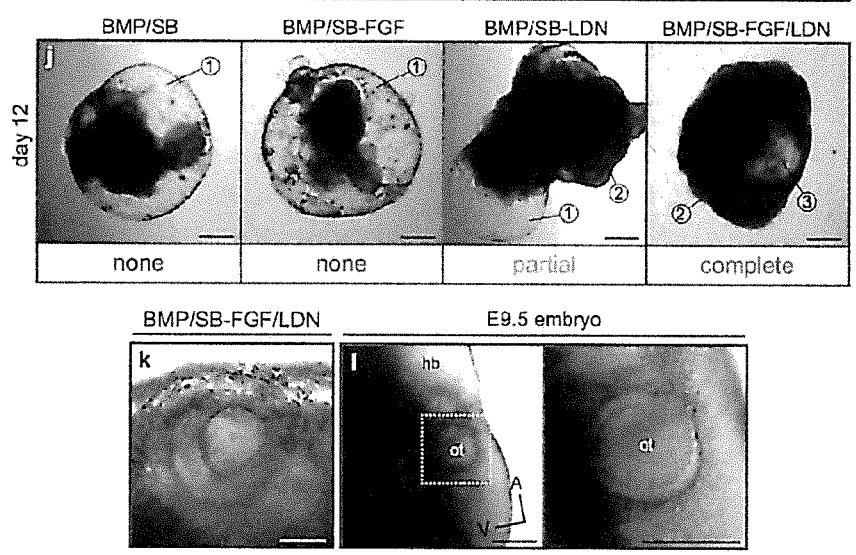

FIG. 16
MyosinVIIa/Jag1/Sox2 labels prosensory otic vesicles (d14)
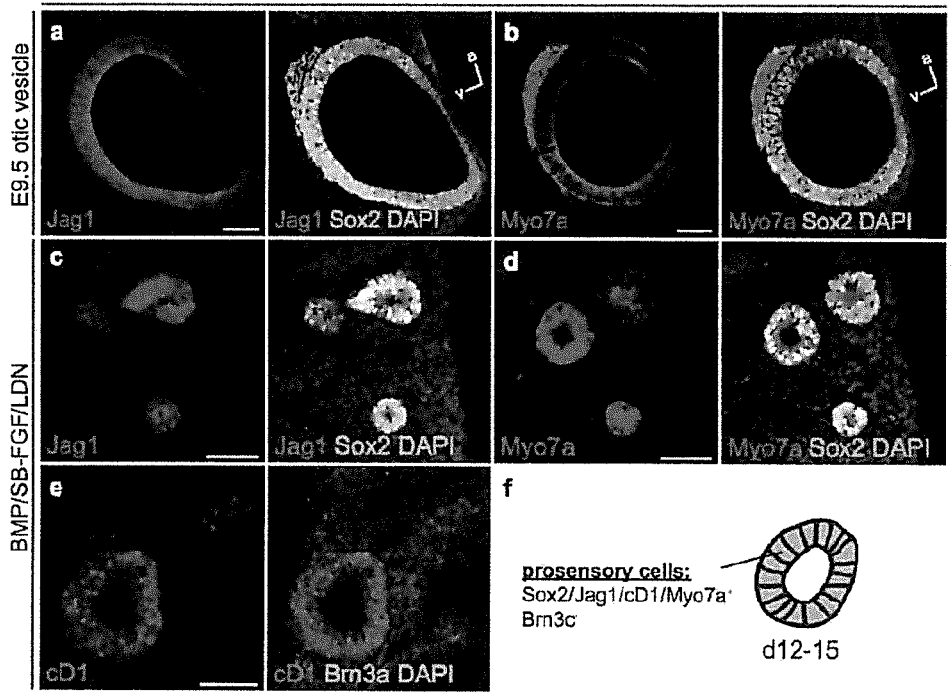
Distinct supporting cells and hair cells in maturing prosensory otic vesicles (d16)
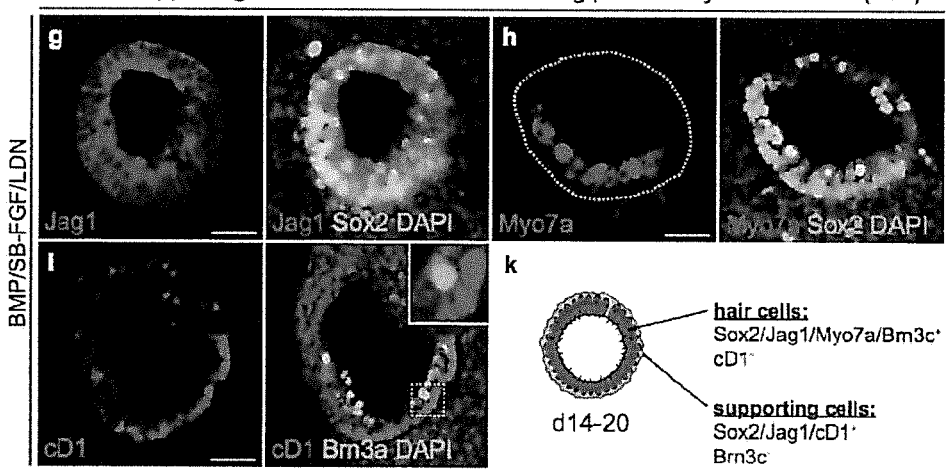

FIG. 17
Brn3c and cD1 label hair cells and supporting cells, respectively.
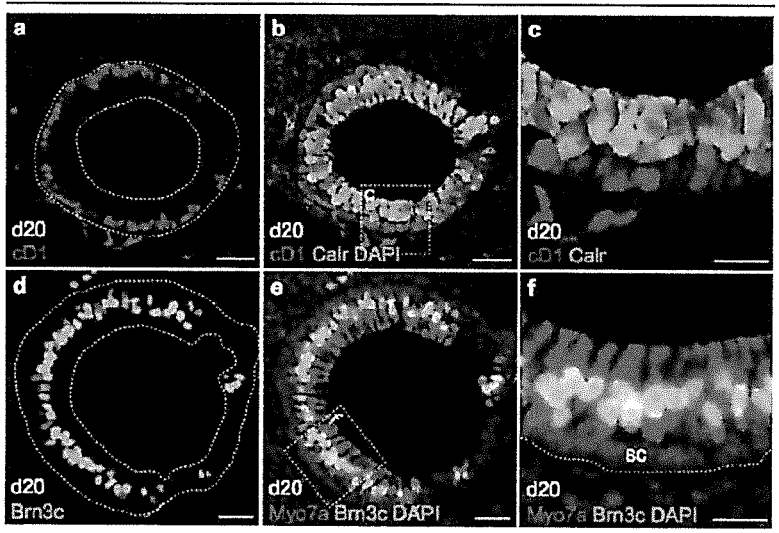
Espin labels stereocilia bundles
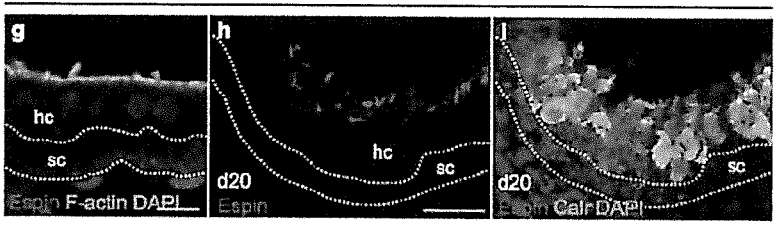
Structural characteristics of kinocilium and stereocilia bundles
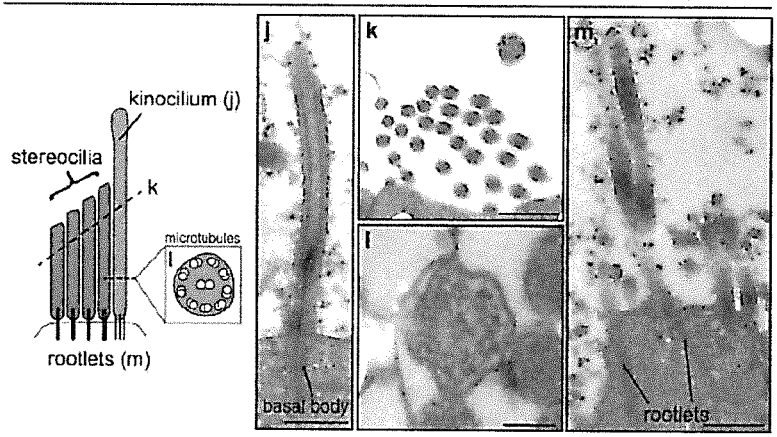

FIG. 19
Neurons express sensory markers and extend processes to hair cells
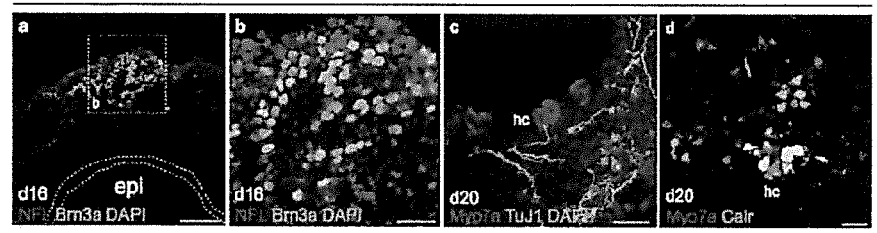
Synaptic markers expressed in hair cells and neurons
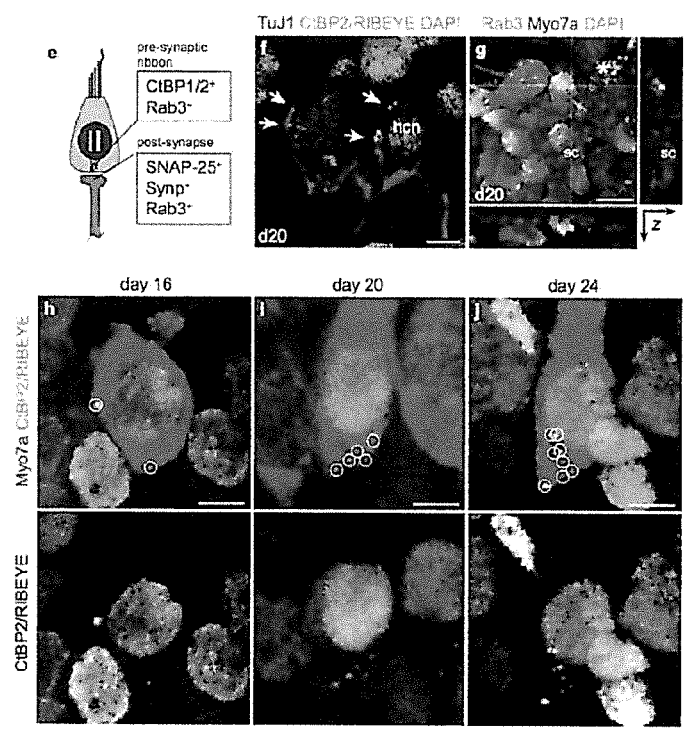

FIG. 27
a
3D to 2D differentiation strategy
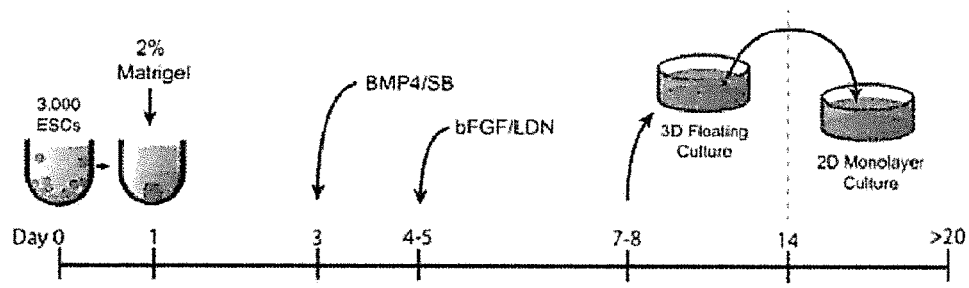
BMP/SB-FGF/LDN – Day 20
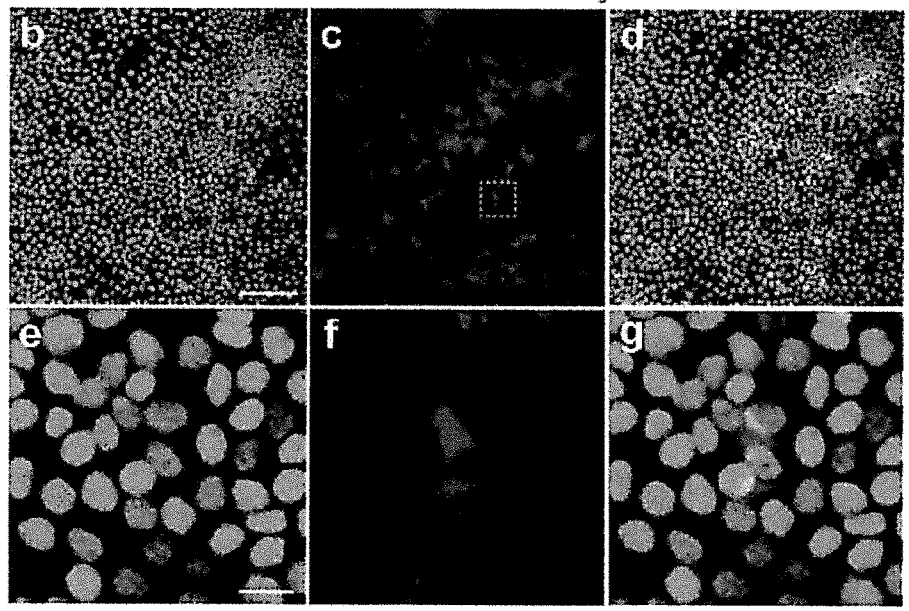
Myo7a Sox2

```
                            SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Dlx3 Forward Primer

<400> SEQUENCE: 1
cagtacggag cgtaccggga                                               20

<210> SEQ ID NO 2
<211> LENGTH: 20
<212> TYPE: DNA
<213> ORGANISM: Artificial Sequence
<220> FEATURE:
<223> OTHER INFORMATION: Dlx3 Reverse Primer

<400> SEQUENCE: 2
tgccgttcac catgcgaacc                                               20

<210> SEQ ID NO 3
<211> LENGTH: 18
<212> TYPE: DNA
<213> ORGANISM: Artificial Sequence
<220> FEATURE:
<223> OTHER INFORMATION: Sox1 Forward Primer

<400> SEQUENCE: 3
aaccaggatc gggtcaag                                                 18

<210> SEQ ID NO 4
<211> LENGTH: 20
<212> TYPE: DNA
<213> ORGANISM: Artificial Sequence
<220> FEATURE:
<223> OTHER INFORMATION: Sox1 Reverse Primer

<400> SEQUENCE: 4
atctccgagt tgtgcatctt                                               20

<210> SEQ ID NO 5
<211> LENGTH: 22
<212> TYPE: DNA
<213> ORGANISM: Artificial Sequence
<220> FEATURE:
<223> OTHER INFORMATION: brachyury Forward Primer

<400> SEQUENCE: 5
cacacggctg tgagaggtac cc                                            22

<210> SEQ ID NO 6
<211> LENGTH: 23
<212> TYPE: DNA
<213> ORGANISM: Artificial Sequence
<220> FEATURE:
<223> OTHER INFORMATION: brachyury Reverse (1) Primer

<400> SEQUENCE: 6
```

```
tgtccgcata ggttggagag ctc                                           23

<210> SEQ ID NO 7
<211> LENGTH: 20
<212> TYPE: DNA
<213> ORGANISM: Artificial Sequence
<220> FEATURE:
<223> OTHER INFORMATION: brachyury Reverse (2) Primer

<400> SEQUENCE: 7
gggaaggtga agagatgagg                                               20

<210> SEQ ID NO 8
<211> LENGTH: 20
<212> TYPE: DNA
<213> ORGANISM: Artificial Sequence
<220> FEATURE:
<223> OTHER INFORMATION: Pax8 Forward Primer

<400> SEQUENCE: 8
cggcgatgcc tcacaactcg                                               20

<210> SEQ ID NO 9
<211> LENGTH: 20
<212> TYPE: DNA
<213> ORGANISM: Artificial Sequence
<220> FEATURE:
<223> OTHER INFORMATION: Pax8 Reverse Primer

<400> SEQUENCE: 9
tgggccaagt ccacaatgcg                                               20

<210> SEQ ID NO 10
<211> LENGTH: 23
<212> TYPE: DNA
<213> ORGANISM: Artificial Sequence
<220> FEATURE:
<223> OTHER INFORMATION: Pax2 Forward Primer

<400> SEQUENCE: 10
cccgttgtga ccggtcgtga tat                                           23

<210> SEQ ID NO 11
<211> LENGTH: 22
<212> TYPE: DNA
<213> ORGANISM: Artificial Sequence
<220> FEATURE:
<223> OTHER INFORMATION: Pax2 Reverse Primer

<400> SEQUENCE: 11
tgggttgcct gagaactcgc tc                                            22
```

METHODS FOR GENERATING THE INNER EAR AND OTHER CRANIAL PLACODE-DERIVED TISSUES USING PLURIPOTENT STEM CELLS

CROSS-REFERENCE TO RELATED APPLICATIONS

This application is a continuation of U.S. application Ser. No. 14/398,664, filed Nov. 3, 2014, which represents the national stage entry of PCT International Application No. PCT/US2013/039686 filed May 6, 2013, which claims priority to U.S. Provisional Patent Application No. 61/642,701 filed May 4, 2012, and Provisional Patent Application No. 61/791,567 filed Mar. 15, 2013, each of which is incorporated by reference herein in its entirety.

STATEMENT REGARDING FEDERALLY SPONSORED RESEARCH OR DEVELOPMENT

This invention was made with government support under DC010706 awarded by the National Institutes of Health. The Government has certain rights in the invention.

BACKGROUND

Over 30 million Americans suffer from moderate to profound sensorineural hearing loss (SNHL). SNHL is caused by a permanent degeneration of the sensory cells responsible for transmitting acoustic information to the brain: either the mechanosensory hair cells and/or the spiral ganglion (SG) neurons. There is no known cure for SNHL. Pallative treatments, such as hearing aids, are used to treat the symptoms of SNHL but no known treatment addresses the underlying cause of SNHL. Cochlear implants, which directly stimulate surviving SG neurons are an effective treatment for some portion of the population having SNHL. However, cochlear implantation is ineffective in nearly 15% of SNHL cases.

Pluripotent stem cells offer a promising approach to both model congenital deafness disorders and produce replacement inner ear sensory cells for curative therapy. Pluripotent cells, such as human embryonic stem (hES) cells and induced pluripotent stem (iPS) cells, can perpetually proliferate and differentiate into cells of each of the three embryonic germ layers (Thomson J, et al., "Embryonic stem cell lines derived from human blastocysts," Science 282:1145-1147 (1998); Odorico J, et al., "Multilineage differentiation from human embryonic stem cell lines," Stem Cells 19:193-204 (2001)). Differentiation of pluripotent cell cultures can occur spontaneously, which results in a seemingly random variety of cells (Watt F & Hogan Bm "Out of Eden: stem cells and their niches," Science 287:1427-1430 (2000)). Alternatively, pluripotent cells can be induced to differentiate, e.g., by co-culturing the cells with cells of particular lineages or by chemical and/or mechanical detachment. The latter can be used to induce formation of embryoid bodies (EB), which, in turn, can differentiate into cells of multiple lineages.

Induced pluripotent (iPS) cells are generated by reprogramming somatic cells or differentiated progenitor cells to a state of pluripotency. Apart from their somatic cell origin, iPS cells share many characteristics of embryonic stem cells, such as the ability to grow perpetually and to differentiate into cells of the three germ layers. Like ES cells, iPS cells express one or more pluripotent cell-specific marker, such as OCT-4, SSEA-3, SSEA-4, TRA-1-60, TRA-1-81, and Nanog. iPS cells have been generated using retroviral vectors that randomly integrate into the target cell's DNA and using non-integrating vectors. iPS cells generated using non-integrating vectors are especially well suited for clinical application.

Generating inner ear cells from pluripotent cells is a significant challenge. Efforts to derive inner ear cells have been hampered by ill-defined culture systems that fail to recapitulate normal inner ear development mechanisms. During embryonic development the inner ear forms from a pool of progenitor cells called the preplacodal region. Previous studies aimed at deriving inner ear cells from pluripotent cells have failed to emphasize the importance of preplacodal cells, derived from non-neural ectoderm, in the differentiation path towards inner ear cells.

As can be appreciated from the above discussion, a need exists for methods to treat the cause of SNHL. Accordingly, it is one of the purposes of the present invention to replace degenerated sensory hair cells and/or auditory neurons, by providing a method for generating non-neural ectoderm, preplacodal ectoderm cells and otic placode cells.

BRIEF SUMMARY OF THE INVENTION

Disclosed herein are methods and compositions for generating preplacodal ectoderms cells and otic placode cells from pluripotent cells. Also described are methods for differentiating pluripotent cells into preplacodal ectoderms cells by a timed exposure to BMP4 and an inhibitor of the TGFβ pathway. Methods for differentiating preplacodal ectoderm cells into otic placode cells include inhibiting the bone morphogenetic protein (BMP) pathway and exposure of preplacodal ectoderm cells to a fibroblast growth factor (FGF), e.g., FGF2. Further described is the differentiation of otic placode cells into inner ear sensory hair cells.

Accordingly, in a first aspect provided herein is a method for producing preplacodal ectoderm cells, the method comprising the steps of: (i) culturing pluripotent stem cells under conditions that result in formation of embryoid bodies from the cultured pluripotent stem cells; (ii) adding one or more extracellular matrix proteins to the cultured embryoid bodies; and (iii) culturing the embryoid bodies in the presence of BMP2, BMP4, or BMP7 and a TGFβ inhibitor to form non-neural ectoderm; and (iv) culturing the non-neural ectoderm formed in (iii) in the absence of the BMP2, BMP4, or BMP7, and the TGFβ inhibitor, and in the presence of an exogenous FGF and a BMP inhibitor, in floating culture, to generate a cell population comprising preplacodal ectoderm cells.

In some embodiments of the first aspect, BMP4 is the BMP to be used in step (iii) of the method.

In some embodiments, the pluripotent stem cells to be used are mouse pluripotent stem cells. In other embodiments the pluripotent stem cells are human pluripotent stem cells.

In some embodiments, where the pluripotent stem cells used in the method are mouse pluripotent stem cells, treatment of the EBs with BMP2, BMP4, or BMP7, and a TGFβ inhibitor is initiated on day 3 after initiating differentiation. In other embodiments, where the pluripotent stem cells used are human pluripotent stem cells, treatment of the EBs with BMP2, BMP4, or BMP7, and a TGFβ inhibitor are initiated from about day 5 to about day 7 (e.g., on day 5) after the beginning of differentiation In some embodiments, the one or more extracellular matrix proteins are added to the cultured embryoid bodies on day 1 of the differentiation method.

In some embodiments the one or more extracellular matrix proteins include laminin, entactin, Matrigel™, or a combination thereof.

In some embodiments, the TGFβ inhibitor to be used is SB 431542 (CAS No. 301836-41-9, A 83-01 (CAS No. 909910-43-6), GW 788388 (CAS No. 452342-67-5), LY 364947 (CAS No. 396129-53-6), RepSox (CAS No. 446859-33-2), SB 505124 (CAS No. 694433-59-5), SB 525334 (CAS No. 356559-20-1), or SD 208 (CAS No. 356559-20-1) at a concentration of about 0.1 µM to about 5 µM. In some embodiments, the TGFβ inhibitor used in the differentiation method is SB 431542 at a concentration of about 1 µM.

In a second aspect provided herein is a method for producing otic placode cells that includes the steps of: (i) culturing pluripotent stem cells under conditions that result in formation of embryoid bodies from the cultured pluripotent stem cells; (ii) adding one or more extracellular matrix proteins to the embryoid bodies; (iii) culturing the embryoid bodies in the presence of a BMP (e.g., BMP2, BMP4, or BMP7) and a TGFβ inhibitor to form a differentiated cell population comprising non-neural ectoderm; (iv) culturing the non-neural ectoderm formed in (iii) in the absence of the BMP2, BMP4, or BMP7, and the TGFβ inhibitor, and in the presence of an exogenous FGF and a BMP inhibitor, in floating culture, to generate preplacodal ectoderm; and (v) culturing the preplacodal ectoderm, in floating culture, in the absence of the exogenous FGF and BMP inhibitor to obtain a cell population comprising otic placode cells.

In some embodiments of the second aspect, the exogenous FGF to be used is an FGF selected from any of FGF1-FGF23. In some embodiments, the exogenous FGF is FGF2, FGF3, FGF10, FGF19 or FGF20. In other embodiments, the FGF is FGF2, e.g., human FGF2.

In some embodiments of the second aspect the method also includes culturing the preplacodal ectoderm in the presence of an activator of Wnt/β-catenin signaling. In some embodiments, the activator of Wnt/β-catenin signaling is a Gsk3 inhibitor.

In some embodiments of the second aspect the pluripotent stem cells to be used are mouse pluripotent stem cells. In some embodiments, where the pluripotent stem cells used are mouse pluripotent stem cells, the BMP and the TGFβ inhibitor are added on day 3, and the exogenous FGF and the BMP inhibitor are added on day 4 or 5.

In other embodiments, the pluripotent stem cells to be used are human pluripotent stem cells. In some embodiments, where the pluripotent stem cells used in the differentiation method are human pluripotent stem cells (e.g., human induced pluripotent stem cells), the BMP and the TGFβ inhibitor are added between days 3-6, and the exogenous FGF and the BMP inhibitor are added between days 6-8.

In some embodiments of the second aspect the exogenous FGF is any of FGF1-FGF23. In some embodiments the exogenous FGF is FGF2, FGF3, FGF10, FGF19, FGF20 or a combination thereof. In some embodiments, the exogenous FGF is FGF2.

In some embodiments of the second aspect, the otic placode cells exhibit increased expression of at least one otic marker gene relative to other cells in the differentiated population, wherein the at least one otic marker gene is selected from the group consisting of Dlx3, Dlx5, Pax2, Pax8, Six1, Eya1, FGF10 and Otx2. In a third aspect provided herein is a method for producing inner ear sensory hair cells that includes the steps of (i) culturing pluripotent stem cells under conditions that result in formation of embryoid bodies from the cultured pluripotent stem cells; (ii) adding an extracellular matrix protein to the embryoid bodies; (iii) culturing the embryoid bodies in the presence of BMP2, BMP4, or BMP7 and a TGFβ inhibitor to form non-neural ectoderm; (iv) culturing the non-neural ectoderm formed in (iii) in the absence of the BMP4 and the TGFβ inhibitor, and in the presence of an exogenous FGF and a BMP inhibitor, in floating culture, to generate preplacodal ectoderm; and (v) culturing the preplacodal ectoderm, in floating culture, in the absence of the exogenous FGF and BMP inhibitor to obtain otic placode and inner ear sensory hair cells differentiating from the otic placode.

In some embodiments of the third aspect, the exogenous FGF to be used is FGF2.

In some embodiments of the third aspect, the method also includes culturing the preplacodal ectoderm from step (v) in the presence of an activator of Wnt/β-catenin signaling. In some embodiments, the activator of Wnt/β-catenin signaling is a Gsk3 inhibitor.

In some embodiments of the third aspect the inner hair sensory hair cells comprise Type II vestibular hair cells. In some embodiments, the inner ear sensory hairs cells include Type I and Type II vestibular hair cells, where the Type II vestibular hair cells outnumber the Type I vestibular hair cells.

In some embodiments of the third aspect the pluripotent stem cells used in the method are mouse pluripotent stem cells. In other embodiments the pluripotent stem cells used are human pluripotent stem cells.

In a fourth aspect provided herein is a composition for differentiation of EBs into non-neural ectoderm, where the composition contains BMP4 and a TGFβ inhibitor.

In some embodiments of the fourth aspect, the TGFβ inhibitor is SB 431542, A 83-01, GW 788388, LY 364947, RepSox, SB 505124, SB 525334, or SD 208. In some embodiments of the fourth aspect, the composition also includes a cell culture medium.

In a fifth aspect described herein is a composition for differentiation of non-neural ectoderm into preplacodal ectoderm, comprising an FGF and a BMP inhibitor. In some embodiments of the fifth aspect, the BMP inhibitor is LDN-193189, DMH1, or Dorsomorphin.

In a sixth aspect described herein is a kit that contains: (i) BMP4 and a TGFβ inhibitor; or (ii) an FGF (e.g., FGF2) and a BMP inhibitor. In some embodiments, the kit contains (i) and (ii).

In a seventh aspect provided herein is an isolated cell population containing inner ear sensory hair cells. In some embodiments, the isolated cell population is a murine isolated cell population. In other embodiments, the isolated cell population is a human isolated cell population.

In some embodiments of the seventh aspect, the inner ear sensory hair cells include Type II vestibular hair cells.

In some embodiment of the seventh aspect, the inner ear sensory hair cells include cells that are immunopositive for Myosin 7a, Brn3c, and Atoh1. In some embodiments, the inner ear sensory hair cells exhibit rapid uptake of FM 1-43 dye, outwardly rectifying potassium currents, and mechanotransduction currents.

In an eighth aspect provided herein is a cell culture that contains a cell culture medium, BMP4, a TGFβ inhibitor, and embryoid bodies (e.g., human embryoid bodies).

In a ninth aspect provided herein is a cell culture that contains an exogenous FGF (e.g., FGF2), a BMP inhibitor, and a cell population containing non-neural ectoderm cells (e.g., human preplacodal ectoderm cells)

In a tenth aspect provided herein is an isolated otic progenitor population comprising a cell population that is immunopositive for Sox2, Jag1, Pax2, Pax8, and E-cadherin.

In an eleventh aspect provided herein is a method for identifying an agent that induces or enhances preplacodal ectoderm to hair cell differentiation in vitro, that includes the steps of: (i) providing a floating culture comprising preplacodal ectoderm; (ii) contacting the floating culture with a test agent; (iii) assessing expression of Atoh1 or Myosin 7a; and (iv) indicating that the test agent is an agent that induces or enhances preplacodal ectoderm to otic placode differentiation in vitro, if expression of Atoh1 or Myosin 7a in the presence of the test agent is higher in the presence of the test agent that in the absence of the test agent.

In an twelfth aspect described herein is a method for identifying an agent that is cytoprotective for sensory hair cells, that includes the steps of: (i) providing a cell culture comprising sensory hair cells; (ii) contacting the cultured sensory hair cells with a cytotoxic agent in the presence of a test agent; (iii) quantifying the presence of one or more markers of cell death in the contacted sensory hair cells; and (iv) indicating that the test agent is cytoprotective if the level of the one or more markers of cell death in the presence of the test agent and the cytotoxic agent are lower than in the presence of the cytotoxic agent in the absence of the test agent.

In a thirteenth aspect provided herein is a differentiated embryoid body (e.g., a human embryoid body) that has an $ECAD^+$ outer epithelium, a $Sox1^+/NCAD^+$ intermediate layer, and a $NANOG^+$ inner core.

Other objects, features and advantages of the present invention will become apparent after review of the specification, claims and drawings. The detailed description and examples enhance the understanding of the invention, but are not intended to limit the scope of the appended claims.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 9 shows epithelial thickening is FGF-dependent and Pax8 expression is dependent on FGF dosage. a, Inhibition of FGF using SU5402, abolishes epithelial thickening following BMP/SB-LDN treatment (n=9 aggregates, 3 separate experiments, ***$P<0.001$). AP2 expression, however, is still found in the outer epithelium following SU5402 treatment. b, qPCR analysis shows that Pax8 expression is dependent on FGF dosage. FGF dosages >25 ng/mL showed an upward trend in Pax8 expression, however, differences between 25, 50 and 100 ng/mL were not significant using a one-way ANOVA with Tukey's post hoc test for multiple comparisons. 25 ng/mL was chosen as the appropriate dosage for all subsequent experimentation (n=4, *$P<0.05$, $P<0.01$, *$P<0.001$; mean±s.e.m.). Scale bars, 100 µm (a, top panels) and 10 µm (a, middle panels).

FIG. 11 shows the cellular composition and organization of BMP/SB-FGF/LDN treated aggregates. a, b, An interior layer of Pax8 and Sox1/Ncad+ cells develops in BMP/SB-FGF/LDN aggregates. This expression pattern is consistent with developing mid-hindbrain tissue. Notably, βIII-tubulin (TuJ1)+ neurons developed within this region, confirming a neural identity. c, In the pre-placodal region of the embryo, Pax6 expression delineates the anterior placodes (i.e. the adenohypopheseal, olfactory and lens placodes), whereas Pax3 is expressed in the trigeminal placode. d, e, Pax6 is not expressed in day 8 BMP/SB-FGF/LDN treated aggregates. f, g, Pax3 is expressed in Pax8+ cells located in the interior layer, however, no Pax3 expression was observed in the outer-epithelium. Scale bars, 100 µm. We speculate that FGF/LDN treatment guides cell fate specification at multiple layers of the aggregates. In the outer epithelium, FGF/LDN induces a pre-placode-like epithelium and, specifically, an epithelium similar to that of the OEPD. Comparably, FGF/LDN appears to act on an inner layer of neuroectodermal cells to induce mid-hindbrain-like tissue. It is likely that the insulin content of Knockout Serum Replacement contributes to the caudalizing affect of FGF/LDN treatment. Previously, insulin and FGF2 were used to induce mid-hindbrain in SFEBq culture. Likewise, mechanosensitive hair cells were previously derived using, in part, insulin-like growth factor and FGF2.

FIG. 12 shows necessity and proper timing of FGF/LDN treatment for Pax8 induction. a-d, Representative immunostaining for Pax8/Ecad on day 8 of differentiation. For BMP/SB-LDN treated aggregates arrows identify the patches of Pax8/Ecad+ cells. We conclude from these results that the combined treatment of FGF/LDN or, potentially, LDN combined with endogenous FGFs is necessary to induce Pax8/Ecad+ epithelium. e, Percentage of Ecad+ epithelium expressing Pax8 on day 6 and 8 (n=9 aggregates, three separate experiments, ****P<0.0001, mean±s.e.m.). For these experiments FGF/LDN treatment was performed on day 4.5. ns, not significant. Scale bars, 100 µm. f, FGF/LDN treatment only generated Pax8/Ecad epithelium following treatment on days 4-5. FGF/LDN treatment after d5 did not result in epithelial thickening (data not shown). The graph shows quantification of the average percentage of Pax8/Ecad+ epithelium on day 6 (n=9 aggregates, 3 separate experiments; mean±s.d.). Representative images for BMP/SB and BMP/SB-FGF/LDN can be found in FIGS. 2 d and e.

FIG. 13 shows cellular re-organization and vesicle formation in BMP/SB-FGF/LDN aggregates. a-i, To elucidate the process of cellular re-organization during days 8-12, aggregates were stained for basal (laminin) and apical (aPKC) polarity markers (a, d, g). Note that the basal surface of the epithelium remains oriented toward the outside of the aggregate as the inner cell mass relocates to the out surface of the aggregate. Ncad (a marker for both neuroectoderm and mesoderm in vivo) labeled most cells in the inner cell mass and helps visualize the topographical change (b, e, h) depicted in c, f and l. F-actin staining was used to identify the epithelium. Presumptive otic vesicles (dotted outline in h) express Ncad. j, Representative DIC images of aggregates on day 12 could be assessed for cellular re-organization based on morphology. Note the translucent epithelium found in all conditions except BMP/SB-FGF/LDN treated samples. (1) This translucent epithelium is indicative of incomplete or partial re-organization. (2) An opaque outer cell mass was indicative of partial or complete re-organization. (3) Fully re-organized aggregates display a hallow core that is clearly visible through the aggregate surface (images are representative of ~90-95% of aggregates for each condition; n=4). k, From day 8-20, vesicles were visible under the surface of BMP/SB-FGF/LDN treated aggregates (day 12 shown). l, The embedded BMP/SB-FGF/LDN vesicles were comparable in appearance to the otic vesicle in E9.5 mouse embryos as viewed through the surface ectoderm. hb, hindbrain; ot, otic vesicle. Scale bars, 250 µm (j, l), 100 µm (a-i) 50 µm (k).

FIG. 16 shows early hair cell induction (d14-16) a-f, At day 14 of differentiation, prosensory vesicles express Sox2/Jag1/Myo7a, mimicking the expression pattern of the E9.5 otic vesicle. e, Prosensory cells also expressed cD1, but did not express the hair cell marker Brn3c. g-k, Maturing prosensory otic vesicles express Jag1/Sox2 in both supporting cells and hair cells, while Myo7a/Brn3c and cD1 expression in confined to hair cells and supporting cells, respectively. f, k, Schematic showing the characteristics of prosensory otic vesicles observed between days d12-15 versus vesicles with further differentiated sensory epithelia containing hair cells and supporting cells observed between days 14-20. Scale bars, 50 µm (a-e), 25 µm (g-i).

FIG. 17 shows hair cell maturation (d16-20) a-f, Brn3c and cO1 delineate hair cells fi:orn supporting cells in d20 epithelia. g-i, Stereocilia bundles express Espin, characteristic of stereocilia on authentic inner ear hair cells. j-m, Transmission electron microscopy reveals several ultrastructural hallmarks found in stern cell-derived hair cells. Notably, a single kinocilium with basal body (j, k) was associated with each bundle of stereocilia (k). Cross-sections of kinocilia displayed the characteristic configuration of 9 microtuble doublets surrounding 2 central microtubules. Also, stereocilia have rootlets (m) that extended into the cell body. Scale bars, 25 µm (a-i), 500 nm (j, k, m), 100 nm (l).

FIG. 19 shows sensory neurons and synapse formation in BMP/SB-FGF/LDN aggregates (d16-20). Clusters of neurofilament/Brn3c$^+$ neurons (a, b) were found in day 16 aggregates. c, TuJ1$^+$ neuronal processes were observed extending toward Myo7a+ hair cells (hc). d, Calretinin+ neurons extended processes toward and made contact (arrow) with hair cells. Calretinin expression is associated with sensory neurons of the inner ear vestibular and auditory ganglia. e, Schematic of Type II vestibular hair cells highlighting several pre- and post-synaptic markers at ribbon synapses. f, TuJ1$^+$ neuronal processes are associated with CtBP2/RIBEYE$^+$ puncta in stem cell-derived hair cells. Note that the CtBP2/RIBEYE antibody labels ribbon synapses and hair cell nuclei (hcn). g, Rab3$^+$puncta were found on the basal end of Myo7a$^+$ hair cells and neuronal process (asterisks). Supporting cells (sc) have been labeled for orientation h-i, Representative images showing the increase in CtBP2/RIBEYE+ puncta (white circles) found on hair cells over time in culture (d16, 20 and 24). Scale bars, 50 μm (a), 25 μm (b-d), 10 μm (g), 5 μm (f, h-j).

FIG. 27 shows that supporting cells and hair cells originating in EBs during the described otic differentiation methods can be cultured as a monolayer following BMP/SB-FGF/LDN EB floating culture. (a), Overview of 3D to monolayer culture. (b-g), Sox2+ supporting cells with overlaying Myo7a+ hair cell-like cells.

Figure 1:
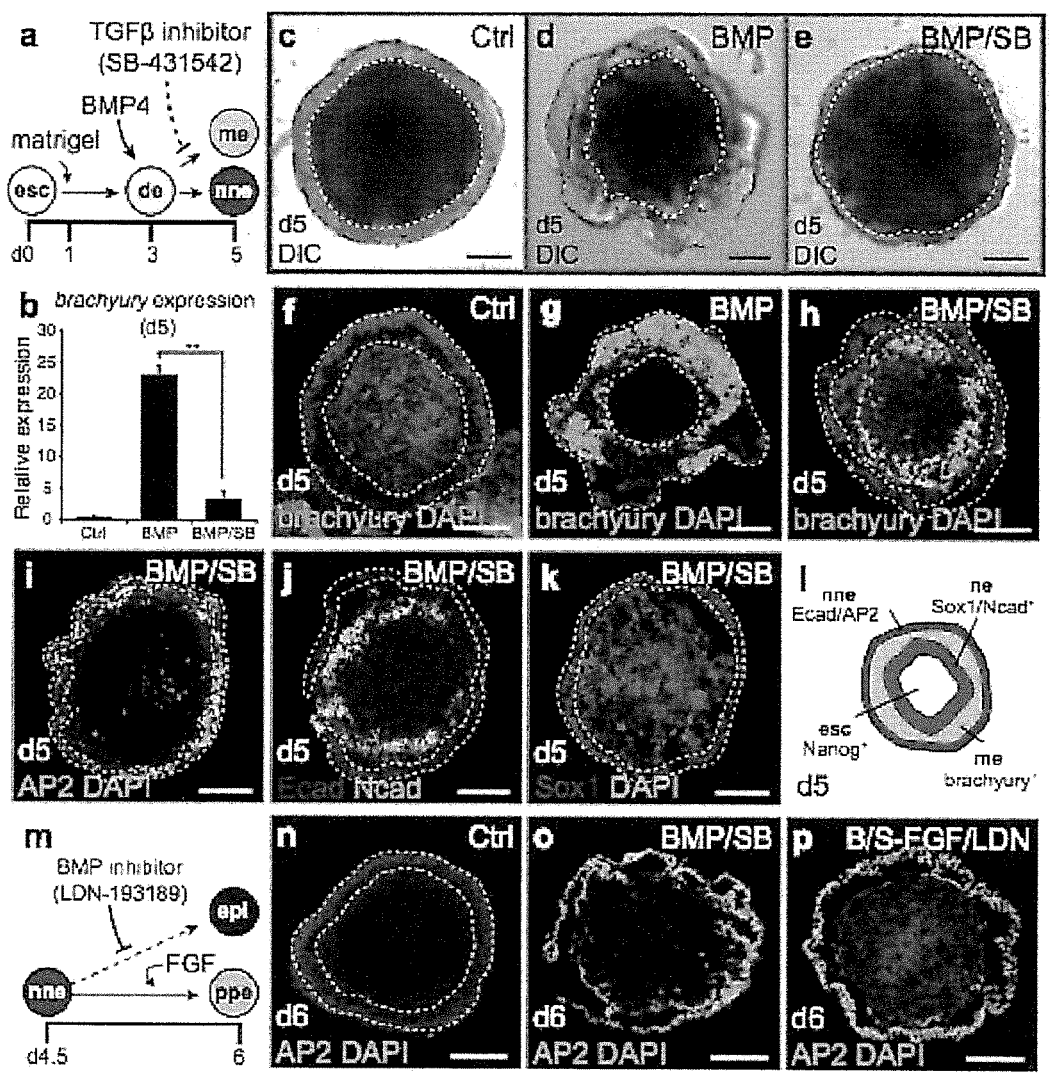
FIG. 1 shows non-neural and pre-placodal ectoderm induction in 3D culture. a, Non-neural ectoderm induction strategy. de, definitive ectoderm; me, mesendoderm; nne, non-neural ectoderm; ne, neuroectoderm. b, SB decreases the level of brachyury expression induced by BMP (n=3; **P<0.01; mean±s.e.m.). c-e, Morphology of control (Ctrl), BMP, and BMP/SB aggregates. f-h, Brachyury+ cells are less prevalent in BMP/SB aggregates. i-k, BMP/SB aggregates contain an outer AP2/Ecad+ epithelium and an interior Sox1+ and Ncad+ cell layer. l, BMP/SB aggregate composition on day 5. m, Pre-placodal ectoderm induction strategy. epi, epidermis; ppe, pre-placodal ectoderm. n-p, BMP/SB-FGF/LDN are distinguished by a thickened AP2+ epithelium absent in other conditions. Scale bars, 100 µm.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements.

Likewise, many modifications and other embodiments of the present invention set forth herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

"embryoid bodies" and "cell aggregates," as used herein, refer to three-dimensional aggregates of pluripotent stem cells.

"pluripotent stem cells," as used herein, refers to embryonic stem cells (ESCs) or induced pluripotent stem cells.

"precursors," as used herein, refers to any cell type that is generated earlier in the same lineage giving rise to a particular cell type.

I. Overview

The inner ear contains specialized sensory epithelia that detect head movements, gravity and sound. It is currently unclear how to derive these sensory epithelia from pluripotent stem cells, a process which will be critical for modeling inner ear disorders in vitro or developing cell-based therapies for profound hearing loss and balance disorders. To date, attempts to derive inner ear mechanosensitive hair cells and sensory neurons have relied on genetic manipulation, co-culture with embryonic inner ear tissues, or undefined conditioned media. These efforts have resulted in inefficient and incomplete phenotypic conversion of stem cells into inner ear-like cells. A key insight lacking from these previous studies is the importance of the non-neural and pre-placodal ectoderm, two critical precursors during inner ear development[8-11]. Described herein are methods and compositions for generating inner ear sensory epithelia from pluripotent stem cells (PSCs). The described methods include timed steps to control BMP, TGFβ, and FGF signaling, starting from ESC aggregates (EBs), to induce sequential differentiation of EBs into non-neural ectoderm, pre-placodal. otic placode-like epithelia, and subsequently into inner ear hair cells. Surprisingly, in a self-organized process that mimics normal development, vesicles containing prosensory cells emerge from the presumptive otic placodes and give rise to hair cells bearing stereocilia bundles and a kinocilium. Moreover, these stem cell-derived hair cells exhibit functional properties of native mechanosensitive hair cells and have the ability to form specialized synapses with sensory neurons co-generated from PSCs in culture. This disclosure establishes a novel in vitro model of inner ear differentiation that can be used to gain deeper insight into inner ear development and disorder.

II. Methods

Generation of Non-Neural Ectoderm, Preplacodal Ectoderm, Otic Placode, and Inner Ear Sensory Hair Cells from Pluripotent Stem Cells In some embodiments, a method for generating preplacodal ectoderm cells includes the steps of culturing pluripotent stem cells under conditions that result in the formation of embryoid bodies (EBs) from the cultured pluripotent stem cells. Subsequently an extracellular matrix protein is added to the cultured EBs, and the EBs are then cultured in the presence of a BMP e.g., BMP2, BMP4, or BMP7 and a TGFβ inhibitor to form a differentiated cell population comprising preplacodal ectoderm cells.

In some embodiments mouse ES (mES) cells are maintained under feeder-free conditions on a protein or peptide substrate, e.g., gelatin or vitronectin. Alternatively, mouse induced pluripotent stem cells are used. In one exemplary embodiment, a suitable medium for culture of mES cells and formation of EBs is "2i-LIF" medium. 2i-LIF Medium is made by supplementing N2B27 Medium with 1000 U/mL leukemia inhibitory factor (LIF; Millipore), a Gsk3 inhibitor 3 µM CHIR99021 (Stemgent), and a MEKK inhibitor 1 µM PD0325901 (Santa Cruz). N2B27 Medium consisted of a 1:1 mixture of Advanced™ DMEM/F12 and Neurobasal Medium (Invitrogen) supplemented with B27® supplement (1× final concentration); N2 supplement (1× final concentration), 1 mM GlutaMax (Invitrogen), and 1 mM Penicillin/Streptomycin (STEMCELL Technologies).

As illustrated in FIG. 27, in one embodiment, floating culture cell aggregates are transferred at about day 14, to a suitable adherent cell substrate (e.g. Laminin, Fibronectin, MATRIGEL™ (a gelatinous protein mixture secreted by Engelbreth-Holm-Swarm (EHS) mouse sarcoma cells), etc.) to continue differentiation of otic placode to hair cells in a monolayer culture system.

In other embodiments, human pluripotent stem cells (hPSCs) are maintained under feeder-free conditions. In some embodiments, hPSCs are maintained in Essential 8™ medium while growing on a vitronectin or Matrigel™ substrate. Alternatively, a medium such as mTeSR™-1 is used for maintenance of hPSCs.

In some embodiments, where hPSCs are maintained under feeder-free conditions in Essential 8™ medium, splitting of cells is carried out with Versene (EDTA) for efficient passaging.

In an exemplary embodiment using mES cells, during days 0-3, serum-free floating culture of embryoid body-like aggregate with quick reaggregation (SFEBq) to generate EBs is initiated by dissociation of adherent mES cells into a cell suspension by trypsinization (e.g., with 0.25% Trypsin-EDTA, and resuspended in "Differentiation Medium". Differentiation Medium is composed of Glasgow Minimal Essential Medium (G-MEM) supplemented with 1.5% knockout serum replacement (KSR; Invitrogen), 0.1 mM non-essential amino acids, 1 mM sodium pyruvate, 1 mM Penicillin/Streptomycin and 1 mM 2-mercaptoethanol. Cells are then plated in 100 µl/well in a range of about 1,000-15,000 cells, but preferably about 3000 cells, a in 96-well low cell adhesion U-bottom plates. On day 1, half of the medium in each well is exchanged for fresh Differentiation Medium containing an extracellular matrix protein, e.g., MATRIGEL™ (a gelatinous protein mixture secreted by Engelbreth-Holm-Swarm (EHS) mouse sarcoma cells) (2% v/v final concentration), laminin (50-400 µg/ml), or laminin plus entactin (50-400 µg/ml each).

On day 3 after initiating formation of EBs, a BMP, e.g., BMP2, BMP4, or BMP7 and a TGFβ inhibitor are added to the culture medium. The concentration of BMP, e.g., BMP4, to be used in the method can range from at least about 1 ng/ml to about 50 ng/ml, e.g., about 2 ng/ml, 4 ng/ml, 5 ng/ml, 7 ng/ml, 12 ng/ml, 15 ng/ml, 20 ng/ml, 25 ng/ml, 32 ng/ml, 40 ng/ml, or another concentration of a BMP from at least about 1 ng/ml to about 50 ng/ml. In some embodiments, the BMP to be used is BMP4 at a concentration of about 10 ng/ml. BMP 4. In some embodiments, the TGFβ inhibitor to be used is SB 431542 (CAS No. 301836-41-9, at a final concentration of about 1 µM). Alternatively, any of the following TGFβ inhibitors may be used: A 83-01 (CAS No. 909910-43-6), GW 788388 (CAS No. 452342-67-5), LY 364947 (CAS No. 396129-53-6), RepSox (CAS No. 446859-33-2), SB 505124 (CAS No. 694433-59-5), SB 525334 (CAS No. 356559-20-1), or SD 208 (CAS No. 356559-20-1) at a concentration of about 0.1 µM to about 5 µM.

This treatment of EBs yields a population of cells non-neural ectoderm cells characterized by expression of AP2, Dlx3, Six1, GATA3 and the absence of the mesendodermal marker brachyury or the absence of the neuroectodermal marker N-cadherin.

On day 4-5, the differentiation medium is replaced with differentiation medium containing FGF2 in a final concentration range of about 5 ng/ml to about 100 ng/ml (with a preferred final concentration of about 25 ng/mL) or another FGF selected from FGF 1-FGF23), and a BMP inhibitor. In some embodiments, the BMP inhibitor is LDN-193189 (CAS No. 1062368-24-4 at about 100 nM). Alternatively, DMH1 (CAS No. 1206711-16-1) or Dorsomorphin (CAS No. LDN-193189) can be used as the BMP inhibitor were added to each well at 6× concentration in 25 µL of fresh media. The extracellular matrix protein concentration (e.g., MATRIGEL™ (a gelatinous protein mixture secreted by Engelbreth-Holm-Swarm (EHS) mouse sarcoma cells) at 2% (v/v)) is maintained throughout days 1-8. Culture of the non-neural ectoderm cells under these conditions yields preplacodal ectoderm, epithelium characterized by expression of at least one of Dlx3, Dlx5, Pax2, Pax8 and Eya1. The concentration of MATRIGEL™ (a gelatinous protein mixture secreted by Engelbreth-Holm-Swarm (EHS) mouse sarcoma cells) or another extracellular matrix protein, as mentioned herein, is maintained at 2% (v/v) throughout days 1-8.

On day 8 of differentiation, cell aggregates are transferred to 24 well plates (Lipidure Coat, NOF; 4-8 aggregates per well) in N2 Medium containing 1% MATRIGEL™ (a gelatinous protein mixture secreted by Engelbreth-Holm-Swarm (EHS) mouse sarcoma cells) (v/v). N2 Medium contains Advanced DMEM/F12, 1×N2 Supplement, 1 mM Penicillin/Streptomycin or 50 µg/mL Normocin (Invivogen) and 1 mM GlutaMax.

In some embodiments, starting at day 8, the cell aggregates are cultured in the presence of an activator of Wnt/β-catenin signaling. In some embodiments, the activator of Wnt/β-catenin signaling is a Gsk3 inhibitor. In some embodiments, the Gsk3 inhibitor is selected from the group consisting of CHIR 99021, CHIR 98014, BIO-acetoxime, LiCl, SB 216763, SB 415286, AR A014418, 1-Azakenpaullone, and Bis-7-indolylmaleimide. In some embodiments, the Gsk3 inhibitor is CHIR 99021, CHIR 98014, or BIO-acetoxime. In one embodiment, the Gsk3 inhibitor is CHIR 99021 or CHIR 98014 at a concentration of at least about 2 µM to about 10 µM in the medium, e.g., 2.5 µM, 3 µM, 4 µM, 5 µM, 7 µM, 8.5 µM, or another concentration from about 2 µM to about 10 µM. In some embodiments, the Gsk3 inhibitor is CHIR99021. In some embodiments, the concentration of CHIR99021 to be used is about 3 µM. In other embodiments, the Gsk3 inhibitor comprises an RNAi targeted against Gsk3. In other embodiments, the activator of Wnt/β-catenin signaling is R-Spondin I.

Typically, half of the medium is changed every day during long-term floating culture for up to 30 days to obtain populations of cells comprising inner ear sensory hair cells, which can be identified based on a number of characteristics including, but not limited to expression of, Myo7a, Sox2 dual expression, or Atoh1 expression; the presence of acetylated-alpha-tubulin-positive kinocilia; rapid uptake of FM 1-43 dye, and the presence of outwardly rectifying potassium currents, as well as mechanosensitive currents as detected by whole cell patch clamp recording.

In another exemplary embodiment, hPSCs are used for differentiation.

On day 0, 80%-confluent hPSCs, maintained under feeder free conditions as described above, are dissociated from their substrate with 0.25% trypsin-EDTA, or a similar protease-based dissociation agent for 1-2 minutes. Afterwards, the trypsinization is quenched by addition by about 2-3 volumes of "Differentiation Medium with Knockout Serum Replacement" (DMK), having the following composition: GMEM with Knockout Serum Replacement (2%), sodium pyruvate (1 mM), Non-Essential amino acids (0.1 mM), β-Mercaptoethanol (0.1 mM), Normocin™ (0.1 mg/ml), and the Rho kinase inhibitor (ROCKi) Y27632 (20 µM). The resulting hPSC clumps are dissociated into a single-cell suspension by trituration, pelleting by low speed centrifugation, resuspension, and filtering through a strainer top flow cytometry tube.

The resulting cell suspension is then plated in a low-adhesion 96-well U-bottom plate(s) (Nunc) in DMK at a density of about 3,000-15,000 cells per well, e.g., about 4,000 cells/well, 5,000 cells/well, 6,000 cells/well, 7,000 cells/well, 8,000 cells/well, 9,000 cells/well, 10,000 cells/well, 11,500 cells/well, 13,000 cells/well, or another number of cells/well from about 3,000 cells/well to about 15,000 cells/well in a 96 well plate. In some embodiments, the number of cells/well in a 96-well plate is about 7,000 cells/well to about 10,000 cells/well.

On day 1 or 2, half of the medium is replaced, and Matrigel™ is added to a final concentration of 1% (v/v), and the hPSCs are allowed to aggregate, under non-adherent culture conditions, into EBs. Around day 5 (day 5, 6, or 7), BMP4 (10 ng/ml) and a TGFβ inhibitor, e.g., SB-431542 (1 µM) are added to the medium.

On day 7, the previous medium is replaced with DMK medium containing FGF2 (25 ng/mL final concentration) and the BMP inhibitor SB-431542 (1 µM final concentration). Optionally, the Sonic Hedgehog (Shh) agonist Purmorphamine can also be added to the medium at a final concentration of 2 µM to increase proliferation in the preplacodal epithelium.

At about day 12, a wide-mouth pipette tip is used to transfer EBs to a 50 ml conical tube and washed twice with N2-DMEM/F12 medium having the following composition: DMEM-F12 (base medium), N2 Supplement (1×), GlutaMAX™ (Invitrogen) (1×), and Normocin (Invivogen) (50 µg/ml).

After washing, individual EBs are transferred 1/well to a low-adhesion 96 well plate for extended floating culture and differentiation into otic placode and eventually inner ear sensory hair cells as described herein. Alternatively, EBs (about 4-6/well) are placed in a Lipidure-coated 24-well plate and maintained in floating culture with half-medium changes every day for 120 days and beyond while differentiation of preplacodal ectoderm to otic placode and inner hair cell differentiation proceeds.

By about day 20, cultures are checked for the expression of otic placode or inner ear sensory hair cell markers as described above. Similarly, other characteristics of inner ear sensory hair cells, e.g., the presence of acetylated-alpha-tubulin-positive kinocilia; rapid uptake of FM 1-43 dye, and the presence of outwardly rectifying potassium currents.

As with mPSCs, in some embodiments, an activator of Wnt/β-catenin signaling, e.g., a Gsk3β inhibitor, e.g., one of the above-mentioned inhibitors, is added to the medium within a concentration range of about 1 µM to about 10 µM, e.g., 2 µM, 2.5 µM, 3 µM, 4 µM, 5 µM, 7 µM, 8 µM, or another concentration from about 1 µM to about 10 µM. In one embodiment, the Gsk3 β inhibitor is CHIR99021 used at a final concentration of about 3 µM. In some embodiments, purmorphamine is maintained continuously throughout the extended floating culture period at a concentration of about 2 µM.

Generation of Placodes Other than Otic Placode

Figure 25:
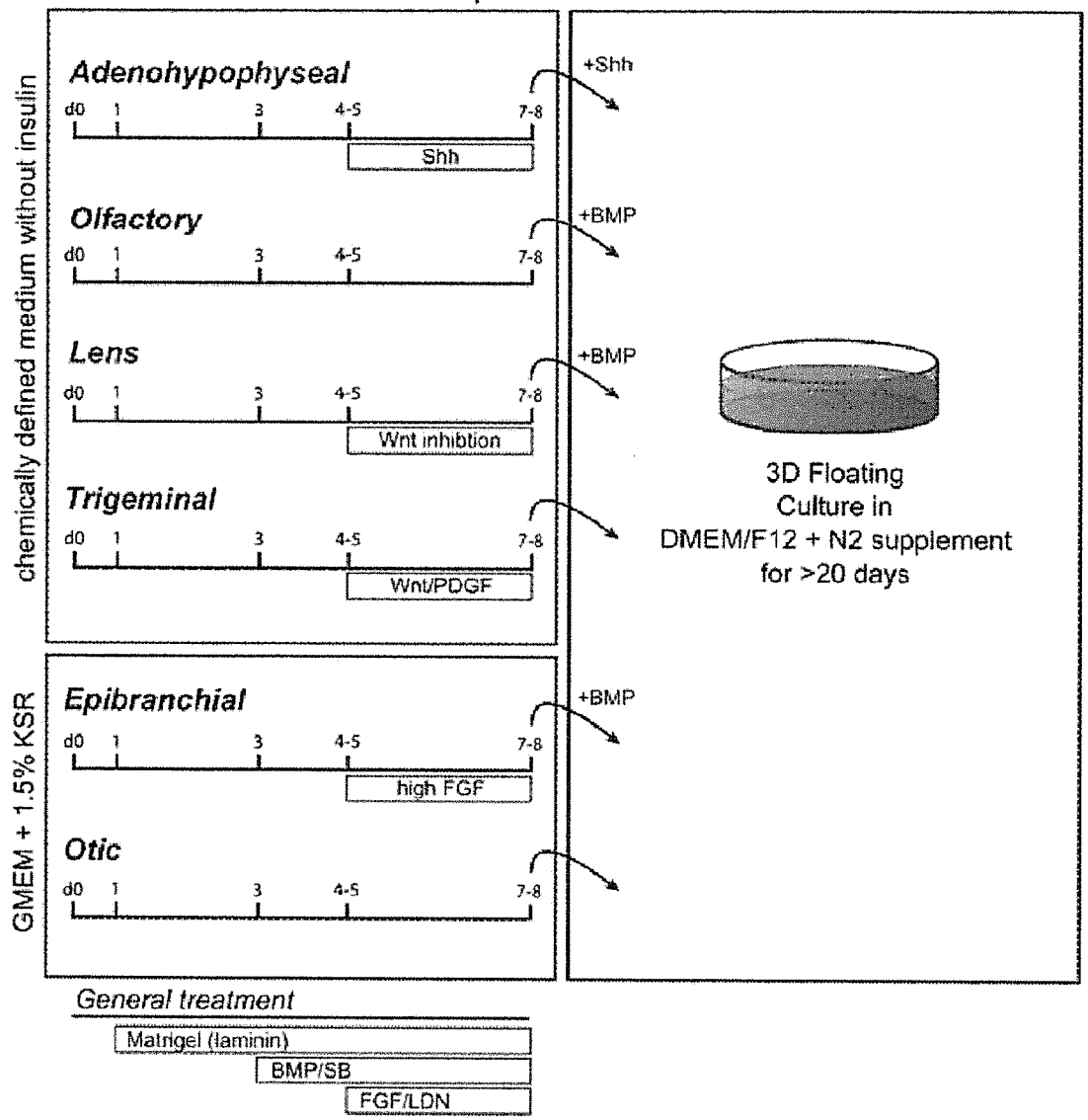
FIG. 25 shows a schematic illustration of exemplary, non-limiting embodiments for deriving cranial placode tissue from mouse PSCs. Sequential treatment of EBs with BMP/SB-FGF/LDN is used for derivation of each placode, although base media are different in some cases. Day 7-8 EBs are transferred to a floating culture in N2 Medium (as described herein) for long-term differentiation (Left Panel). Adenohypophyseal, olfactory, lens and trigeminal placode derivation require the use of a growth factor-free chemically defined medium that does not contain insulin (Upper Panel). Adenohypophyseal placode differentiation requires Shh treatment from days ~4-8 and during floating culture. Olfactory placode differentiation requires additional FGF treatment between days ~4-8. Lens placode differentiation requires Wnt inhibition during days 4-8 and BMP treatment during floating culture. Trigeminal placode differentiation requires Wnt activation and PDGF treatment between days ~4-8. Epibranchial and otic placode derivation requires a base medium of GMEM and 1.5% KSR (Lower Panel). Epibranchial placode derivation requires an increased dosage of FGF during days 4-8 and BMP treatment during floating culture. Otic placode derivation requires the general treatment.
Figure 26:
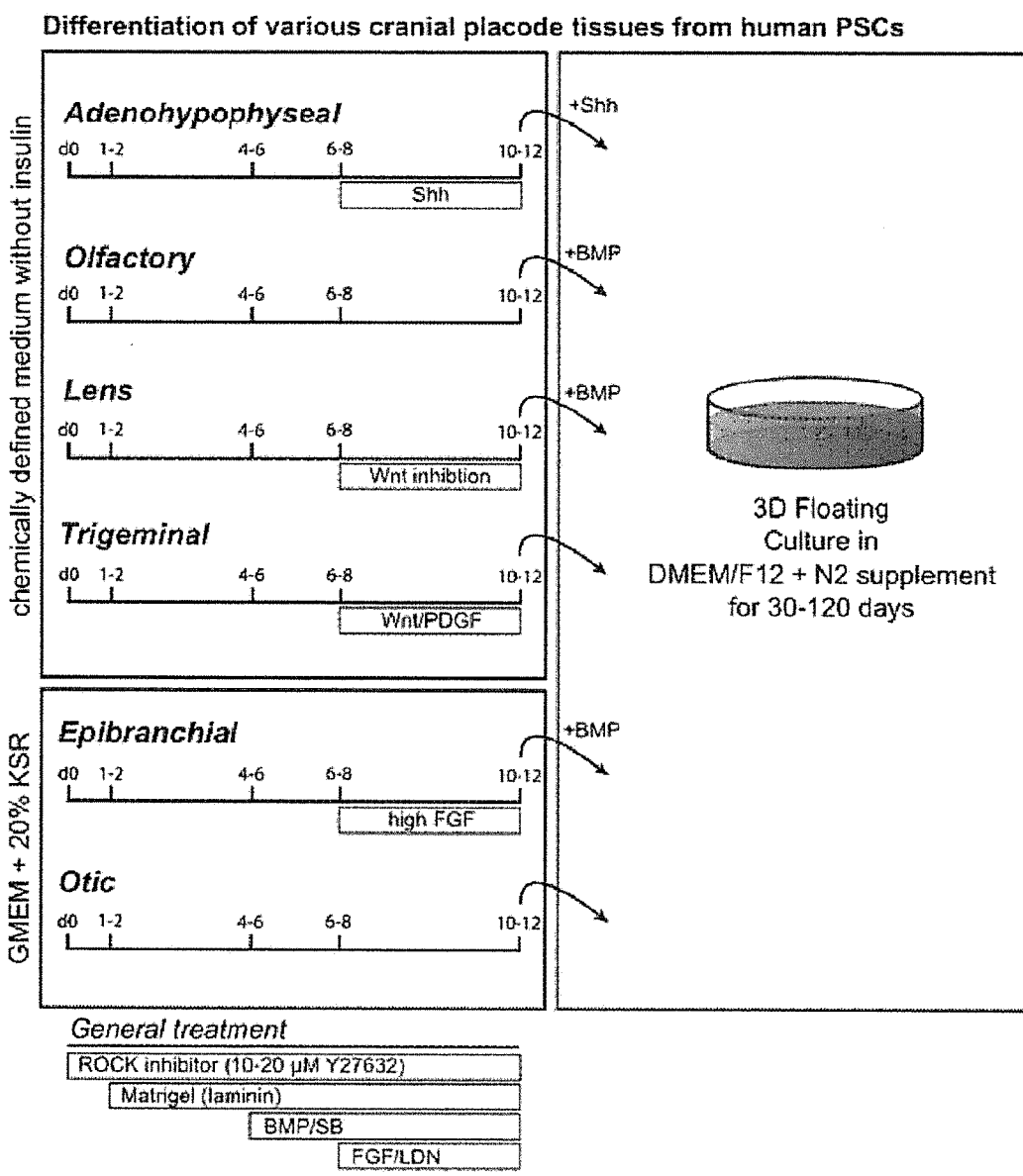
FIG. 26 shows a schematic illustration of exemplary, non-limiting embodiments for deriving cranial placode tissue from human PSCs. Sequential treatment of EBs with BMP/SB-FGF/LDN is used for derivation of each placode, although base media are different in some cases. All derivation methods also require the transfer of day 10-12 aggregates into a floating culture in N2 Medium for long-term differentiation (Left Panel). Adenohypophyseal, olfactory, lens and trigeminal placode derivation requires the use of a growth factor-free chemically defined medium that does not contain insulin (Upper Panel). Adenohypophyseal placode differentiation requires Shh treatment from days ~6-12 and during floating culture. Olfactory placode differentiation requires additional FGF treatment between days ~6-12. Lens placode differentiation requires Wnt inhibition during days ~6-12 and BMP treatment during floating culture. Trigeminal placode differentiation requires Wnt activation and PDGF treatment between days ~6-12. Epibranchial and otic placode derivation requires a base medium of GMEM and 20% KSR (Lower Panel). Epibranchial placode derivation requires an increased dosage of FGF during days 6-12 and BMP treatment during floating culture. Otic placode derivation requires the general treatment.

In other embodiments of the methods described herein, non-otic placodes by providing alternative media conditions or combinations of morphogens and signaling modulators, as described below and illustrated schematically for exemplary embodiments starting from mPSCs (FIG. 25) or hPSCs (FIG. 26).

In some embodiments, epibranchial placode tissue is generated by obtaining preplacodal ectoderm from pluripotent stem cells by the methods described herein, and using subsequent culture conditions similar to those used to derive otic placode, but with increased concentration of an exogenous FGF, e.g., FGF2, between days 4-8 for mouse and days 6-12 for human relative to the concentration used for otic placode derivation. In some embodiments, the FGF concentration to be used is about 30 ng/ml to about 100 ng/ml, e.g., 40 ng/mL, 50 ng/mL, 60 ng/ml, 70 ng/ml, 85 ng/ml, 90 ng/ml, or another FGF concentration from about 30 ng/ml to about 100 ng/ml. Epibranchial placodes can be identified by their expression of Ecad, Pax8 and Sox3 in mouse and human. Morphologically, epibranchial placodes are characterized by thickened epithelial patches and do not develop into a vesicles like the otic placode. In addition, epibranchial placodes are neurogenic. Thus, the development of epibranchial episodes is also characterized by the presence of Islet1/βIII-tubulin+ neuroblasts developing within or directly adjacent to the Pax8/Sox3/Ecad+ epithelium. In other embodiments, where placodes anterior to the otic and epibranchial placodes are to be obtained from PSCs and anterior preplacodal ectodermthe medium used for differentiation starting from PSCs is "growth-factor-free chemically defined medium" (gfCDM). gfCDM consists of a 1:1 mixture of Iscove's Modified Delbecco's Medium and Ham's F12 (both containing Glutamine or Glutamax), 1× chemically defined lipid concentrate, penicillin/streptomycin or equivalent antibiotic, 450 µM monothioglycerol, 5 mg/mL purified bovine serum albumin and 15 µg/mL apotransferrin or equivalent iron chelator (Wataya et al., (2008), Proc. Natl. Acad. Sci. USA, 105(33):11796-11801). Accordingly, in the following embodiments, the above-defined "Differentiation Medium" containing GMEM and KSR is replaced with gfCDM or an equivalent medium. All embodiments require BMP/SB-FGF/LDN treatment.

Anterior preplacodal ectoderm specification can be determined by assaying expression of Otx2, Pax6, and Ecad.

In some embodiments, adenohypopheseal placode tissue is to be generated. The method follows along the lines described for generation of preplacodal ectoderm for differentiation into otic placode, i.e., in the timed-presence of BMP/SB-FGF/LDN. However, the medium used is gfCDM. In addition, a Shh agonist (e.g., Purmorphamine, smoothened agonist (SAG), Shh protein, etc.) between days 4-12. Anterior preplacodal specification can be determined by expression of Otx2, Pax6 and Ecad. Adenohypopheseal tissue can be identified by detecting the presence of Ecad, Pitx1/2 and/or Lim3 expression or, morphologically, by vesicle formation.

In other embodiments, olfactory placode is to be obtained: Again, starting from PSCs, the method comprises culture of PSC-derived EBs in gfCDM medium and sequential treatment with BMP/SB and FGF/LDN cell aggregates cultured in gfCDM, where FGF treatment continues past preplacodal specification and throughout the floating culture differentiation of preplacodal ectoderm to olfactory placode. In some embodiments, FGF8 is also included, or replaces FGF2. Additional or alternative FGF proteins may be necessary for olfactory specification such as FGF-8 (e.g. 0.5-50 ng/mL). Olfactory tissue can be identified by Ecad and Dlx5/6 expression, and morphologically by the presence of Islet1/βIII-tubulin+ neuroblasts developing within or directly adjacent to the Dlx5/6/Ecad+ epithelium.

In some embodiments, where lens placode is to be derived, the differentiation method comprises treatment of BMP/SB-FGF/LDN with a reduced concentration of FGF (e.g. 0.5-15 ng/mL) cell aggregates cultured in gfCDM with an inhibitor of Wnt/β-catenin signaling (e.g., XAV939) between days 4-8 (mouse) or around days 6 through 12 (human). In some embodiments, an increased concentration of BMP4 of BMP7 and/or modulation of the BMP inhibitor concentration may be necessary during days 4-12 (mouse) or around days 6 through 20 (human) to allow partial to complete activation of the BMP pathway. In some embodiments, low concentrations of FGF (0.1-15 ng/mL) should be used because FGF can inhibit lens development. Lens tissue can be distinguished by expression of FoxE3 or alpha-, beta-, or gamma-crystallin. Lens placodes are also characterized morphologically by the formation of vesicles.

In other embodiments, where an intermediate placode, e.g., a trigeminal placode, is to be derived from PSCs, GMEM+KSR or gfCDM media are used to specify intermediate preplacodal ectoderm.

In some embodiments, trigeminal placode tissue is obtained by treating BMP/SB-FGF/LDN cell aggregates with an activator of Wnt/β-catenin signaling and platelet-derived growth factor (PDGF) between days 4-8 (mouse) or days 6-12 (human). Intermediate preplacodal ectoderm and trigeminal specification can be identified by expression of Pax3 and Ecad in a thickened epithelium. Alternatively, trigeminal tissue is identified by the presence of Islet1/βIII-tubulin+ neuroblasts developing within or directly adjacent to the Pax3/Ecad+ epithelium.

Screening Methods

Also provided herein are screening methods for identifying an agent that induces or enhances differentiation into a particular placode (e.g., otic placode), or a particular cell type, e.g., inner ear sensory cells.

In some embodiments, the screening method is a method for identifying an agent that induces or enhances the differentiation of preplacodal ectoderm to hair cells (e.g. inner ear sensory hair cells), where the method includes the steps of (i) providing a floating culture comprising preplacodal ectoderm, which can be obtained from pluripotent stem cells (e.g., human PSCs) as described herein; (ii) contacting the floating culture with a test agent; (iii) assessing expression of hair cell markers, e.g., Myosin 7a, Brn3C, or Atoh1; and (iv) indicating that the test agent is an agent that induces or enhances preplacodal ectoderm to hair cell differentiation in vitro, if expression of Myosin 7a, Brn3C, or Atoh1 in the presence of the test agent is higher in the presence of the test agent that in the absence of the test agent.

In some embodiments, expression of Myosin 7a, Brn3C, or Atoh1 are assessed indirectly by use of a pluripotent stem cell-derived reporter lines for any of the foregoing genes. For example, a reporter line may be a human PSC line comprising a knock-in of a gene encoding a fluorescent reporter protein (e.g., EGFP) within the endogenous locus of Myosin 7a. Alternatively, reporter lines may be transgenic reporter lines harboring a heterologous construct comprising a promoter fragment of a marker gene (e.g., Myosin 7a) fused to a fluorescent reporter gene). Use of reporter lines allows the convenient detection of relevant marker genes in live cells over time and is particularly suitable for assessing the effects of many test agents in parallel, e.g., in a multiwell format (e.g., 96, or 384 well format). Methods for generating reporter lines, and for high content-imaging-based fluorescent reporter assays and screens in living cells are well known in the art. See, e.g., Liu et al (2011), *Methods Mol Biol.*, 767:355-367; and Xia et al (2012), *Stem Cells*, 30(9): 1800-1807.

In other embodiments, a screening method is directed to identifying an agent that protects hair cells from a toxic compound (e.g., an aminoglycoside antibiotic or cisplatin) toxicity is included herein. The method includes the steps of (i) providing a cell culture comprising sensory hair cells; (ii) contacting the cultured sensory hair cells with a cytotoxic agent in the presence of a test agent; (iii) quantifying the presence of one or more markers of cell death in the contacted sensory hair cells; and (iv) indicating that the test agent is cytoprotective if the level of the one or more markers of cell death in the presence of the test agent and the cytotoxic agent are lower than in the presence of the cytotoxic agent in the absence of the test agent. In some embodiments, the cell death marker is activation of Caspase 3 or Caspase 8.

III. Compositions

Also described herein are compositions relating to isolated inner hair sensory cell populations, isolated intermediate cell populations and cell cultures useful for obtaining inner hair cell populations, and compositions useful for differentiation of pluripotent stem cells into inner ear sensory hair cells and relevant intermediate cell types, e.g., preplacodal ectoderm cells. Also contemplated are non-otic placodal tissues, e.g., lens placode, trigeminal placode, epibranchial placode, derived from preplacodal ectoderm according to the methods described herein In some embodiments described herein is a composition that can be used to initiate differentiation of EBs into non-neural ectoderm, a key step in generating inner ear sensory hair cells according to the provided differentiation methods. Such compositions contain at a minimum a combination of BMP2, BMP4, or BMP7, and a TGFβ inhibitor. In some cases, the BMP in the composition is BMP4.

In some embodiments, the concentration of BMP4 in the composition can range from at least about 1 ng/ml to about 50 ng/ml, e.g., about 2 ng/ml, 4 ng/ml, 5 ng/ml, 7 ng/ml, 12 ng/ml, 15 ng/ml, 20 ng/ml, 25 ng/ml, 32 ng/ml, 40 ng/ml, or another concentration of BMP4 from at least about 1 ng/ml to about 50 ng/ml.

In some embodiments, the TGFβ inhibitor used in the just-mentioned composition is SB 431542 (CAS No. 301836-41-9, at a final concentration of about 1 μM). Alternatively, any of the following TGFβ inhibitors may be used: A 83-01 (CAS No. 909910-43-6), GW 788388 (CAS No. 452342-67-5), LY 364947 (CAS No. 396129-53-6), RepSox (CAS No. 446859-33-2), SB 505124 (CAS No. 694433-59-5), SB 525334 (CAS No. 356559-20-1), or SD 208 (CAS No. 356559-20-1) at a final working concentration of about 0.05 μM to about 5 μM. In other embodiments, the concentration of the TGFβ inhibitor in the composition is about 2 fold the $IC_{50}$ concentration of the selected TGFβ inhibitor for the TGFβ receptor subtype to be inhibited to about 50 fold the $IC_{50}$ concentration of the selected TGFβ concentration. In some embodiments, the composition contains BMP4 at a concentration of 10 ng/ml and SB 431542 at a final working concentration of about 1 μM.

Other compositions presented herein are useful for differentiating non-neural ectoderm cells into preplacodal ectoderm. Such compositions contain at least an FGF and a BMP inhibitor.

In some embodiments, the FGF used in the composition is selected from any of FGFs 1-23, or a combination thereof. In some embodiments the FGF in the composition is FGF2, FGF3, FGF10, FGF19, FGF20 or a combination thereof. In some embodiments, the included FGF used is FGF2.

A suitable working FGF concentration ranges from at least about 10 ng/ml to about 100 ng/ml, e.g., 15 ng/ml, 20 ng/ml, 25 ng/ml, 30 ng/ml, 40 ng/ml, 50 ng/ml, 65 ng/ml, 75 ng/ml, or another concentration of an FGF from at least about 10 ng/ml to about 100 ng/ml. One of ordinary skill in the art will appreciate that some FGFs are less stable than others under culture conditions, and so the concentration of FGF should be adjusted up or down accordingly. In some embodiments, the FGF is FGF2 and the concentration of in the composition is about 25 ng/ml.

In some embodiments, the BMP inhibitor is LDN-193189 (CAS No. 1062368-24-4). Alternatively, DMH1 (CAS No. 1206711-16-1) or Dorsomorphin (CAS No. LDN-193189) are included in the just-mentioned composition. In some embodiments a suitable working concentration of the BMP inhibitor in the composition ranges from at least 20 nM to about 500 nM, e.g., 30 nM, 50 nM, 60 nM, 80 nM, 100 nM, 125 nM, 150 nM, 200 nM, 300 nM, 400 nM or another working concentration from about 20 nM to about 500 nM. In some embodiments, the BMP inhibitor in the composition is LDN-193189 at a working concentration of about 100 nM.

In some embodiments, the composition for differentiation of non-neural ectoderm into preplacodal ectoderm contains FGF2 and LDN-193189. In one embodiment, such a composition contains FGF2 at a concentration of about 25 ng/ml and LDN-193189 at a concentration of about 100 nM.

Also provided are kits useful for the differentiation of pluripotent stem cells into inner ear sensory hair cells or their precursors according to the differentiation methods provided herein. In some embodiments such a kit includes (i) BMP4 and a TGFβ inhibitor; or (ii) an FGF (e.g., FGF2) and a BMP inhibitor. In some embodiments, the kit includes BMP4, a TGFβ inhibitor, an FGF, and a BMP inhibitor. In one embodiment, the kit includes BMP4, SB 431542, FGF2, and LDN-193189, and instructions for their use to differentiate mouse or human pluripotent stem cells according to the methods presented herein.

In some embodiments, the above-described compositions for differentiation may be provided as concentrated supplements for dilution to a final/working concentration. For example, the compositions may be provided as a 50×, 25×, 10×, 6×, or 2× final/working concentration supplement to be diluted in culture medium prior to initiating a differentiation method as described herein.

In some embodiments, any of the above-described compositions for differentiation further include a culture medium in accordance with the differentiation methods described herein.

Also described herein is a cell culture comprising a cell culture medium, e.g., a "differentiation medium" as used in the methods described herein, BMP4, and embryoid bodies (EBs). In some embodiments, the EBs in the just-mentioned composition are mouse EBs. In other embodiments, the EBs are human EBs. Such cell cultures allow the efficient generation of non-neural ectoderm and preplacodal ectoderm, key precursor tissues for the generation of inner ear sensory hair cells as described herein.

Further described herein is a differentiated EB obtained by the methods described herein, wherein the differentiated EB is characterized by an E-cadherin$^+$ outer layer, a Sox1$^+$/NCAD$^+$ intermediate layer, and a NANOG$^+$ inner core.

Also provided herein is a cell culture that includes a cell culture medium, e.g., a "differentiation medium" as described herein, an exogenous FGF, a BMP inhibitor and a cell population comprising non-neural ectoderm cells. Such a composition is used to advance the differentiation of non-neural ectoderm cells into preplacodal ectodermcells, which later give rise to otic progenitors and inner ear sensory hair cells. Preplacodal ectoderm cells are characterized by a pattern of expression markers including the expression of the non-neural ectoderm marker AP2, Dlx3, and the absence of the mesendodermal marker brachyury or the neuroectodermal marker N-cadherin (Ncad).

Also provided herein is an isolated otic progenitor population comprising a cell population characterized by expression of Sox2, Jag1, Pax2, Pax8, E-cadherin.

As described herein, the provided differentiation methods can be used to obtain an isolated cell population comprising inner ear sensory hair cells. In some embodiments, the inner ear sensory hair cells are primarily Type II vestibular hair cells.

Inner ear sensory hair cells are characterized by expression of Myosin 7a Brn3c, or expression of Atoh1. In some embodiments, the inner ear sensory hair cells of the isolated population exhibit rapid uptake of the fluorescent dye FM 1-43, outwardly rectifying potassium currents, and mechanotransduction currents.

In some embodiments, the isolated cell population comprises at least about 10% to about 90% inner ear sensory hair cells, e.g., about 15%, 20%, 25%, 30%, 33%, 40%, 50%, 60%, 75%, 80%, 90%, or another percent of inner ear sensory hair cells in the isolated cell population from at least about 10% to about 90% of cells in the isolated cell population.

Methods for characterizing expression of cell type markers are well established in the art, and include, but are not limited to: immunocytochemistry, flow cytometry, RT-PCR, and immunoblotting to assess expression of the marker genes and proteins mentioned herein.

EXAMPLES

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

Example 1 Generation of Pre-Placodal Ectoderm from mES Cells

Signaling Molecules and Recombinant Proteins.

The following small molecules and recombinant proteins were used: recombinant human BMP4 (10 ng/mL; Stemgent), human FGF2 (25 ng/mL; Peprotech), XAV939 (1 µM; Santa Cruz), SU5402 (10 µM; BioVision), SB-431542 (1 µM; Tocris Bioscience), and LDN-193189 (100 nM; Stemgent). Notably, we have obtained comparable results using concentrations of up to 1 µM LDN-193189.

Quantitative PCR.

RNA was isolated using the RNeasy Minikit (Qiagen) and treated with TURBO DNase (Ambion). Single-stranded cDNA was synthesized using Omniscript reverse transcriptase (Qiagen) and Oligo-dT primers. All amplicons had standardized sizes of 100-110 bps. cDNA samples were amplified on an ABI PRISM 7900HT Sequence Detection System (Applied Biosystems) using the SYBR Green PCR Master Mix (Applied Biosystems). For each PCR reaction, a mixture containing cDNA template (5 ng), Master Mix, and forward and reverse primers (400 nM each) was treated with uracil N-glycosylase at 50° C. for 2 min before undergoing the following program: 1 cycles, 95° C., 10 min; 45 cycles, 95° C., 15 sec, 60° C., 1 min; 1 cycles, 95° C., 15 sec, 60° C., 15 sec, 95° C., 15 sec; 72° C., hold. Melting curve analysis was performed to confirm the authenticity of the PCR product. The mRNA level for each gene was calculated relative to L27 mRNA expression.

```
Primers used: DIx3,
Forward-
                                    (SEQ ID NO: 1)
CAGTACGGAGCGTACCGGGA,
```

```
                                                    -continued
Reverse-
                                                 (SEQ ID NO: 2)
TGCCGTTCACCATGCGAACC;

Sox1,
Forward-
                                                 (SEQ ID NO: 3)
AACCAGGATCGGGTCAAG, Reverse-
                                                 (SEQ ID NO: 4)
ATCTCCGAGTTGTGCATCTT;

brachyury,
Forward-
                                                 (SEQ ID NO: 5)
CACACGGCTGTGAGAGGTACCC, Reverse-
                                                 (SEQ ID NO: 6)
TGTCCGCATAGGTTGGAGAGCTC;

Reverse-
                                                 (SEQ ID NO: 7)
GGGAAGGTGAAGAGATGAGG;

Pax8,
Forward-
                                                 (SEQ ID NO: 8)
CGGCGATGCCTCACAACTCG, Reverse-
                                                 (SEQ ID NO: 9)
TGGGCCAAGTCCACAATGCG;

Pax2,
Forward-
                                                 (SEQ ID NO: 10)
CCCGTTGTGACCGGTCGTGATAT, Reverse-
                                                 (SEQ ID NO: 11)
TGGGTTGCCTGAGAACTCGCTC.
```

Immunohistochemistry.

Aggregates were fixed with 4% paraformaldehyde. The fixed specimens were cryoprotected with a graded treatment of 10, 20 and 30% sucrose and then embedded in tissue freezing medium. Frozen tissue blocks were sectioned into 10 or 12 µm cyrosections. For immunostaining, a 3% Goat or Horse Serum and 0.1% Triton-X100 solution was used for primary antibody incubation. An Alexa Fluor 488 conjugated anti-mouse IgG or anti-rat IgG and an Alexa Fluor 568 conjugated anti-rabbit IgG (Invitrogen) were used as secondary antibodies. A DAPI counterstain was used to visualize cellular nuclei (Vector, VectaShield). For whole-mount staining, aggregates were placed directly into blocking solution with 1% Triton-X100 following fixation. For confocal imaging and 3D reconstruction experiments, following secondary antibody incubation, aggregates were cleared using ScaleA2 solution for 1-2 days followed by ScaleB4 treatment for another 2 days as described previously[34]. Microscopy was performed on a Nikon TE2000 Inverted Microscope or an Olympus FV1000-MPE Confocal/Multiphoton Microscope. 3D reconstruction was performed using Voxx (custom software developed by Indiana Center for Biological Microscopy).

The following antibodies were used: anti-E-cadherin (rabbit, Abcam; mouse, BD Biosciences); anti-N-cadherin (mouse, BD Bioscience); anti-Sox1 (rabbit, Cell Signaling Technologies); anti-Nanog (rabbit, Abcam); anti-brachyury (goat, Santa Cruz Biotechnology); anti-AP2a (mouse, DHSB); anti-Pax8 (rabbit, Abcam); anti-Pax2 (rabbit, Invitrogen; mouse, Abnova); anti-Sox2 (mouse, BD Biosciences); anti-Jag1 (rabbit, LSBio); anti-p27$^{kiP1}$ (mouse, BD Biosciences); anti-myosinVIIa (rabbit, Proteus); anti-acetylated-α-Tubulin (mouse, Abcam); anti-TuJ1 (mouse, Covance); anti-Calretinin (mouse, Millipore); anti-Caspr1 (mouse, NeuroMAB); anti-Caspr2 (mouse, NeuroMAB); anti-p63 (mouse, Santa Cruz Biotechnology); anti-Cytokeratin-5 (rabbit, Sigma); anti-Neurofilament (rabbit, Millipore); anti-Brn3c (mouse, Millipore); anti-Islet1 (mouse, DSHB); anti-Synaptophysin (rabbit, Invitrogen); anti-Brn3c (mouse, Santa Cruz Biotechnology); anti-CtBP1 and anti-CtBP2 (mouse, BD Biosciences); anti-Rab3 (mouse, BD Biosciences); anti-SNAP25 (mouse, BD Biosciences); anti-Pax6 (rabbit, Abcam); anti-Pax3 (mouse, DSHB); anti-aPKC (rabbit, Santa Cruz Biotechnology); anti-laminin-B1 (rat, Abcam). For most antibodies, mouse embryonic tissue sections were used as positive controls. Mouse embryos were dissected from time pregnant ICR mice using a protocol approved by the Institutional Animal Care and Use Committee at Indiana University School of Medicine. The embryo fixation and processing procedure was identical to that used for cell aggregates.

For Alcian blue staining, cryosections were incubated in Alcian blue staining solution for 10 minutes and subsequently de-stained using 60% ethanol/40% acetic acid for 20 minutes. A final eosin stain was performed for 30 seconds. For Oil Red O staining, cryosections were kept in 60% isopropanol for 2 minutes and then placed in freshly prepared Oil Red 0 stain for 5 minutes followed by a 30 second hematoxyline stain.

Image Analysis.

The percentage of epithelial cells expressing Pax8/Ecad was established by analyzing serial sections of day 6 and 8 aggregates. Data are representative of 6-8 aggregates from at least 3 separate experiments. For analysis of each aggregate, 5 cryosections were chosen at random positions along the z-axis of the aggregate. Using Nikon Elements or NIH ImageJ software, the Ecad$^+$ outer-epithelium was outlined and cell counting of DAPI and Pax8$^+$ nuclei along the length of the epithelium established a percentage for each cryosection.

The apparent thickness of epithelia was determined by analyzing cryosections stained with Ncad (Control) or Ecad antibodies (all other conditions) on days 3-6. Data are representative of 6-8 aggregates from at least 3 separate experiments. For each aggregate, 3 serial sections were analyzed. Five points along the epithelium were randomly chosen and the thickness was measured using Nikon Elements image analysis tools.

Similarly, the number of Myo7a$^+$ hair cells in each day 20 aggregate was determined by analyzing 10 µm serial cryosections. Each biological sample represents the average number of hair cells counted in 4-6 cell aggregates and data are representative of the average from 3 separate experiments (15 aggregates total for each condition). Odd and even numbered cryosections were analyzed separately and averaged to avoid double counting. The number of vesicles was quantified similarly, but every third section was analyzed to avoid double counting and allow for analysis of three separate staining combinations. Vesicles with a long axis diameter larger than 30 µm were accounted for to avoid double counting.

Figure 3:
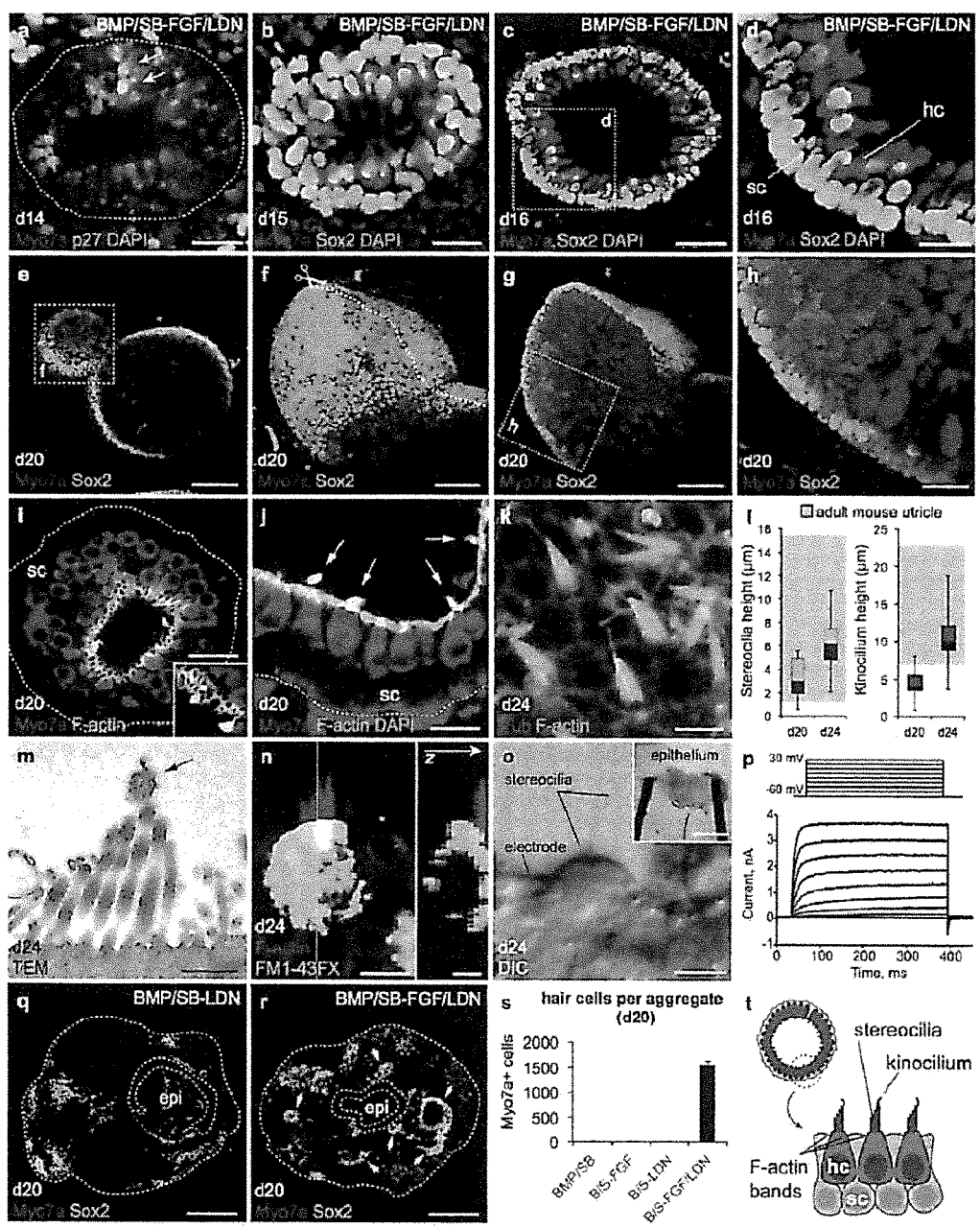
FIG. 3 shows stem cell-derived otic vesicles generate functional inner ear hair cells with stereocilia bundles and kinocilium. a, Myo7a/$p27^{kiP1+}$ hair cell-like cells on day 14. b-d, Myo7a/$Sox2^+$ hair cells (hc) with underlying $Sox2^+$ supporting cells (sc) on day 15 (b) and 16 (c, d). e-h, Whole-mount immunofluorescence for Myo7a and Sox2 (e) and 3D reconstruction (f-h) of a vesicle in a day 20 BMP/SB-FGF/LDN aggregate. i-k, F-actin (F-act) labels cell-cell junctions on the luminal surface and stereocilia bundles. k, Acetylated-α-Tubulin (Tublin) labels kinocilium and the cuticular plate. l, Distribution of stereocilia and kinocilium heights on days 20 and 24 compared to adult mouse utricle hair cells, range indicated by gray boxes (n>100 cells; ±max/min). m, Transmission electron micrograph of stereocilia bundles and kinocilium (arrow). n, Representative hair cell following 1 min FM1-43FX incubation, fixation and staining for F-actin. o, Representative epithelium preparation (inset) and hair cell during electrophysiological recordings. p, Representative voltage-current responses recorded from hair cells. The voltage protocol is shown at the top. q, r, Only BMP/SB-FGF/LDN aggregates contain Myo7a/$Sox2^+$ vesicles. epi, epidermis-like inner-epithelium (dashed outline). s, Number of hair cells on day 20 (n=12-16; mean±s.e.m.) t, Vesicles display the hallmarks of inner ear sensory epithelia. Scale bars, 250 µm (e, q, r, o-inset) 100 µm (f, g), 50 µm (c, f, g), 25 µm (a, b, d, h, i, j), 10 µm (o), 5 µm (n, k), 250 nm (m).

Stereocilia heights were determined by measuring the apparent length of F-actin labeled structures protruding from Myo7a$^+$ hair cells on day 20 and 24. Likewise, kinocilium heights were determined by measuring the apparent length of acetylated-α-Tubulin labeled protrusions from Myo7a$^+$ hair cells. Regions of interest were chosen randomly for analysis and over 100 cells were analyzed across 3-5 separate epithelia for the data shown in FIG. 3.

Synapses were quantified by analyzing day 16, 20 and 24 aggregate sections stained for synaptophysin and CtBP2/Ribeye using a previously described method[36]. Regions of interest were chosen randomly for analysis and more than 100 cells were analyzed across 4-5 separate epithelia from 3 separate experiments for the data shown in FIG. 3. Confocal z-stacks were taken of CtBP2-stained hair cells. The max-intensity projections were used to count the number of CtBP2+ puncta surrounding each hair cell nucleus.

Statistical Analysis.

Statistical significance was determined using a Student's t-test for comparison of two groups or a One-Way ANOVA followed by Tukey's post-hoc test for multiple comparisons, unless stated otherwise. All data were analyzed using Prism 6 or Microsoft Excel software.

FM1-43 Labeling.

The presence of functional mechanosensitive channels was confirmed using a FM1-43 dye uptake assay similar to previous studies[24,37,38]. Large lumen aggregates (i.e. >500 μm long-axis diameter), identified by their translucency and spherical morphology relative to surrounding tissue, were used for these experiments. Aggregates were incubated in DMEM-F12 containing FM1-43FX (5 μM; Invitrogen) for 1 minute and then washed 3× in fresh N2 Medium. A faint cellular outline caused by autofluorescence was used to identify potential hair cells in the vesicle wall. In N2 Medium, a 0.25 μm tungsten needle was used to puncture each vesicle in an area away from the site of potential hair cells. The punctured vesicles were incubated in DMEM-F12 containing FM1-43FX (5 μM) for 1 minute with gentle rocking and then washed 3× in fresh N2 Medium. Vesicles were imaged to confirm dye uptake and immediately fixed with 4% paraformaldehyde. For some experiments, epithelia were fixed and incubated in PBS containing 1% Triton-X100 and phalloidin conjugated to Alexa Fluor 647 (Invitrogen) to confirm the identity of hair cells.

Electrophysiological Recordings.

On day 24 of differentiation, large lumen vesicles (>500 μm diameter) were dissected from cell aggregates following a 30-minute incubation in DMEM/F12 containing Dispase (STEMCELL Technologies). Epithelial regions containing hair cells were identified based on a thickened morphology relative to the rest of the vesicle epithelium. Two incisions were made using tungsten needles on the opposite side of the vesicle in order to expose and flatten the hair cell-containing epithelium. The flattened epithelium was mounted onto round glass coverslip and held in position by two wires glued to the coverslip using MDX4-4210 (Corning). The coverslip was then placed in a submersion-type slice chamber mounted on the stage of a Nikon E600FN Eclipse microscope. Electrophysiological recordings were performed under continuous perfusion of oxygenated artificial cerebrospinal fluid (ACSF) that contained the following (in mM): 130 NaCl, 3.5 KCl, 1.1 $KH_2PO_4$, 1.3 $MgCl_2$, 2.5 $CaCl_2$, 30 $NaHCO_3$, 10 glucose, pH 7.4 (320 mOsm/kg). Recording pipettes were pulled from borosilicate capillary glass (WPI) with resistances ranging from 2 to 3 MO. Recording pipettes were filled with a potassium gluconate based recording solution that contained the following (in mM): 130 K-Gluconate, 3 KCl, 3 $MgCl_2$, 5 phosphocreatine, 2 K-ATP, 0.2 NaGTP, 10 HEPES, pH 7.3, 290 mOsm/kg. Whole-cell access resistances were monitored throughout each experiment and ranged from 5-20 MO; a change of 15% was deemed acceptable.

Hair cells were identified with a 40× water-immersion objective and differential interference contrast (DIC). Only cells with hair bundles on their apical surface were chosen for recording. Positive pressure was maintained as the recording pipette was lowered into the epithelium. When the recording pipette touched the membrane, positive pressure was released and tight seal was formed. Recordings were obtained at 30° C. using solution inline heater (Warner Instruments). The cells were held at −60 mV, and data were acquired using whole-cell technique in voltage-clamp mode using a Multiclamp 700B amplifier (Molecular Devices) coupled to a Digidata 1332A board (Molecular Devices). The data were analyzed using the pClamp 10.2 (Molecular Devices). All chemicals were purchased from Sigma-Aldrich.

Transmission Electron Microscopy.

Day 24 aggregates were fixed in 2% Paraformaldehyde/ 2% Glutaraldehyde in 0.1M phosphate buffer. After fixation the specimens were rinsed with phosphate buffered saline (PBS) followed by post-fixation with 1% osmium tetroxide. Thereafter, the aggregates were dehydrated through a series of graded ethyl alcohols and embedded in Embed 812 (Electron Microscopy Sciences). Ultra-thin sections (70-80 nm) were cut, stained with uranyl acetate and viewed on a Tecnai BioTwin (FEI) transmission electron microscope at 80 kV. Digital images were taken with an Advanced Microscope Techniques CCD camera.

Western Blot Analysis.

Cell aggregates were lysed in RIPA buffer supplemented with a protease inhibitor cocktail (Roche). Cell extracts were centrifuged at 13,000 rpm, 4° C. for 10 minutes to remove insoluble debris and chromosomal DNA. Proteins were separated by denaturing polyacrylamide gel electrophoresis (SDS-PAGE) and transferred to PVDF membranes (Biorad). After blocking, membranes were incubated with a primary antibody overnight at 4° C. An anti-β-actin (Sigma) antibody was used for confirmation of equal loading of the samples. Blots were detected with an HRP-conjugated goat anti-rabbit or rabbit anti-mouse antibody (Invitrogen) and visualized with the SuperSignal West Pico or -Femto chemiluminescent detection system (Pierce) and exposed to x-ray film.

Figure 5:
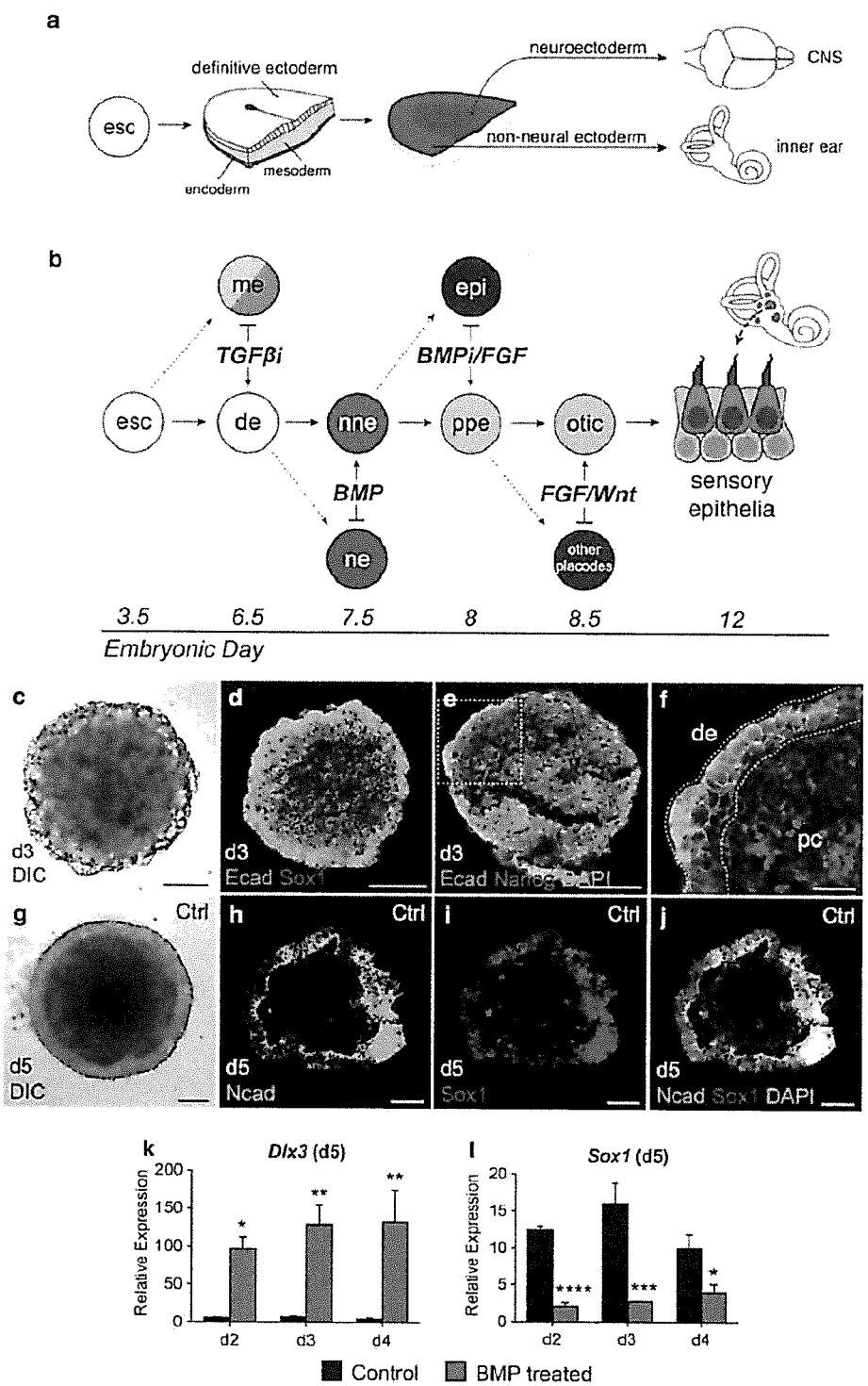
FIG. 5 shows inner ear development from the definitive ectoderm. a, The cell fate decision between non-neural ectoderm and neuroectoderm is the critical point of departure between central nervous system and inner ear development. b, The key cell fate decisions and inductive cues during inner ear development in vivo and in our in vitro culture system. Here "otic" refers specifically to prosensory cells found in the otic placode/vesicle that give rise to sensory epithelia containing hair cells and supporting cells. "Other placodes" refers to the adenohypophyseal, olfactory, lens, trigeminal, and epibranchial placodes, which are derived from more anteriorly located regions of the preplacodal ectoderm. c-f, On day 3 of SFEBq differentiation, a Nanog/Sox1- and Ecad+ epithelium forms on the outer surface of each aggregate. SFEBq has been shown to generate a nearly pure population of neuroectodermal cells (see Eiraku et al. 2008, 2011 and Kamiya et al. 2011); therefore, this epithelium may be roughly equivalent to embryonic definitive ectoderm because it is in-between a state of pluripotency (Nanog+) and neuroectoderm (Sox1/Ncad+)4-6. To our knowledge, however, no unique markers of the definitive ectoderm are known. esc, embryonic stem cells; me, mesendoderm; de, definitive ectoderm; nne, non-neural ectoderm; ne, neuroectoderm; ppe, preplacodal ectoderm; epi, epidermis; otic, otic placode; pc, pluripotent cell. g-j, By day 5 of differentiation, vehicle control (Ctrl) aggregates develop a Ncad/Sox1$^+$ epithelium similar to the neuroectoderm in vivo and previous reports using SFEBq culture (see Eiraku et al. 2008, 2011 and Kamiya et al. 2011)4-6. k-l, qPCR analysis of day 5 samples after the addition of 10 ng/mL BMP or a vehicle control to the medium on day 2, 3 and 4. The nonneural ectoderm and mesendodermal markers Dlx3 was upregulated in response to BMP4 treatment, whereas the neuroectodermal marker Sox1 was downregulated (n=3; mean±s.e.m.). A two-way ANOVA with Bonferroni's post hoc test for multiple comparisons was used to determine significance (*$P<0.05$, $P<0.01$, *$P<0.001$, ****$P<0.0001$). No significant differences were observed between control groups. Scale bars, 100 µm (c-e), 25 µm (f).

During neurulation in vivo, the definitive ectoderm is subdivided into the neuroectoderm and non-neural ectoderm, the latter of which gives rise to the inner ear (FIG. 5a). Recent studies have demonstrated how organogenesis of complex neuroectoderm tissues such as the cerebral cortex and retina can be faithfully reconstituted in vitro by culturing ESCs as a floating aggregate in serum-free media (also known as SFEBq culture)[12,14,15]. Since the inner ear shares a common precursor with these tissues, the definitive ectoderm, we proposed that SFEBq culture could be redirected to generate inner ear epithelia using carefully timed morphogenetic cues (FIG. 1a and FIG. 5b). Led by previous studies, we identified a definitive ectoderm-like epithelium on day 3 of SFEBq culture, prior to expression of neuroectoderm-associated proteins on day 5 (FIG. 5c-j). During early embryogenesis, activation of bone morphogenetic protein (BMP) signaling is critical for induction of the non-neural ectoderm from the definitive ectoderm epithelium[11,17]. Consistent with this role, in aggregates treated with BMP4 (hereafter, BMP), the non-neural ectoderm marker Dlx3 was upregulated, while the neuroectoderm marker Sox1 was downregulated (FIG. 5k, l). Yet BMP-treated aggregates also expressed the mesendoderm marker brachyury, indicating the undesirable induction of mesoderm or endoderm cell types (FIG. 1b)[18]. By day 5, 60.8±3.9% of cells in BMP-treated aggregates were brachyury+ and the presumptive ectodermal layer on the surface of each aggregate had been disrupted, prohibiting further analysis (FIG. 1c, d, f, g and FIG. 6b). To suppress aberrant mesendoderm induction, we combined BMP treatment with the transforming growth factor β (TGFβ) inhibitor SB-431542 (hereafter, SB; FIG. 1a). A combined treatment of SB and BMP (hereafter, BMP/SB) on day 3 completely abolished brachyury+ cells in the outer-epithelium, while maintaining mesendoderm tissue in the inner layer of the aggregates (FIG. 1b, e, h).

Figure 6:
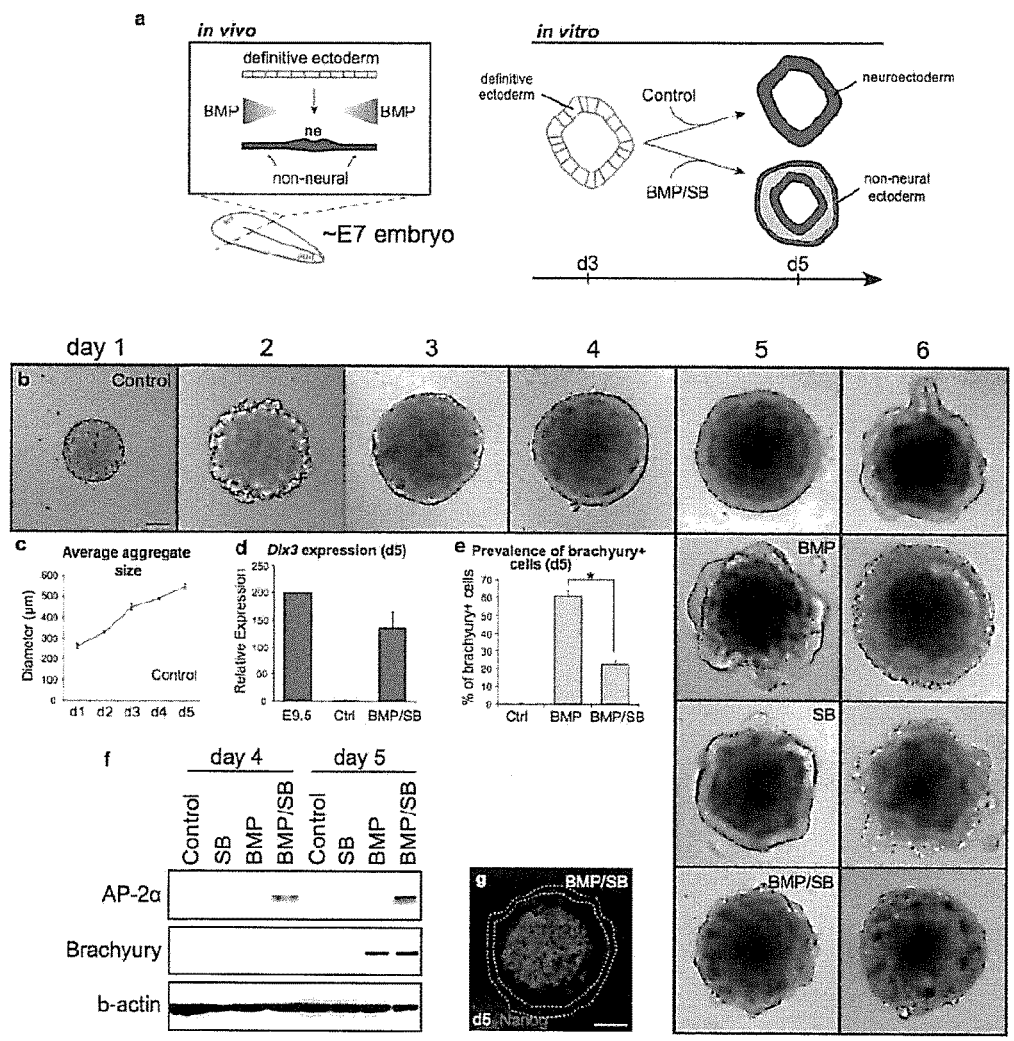
FIG. 6 shows formation of non-neural ectoderm by BMP/SB treatment. a, The induction of non-neural ectoderm in vivo by a BMP gradient can be recapitulated in vitro by treating day 3 SFEBq aggregates with BMP and SB. b, Overt morphological changes occur in BMP, SB and BMP/SB treated aggregates beginning on day 5. Note that the epithelium is disrupted in BMP and SB treated aggregates, while a thin epithelium can be observed along the outer edge of day 5 and 6 BMP/SB treated aggregates. Data are representative of 4-12 separate experiments. c, The average size of ESC aggregates increases during the first 5 days of differentiation (n=10; mean±s.e.m.). d, Dlx3 expression was induced following BMP/SB treatment (n=6, 2 separate experiments; mean±s.d.). e, The percentage of brachyury cells decreased significantly following BMP/SB treatment versus BMP treatment (n=9, 3 separate experiments; *$P<0.05$; mean±s.e.m.). f, Western blot analysis reveals that AP2 protein is only detectable in BMP/SB treated aggregates beginning on day 4 (i.e. 24 hours after treatment). Consistent with qPCR and immunostaining, brachyury is detectable on day 5 in both BMP and BMP/SB treated aggregates. g, Nanog expression is restricted to the core of each BMP/SB aggregate on day 5. Scale bars, 100 µm (b, g).
Figure 7:
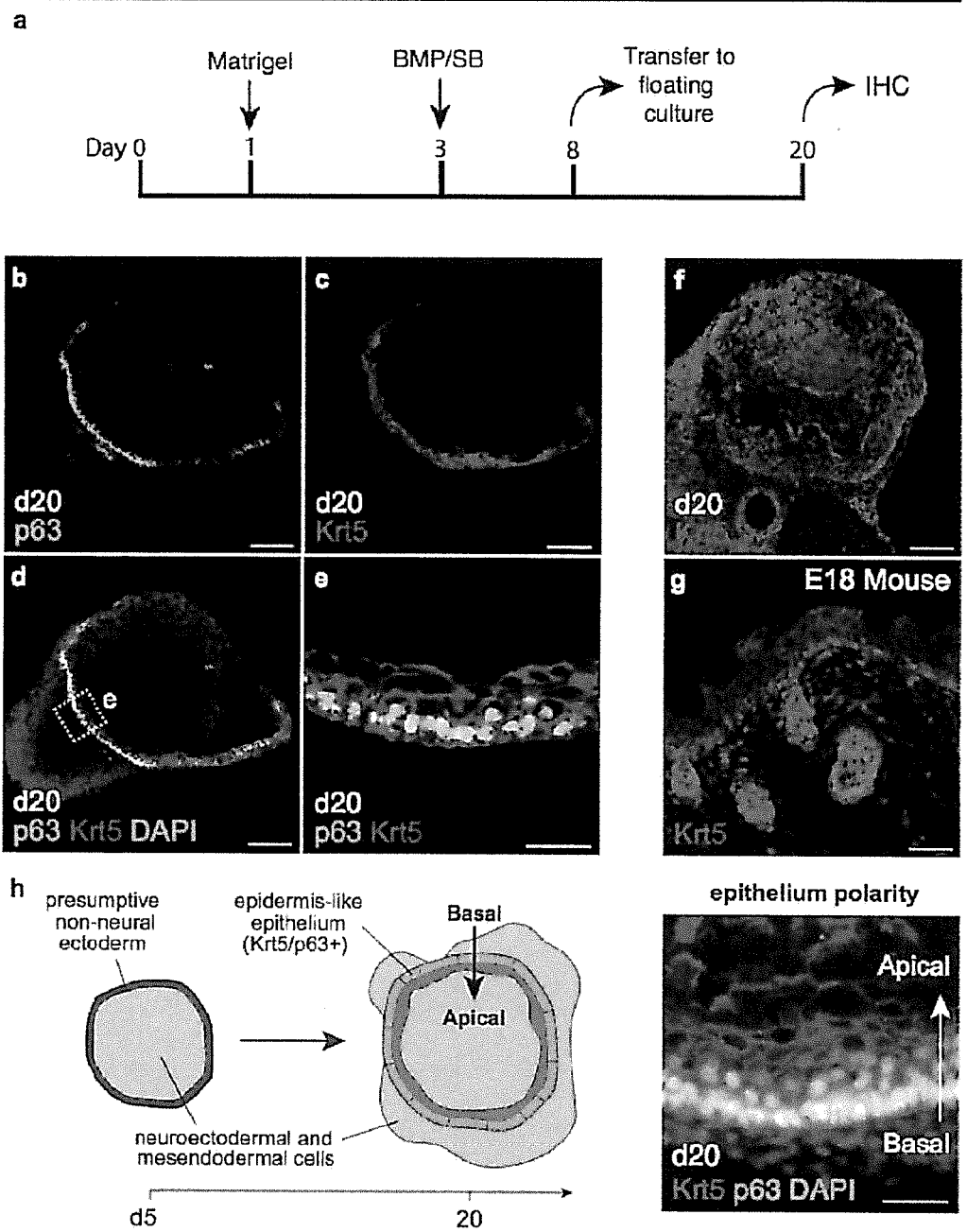
FIG. 7 shows long-term culture of BMP/SB samples generates epidermis. a, Following 8 days of differentiation in 96-well plates, BMP/SB aggregates were washed with N2 Medium and transferred to floating culture for self-guided development. b-e, A Krt5/p63+ epithelium develops in BMP/SB aggregates cultured for 20 days. These results were confirmed in 3 separate experiments. f, g, The staining pattern and morphology of the Krt5+ epithelium is consistent with epidermis on the surface of E18 mouse embryos h, The basal to apical polarity of the epidermis is oriented toward the interior of the aggregate. These results are consistent with in vivo induction of epidermis from the non-neural ectoderm. Interestingly, BMP/SB treatment on day 3 appears to be necessary and sufficient to initiate self-organized induction of epidermis. No Krt5/p63+ epithelium was observed in vehicle treated aggregates (data not shown). Scale bars, 100 µm (b-c, f, g), 25 µm (e, h).

To test whether BMP/SB treatment indeed induced non-neural ectoderm, we assessed the cellular composition of BMP/SB-treated aggregates by immunofluorescence at differentiation day 5. Remarkably, expression of the non-neural ectoderm marker AP2 was found predominantly in the Ecad+ outer-epithelium, but was absent in other regions of treated aggregates (FIG. j). Moreover, we identified an intermediate layer of each aggregate with Sox1+ and N-cadherin (Ncad)+ cells, indicative of the formation of neuroectoderm (FIG. 1j, k). Importantly, Ncad was not observed in the AP2+ outer-epithelium (FIG. 1j), demonstrating a complete transformation of the outer-epithelium into non-neural ectoderm (compare with control samples in FIG. 5h). In addition, the pluripotency marker Nanog was restricted to cells at the core of each aggregate (FIG. 6g). Altogether, these data strongly suggested that the outer-epithelium of day 5 BMP/SB-treated aggregates represents non-neural ectoderm, which surrounds an interior layer containing a mixture of mesendodermal and neuroectodermal tissues and a central core of uncommitted pluripotent cells (see FIG. 1 for an illustration of BMP/SB aggregates and FIG. 6 for more analysis). In support of this conclusion, the outer-epithelium of BMP/SB samples grown for 20 days without additional treatments developed into a Krt5/p63+ epithelium, mimicking the normal embryonic development of the epidermis, which also arises from the non-neural ectoderm (FIG. 7).

Figure 8:
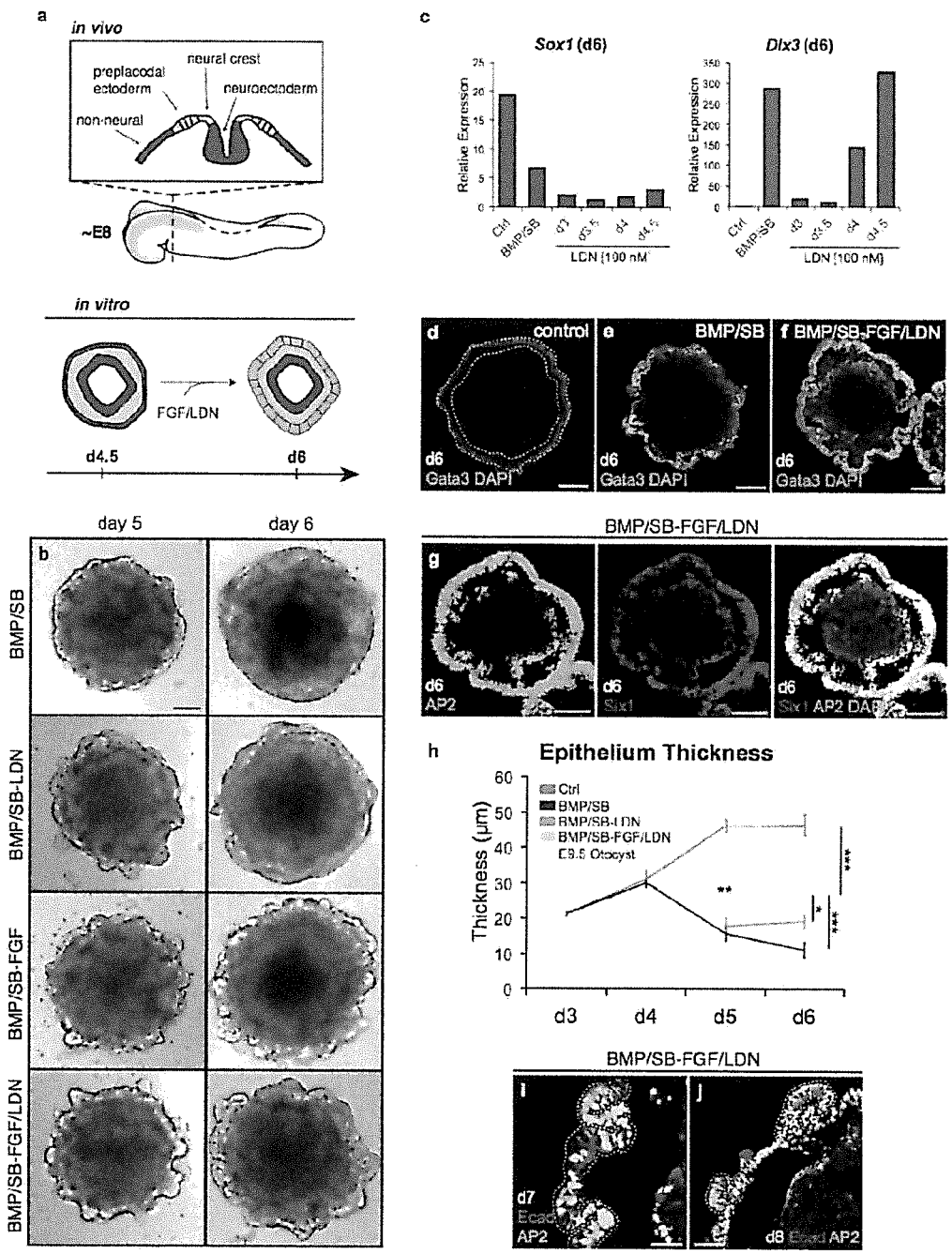
FIG. 8 shows epithelium characteristics following BMP/SB-FGF, -LDN and -FGF/LDN treatment. a, The induction of pre-placodal ectoderm in vivo by BMP inhibitors and FGFs can be recapitulated in vitro by treating day 4-5 BMP/SB aggregates with LDN-193189 and FGF2. b, Morphological changes occur following BMP/SB-LDN, -FGF and -FGF/LDN treatment on days 5 and 6. c, LDN treatment does not induce Sox1 expression, but suppresses Dlx3 expression if treatment occurs on or before day 4 (data are representative of 2 separate experiments). d-g, Gata3 (d-f) and Six1 (g) were detected in the outer epithelium of BMP/SB and BMP/SB-FGF/LDN treated aggregates. h, The apparent thicknesses of Control, BMP/SB, BMP/SB-LDN and BMP/SB-FGF/LDN epithelia on days 3-6. For comparison, the apparent thickness of the E9.5 otic vesicle is superimposed. Data represent 15-20 aggregates from 3-4 separate experiments and 6 otocysts from 3 embryos (mean±s.e.m.). A one-way ANOVA was used to determine significant differences between groups (*$P<0.05$, $P<0.01$, *$P<0.001$). On day 5, BMP/SB-FGF/LDN was significantly different from all other groups. i, j, Epithelium ruffling and vesicle formation on day 7 and 8 following BMP/SB-FGF/LDN treatment. Scale bars, 100 µm (d-g), 50 µm (g), 25 µm (d, f).

The pre-placodal region, a contiguous band of embryonic head ectoderm, arises from the non-neural ectoderm at the neural tube border and is the precursor to all of the cranial placodes (FIG. 8a)[11]. We began treating BMP/SB aggregates with various combinations of the specific BMP inhibitor, LDN-193189 (hereafter, LDN) and FGF2. We found that BMP/SB aggregates treated with LDN on day 4.5 maintained expression of Dlx3, which indicated that BMP inhibition after non-neural induction does not reverse non-neural fate specification (FIG. 8c). In the embryo, the epithelium of the pre-placodal ectoderm is characterized by a thickened morphology relative to the surrounding surface ectoderm[8,11]. Thus, we examined the thickness of epithelia in BMP/SB-LDN samples and found thickened patches that were not present in BMP/SB epithelia (FIG. 8b, h)[8,11]. As observed in vivo, this morphological change appeared to be dependent on endogenous FGFs, as inhibition of FGF signaling by the small molecule SU5402 abolished epithelial thickening (FIG. 9a). A combined treatment of recombinant FGF2 and LDN (hereafter, BMP/SB-FGF/LDN) significantly increased the thickness of the epithelium compared to BMP/SB and BMP/SB-LDN aggregates (FIG. 1n-p and FIG. 8h). Remarkably, in >95% of BMP/SB-FGF/LDN aggregates, a thickened Gata3/Six1/AP2+ epithelium ruffled and formed ovoid vesicles between days 6-8 (FIG. 1p and FIG. 8d-j). These and the following data show that the outer-epithelium of BMP/SB-FGF/LDN-treated aggregates is representative of pre-placodal ectoderm.

Example 2 Differentiation of Pre-Placodal Ectoderm into Otic Placode

Figure 2:
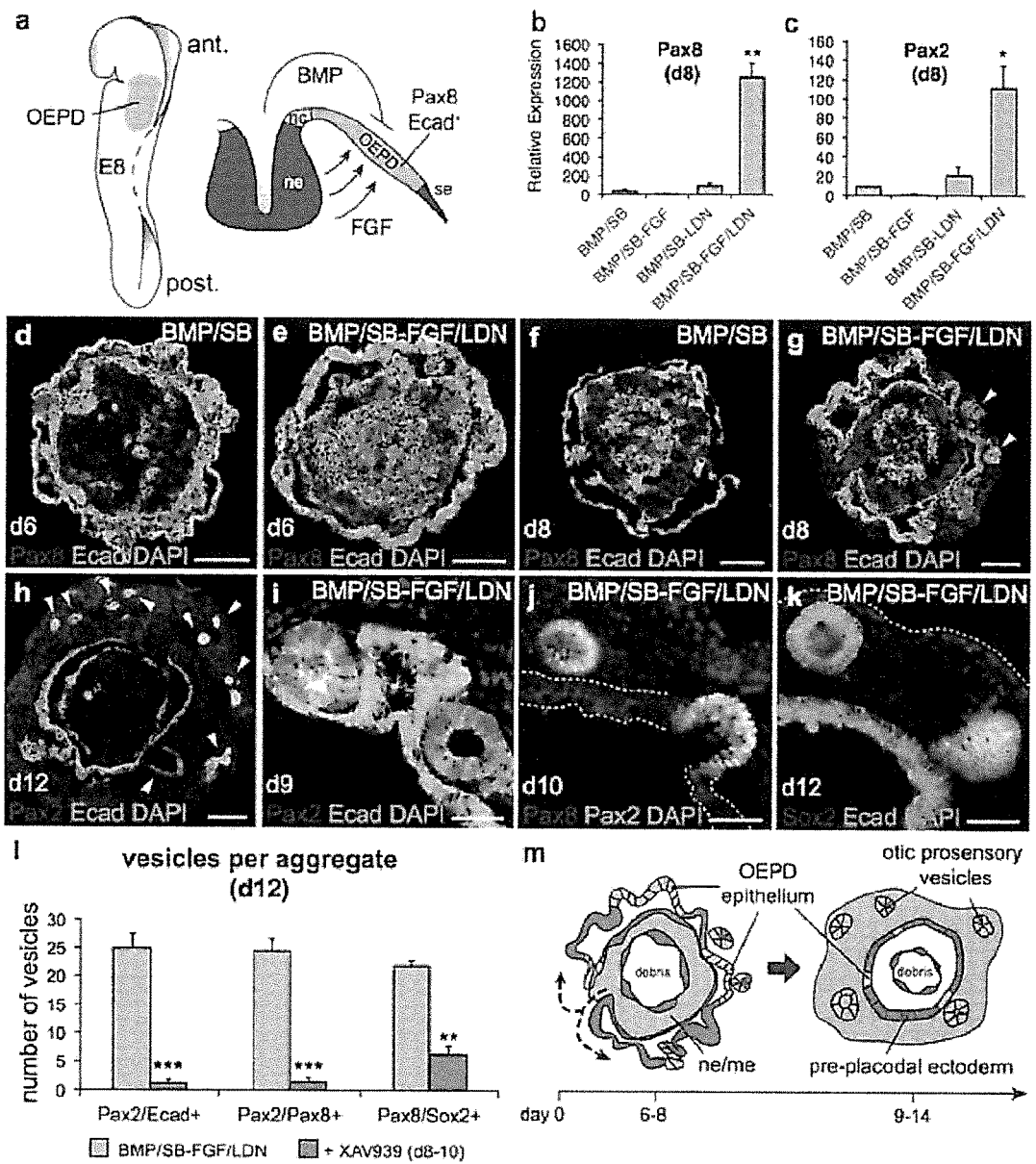
FIG. 2 shows Otic induction from the pre-placodal epithelium in vitro. a, OEPD induction in mice. nc, neural crest; se, surface ectoderm. b, Pax8 and c, Pax2 mRNA expression on day 8 (n=3-4; **P<0.01, *P<0.05; mean±s.e.m.) d-g, Pax8/Ecad expression in (d, f) BMP/SB and (e, g) BMP/SB-FGF/LDN aggregates on day 6 and 8. Arrowheads show vesicles on the exterior of BMP/SB-FGF/LDN aggregates on day 8 h, Day 12 BMP/SB-FGF/LDN aggregate with Pax2/Ecad+ vesicles (arrowheads). i, Pax2/Ecad+, j Pax2/8+, and k Pax8/Sox2+ vesicles invaginate from the inner-epithelium from day 9-12. l, XAV939 decreases the number of vesicles expressing Pax2/Ecad, Pax2/Pax8 and Pax8/Sox2 on day 12. (n=9 aggregates; *P<0.001, P<0.01; mean±s.e.m.). m, Self-guided, inside-out rearrangement of BMP/SB-FGF/LDN aggregates and formation of otic vesicles. Scale bars, 100 µm (d, e, f, h), 50 µm (i-k), 25 µm (g).

In vertebrates, the otic placode is derived from a posterior pre-placodal region known as the otic-epibranchial placode domain (OEPD; FIG. 2a). The otic placode is demarcated from other developing placodes by expression of the transcription factors Pax2/8 (see FIG. 10 for the in vivo situation)[22]. Because the induction of the OEPD requires FGF signaling and the otic placode epithelium thickens, invaginates and forms the otic vesicle (for review see ref 10), we examined whether the vesicle forming-epithelia of BMP/SB-FGF/LDN aggregates were representative of the primordial inner ear. Our qPCR analysis revealed that Pax2 and Pax8 were significantly upregulated in BMP/SB-FGF/LDN samples compared to other conditions (FIG. 2b, c). By day 6, we observed Pax8+ cells distributed in placode-like patches throughout the outer Ecad+ epithelium of only BMP/SB-FGF/LDN aggregates (FIG. 2d, e). Notably, we also observed a population of Pax8+/Ecad− cells in the interior of each aggregate, suggesting formation of mid-hindbrain tissue in this region (see FIG. 11 for further characterization). The percentage of Pax8/Ecad+ epithelium dramatically increased between days 6 and 8 (~15% on day 6 to ~60% on day 8; FIG. 2f, g and FIG. 12a-e) and the Pax8/Ecad+ epithelium bore a striking morphological resemblance to the developing otic placode (see FIG. 10 for comparison). Of note, we did not observe expression of Pax3 or Pax6 in the outer epithelium to indicate the development of other cranial placodes (FIG. 11c-g). Taken together, these findings show that FGF/LDN treatment is critically important for in vitro otic placode induction and that treatment is most effective when performed between days 4 and 5 (FIG. 12f).

Figure 10:
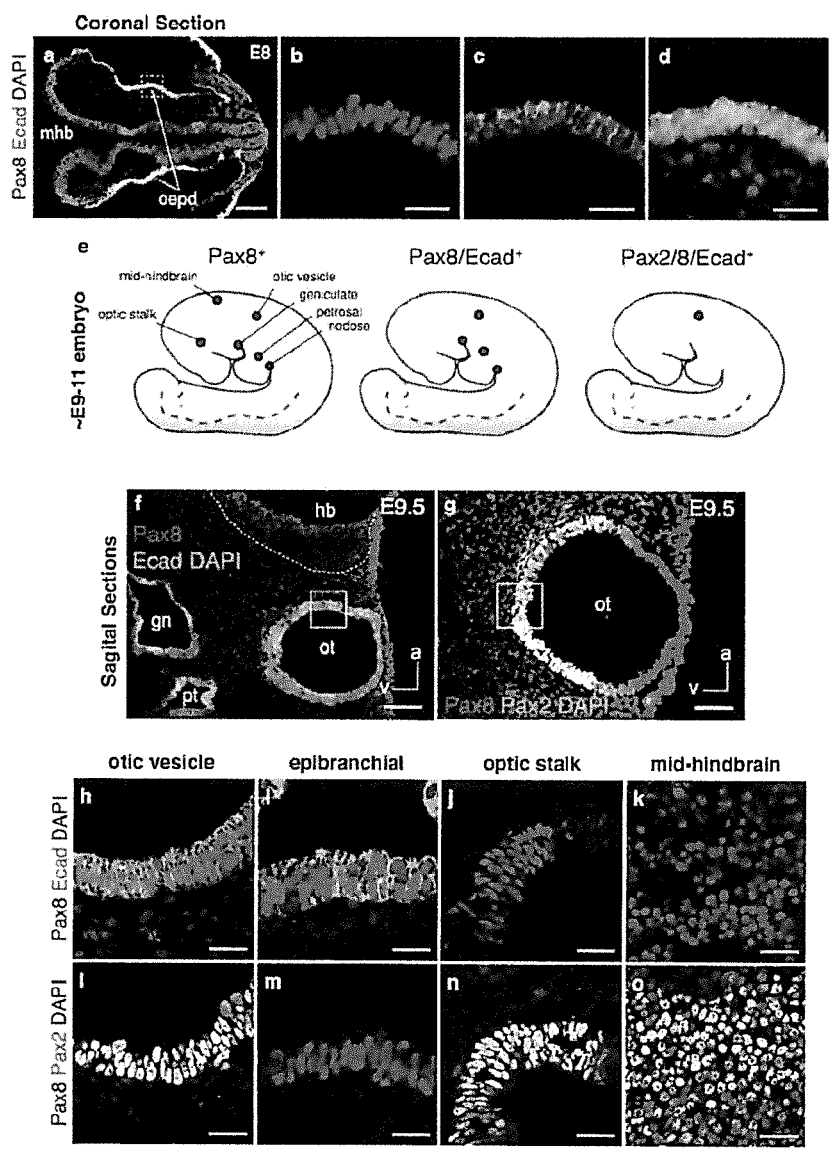
FIG. 10 shows identification of otic progenitor cells. a-d, At E8, Pax8/Ecad expression in the surface ectoderm marks the otic-epibranchial placode domain (oepd). Pax8 expression is also detected in the mid-hindbrain region of the neuroepithelium (mhb). e-o, The well-established otic markers Pax2/8 are not unique to the inner ear during development. On E9.5 Pax2/8 expression co-localizes in the optic stalk, mid-hindbrain and kidney as well as the otic vesicle. We found that the combination of Pax2/8 and Ecad provides a unique signature of otic placode/vesicle fate. At ~E9-11, Pax8 is expressed in the otic vesicle, epibranchial placodes (i.e. *geniculate*, petrosal and nodose), optic stalk, and mid-hindbrain. Pax8/Ecad expression is restricted to the otic vesicle and epibranchial placodes. Pax2/8/Ecad expression is restricted to otic vesicle (h, l). a, anterior, v, ventral. Scale bars, 100 µm (a,f,g), 25 µm (b-d,h-o).
Figure 14:
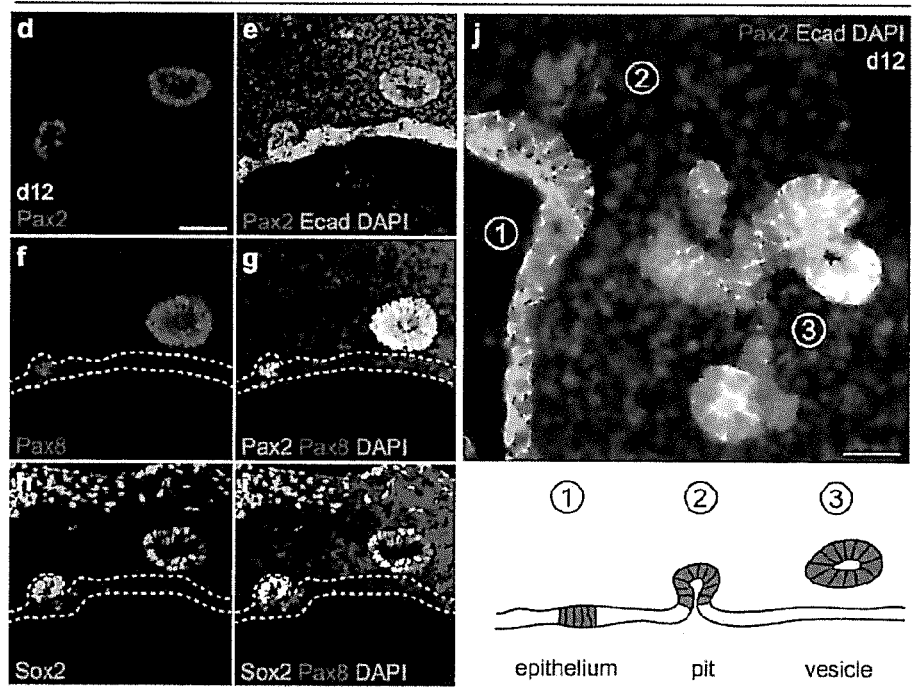
FIG. 14 shows prosensory vesicle formation. a-c, Pax8/Ecad+ vesicle formation from the outer epithelium during days 6-8. d-i, Serial sections show co-expression of Pax2/8, Ecad, and Sox2 in vesicles, indicating an inner ear prosensory fate. j, A fortuitous section of a day 12 aggregate illustrates the 3 steps of vesicle formation. Scale bars, 50 µm (d-i), 25 µm (a-c). Note that vesicle formation appeared to be continuous beginning on day 7 until approximately day 14/16. We did not, however, determine the precise time that vesicle formation ceased.
Figure 15:
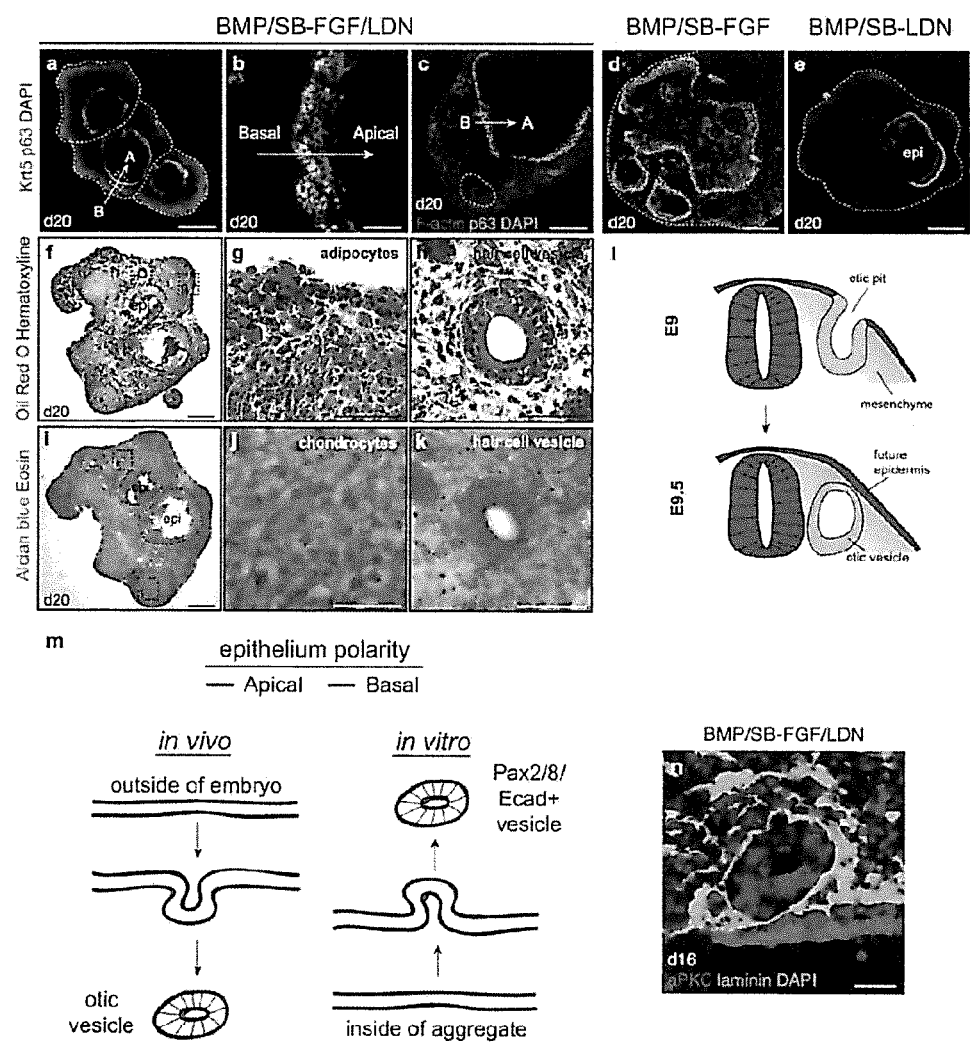
FIG. 15 shows epidermis arises under all BMP/SB treated conditions and vesicles evaginate into mesenchyme-like tissue. a-e, Krt5/p63+ epidermis-like epithelium forms in BMP/SB-FGF, -LDN and -FGF/LDN aggregates. In BMP/SB-LDN and BMP/SB-FGF/LDN aggregates the Krt5/p63+ epithelium lines the central cavity of the aggregate with the apical surface oriented toward the interior of the aggregate (b). F-actin staining with phalloidin reveals that vesicles (outlined) are located basal to the p63+ epithelium (c). f-l, Oil Red O and Alcian Blue staining shows that adipocytes and chondrocytes develop adjacent to hair cell-containing vesicles in the outer cell mass. This confirms that presence of mesenchymal development in this region of the aggregates. The development of hair cell vesicles surrounded by mesodermal tissue in BMP/SB-FGF/LDN aggregates mimics the development of the inner ear in the head mesenchyme (l). m, One apparent discrepancy between in vitro and in vivo otic vesicle formation is that the otic placode invaginates into the body to form the otic vesicle (l, ~E9-9.5) and, conversely, in vitro vesicles evaginate out into the medium or exterior cell layer. From the Krt5/p63 staining results, we can see that the basal-to-apical polarity of the inner epithelium is oriented outside-to-inside relative to the surface of BMP/SB-FGF/LDN aggregates (note that a similar orientation was observed in BMP/SB aggregates (FIG. 7). The schematic illustrates how vesicles that appear to evaginate toward the exterior of the aggregate in vitro are, in actuality, invaginating relative to the polarity of the epithelium. Staining for apical (aPKC) and basal (laminin) polarity markers (n) confirms this model. Scale bars, 250 µm (a), 100 µm (c-f, i), 50 µm (g, h, j, k) 25 µm (b,n).
Figure 18:
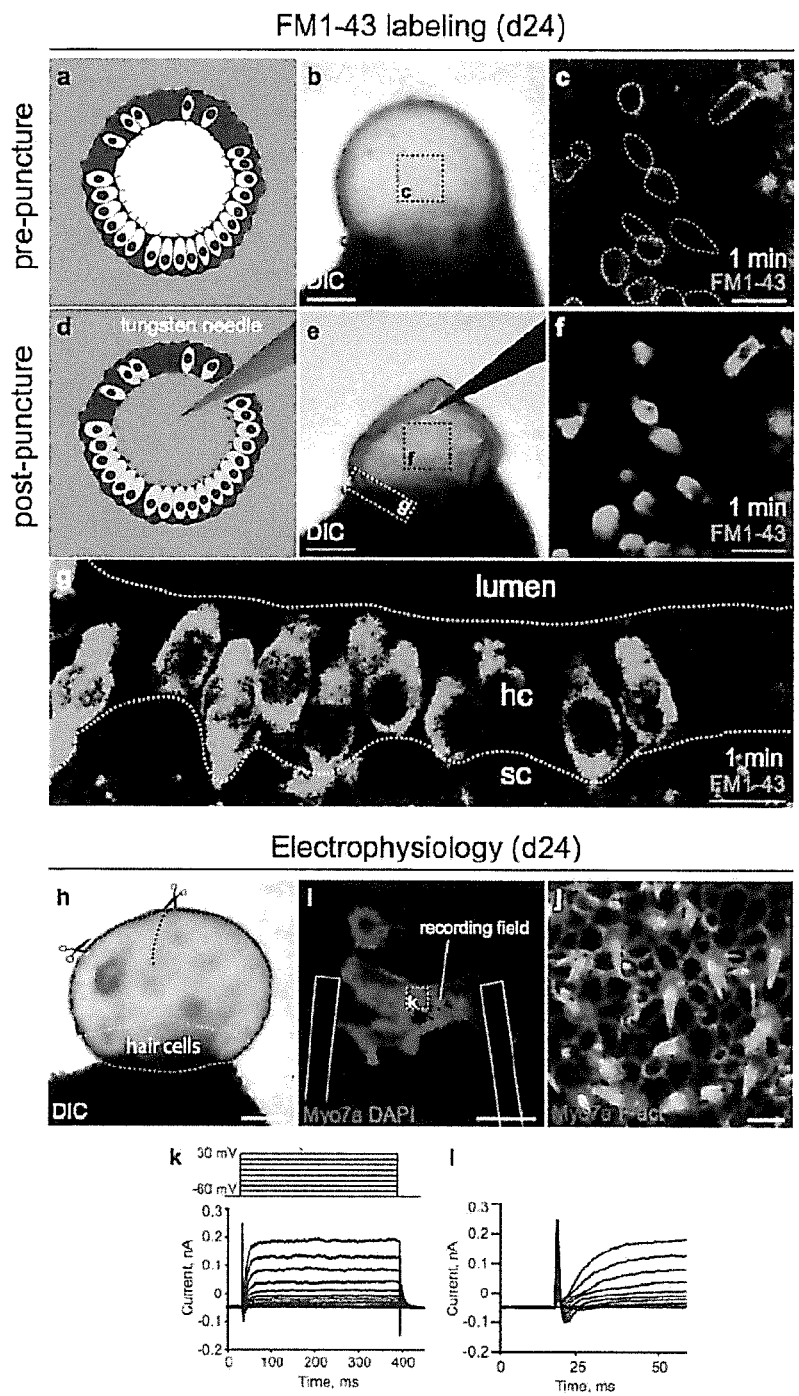
FIG. 18 shows functional properties of stem cell-derived hair cells using a FM1-43 uptake assay and electrophysiological recordings. a-c, Vesicles containing hair cells were identified by morphology as translucent cysts protruding from the side of cell aggregates. Hair cells in the epithelium could be identified through the vesicle wall following treatment with FM1-43FX for 1 minute. d-g, After puncturing the vesicle with a 0.25 μm tungsten needle and another 1 minute incubation, previously outlined hair cells became fluorescent (f). Confocal imaging of the epithelial sheet revealed FM1-43FX labeled cells with the same morphology as hair cells. The underlying supporting cells did not take up the dye (g; sc). These results are consistent with previous investigations (see Meyers et al., 2003) and were confirmed using 10 vesicles from 3 different experiments. h, For electrophysiological recording, vesicles were microdissected to flatten the sensory epithelium (typically found in the portion of the vesicle abutting the aggregate). i, The sensory epithelium was secured to a coverslip by two needles during recording. j, Post-recording, samples were fixed and stained for Myo7a and F-actin (phalloidin) to confirm the identity of hair cells. k, Representative traces of complex current which include the inward and outward components. The voltage protocol is shown at the top. l, Expanded view of transient inward current (likely sodium). Outward current was truncated for clarity. Scale bars, 250 μm (b, e, h, i), 25 μm (c, f, g), 5 μm (j).
Figure 21:
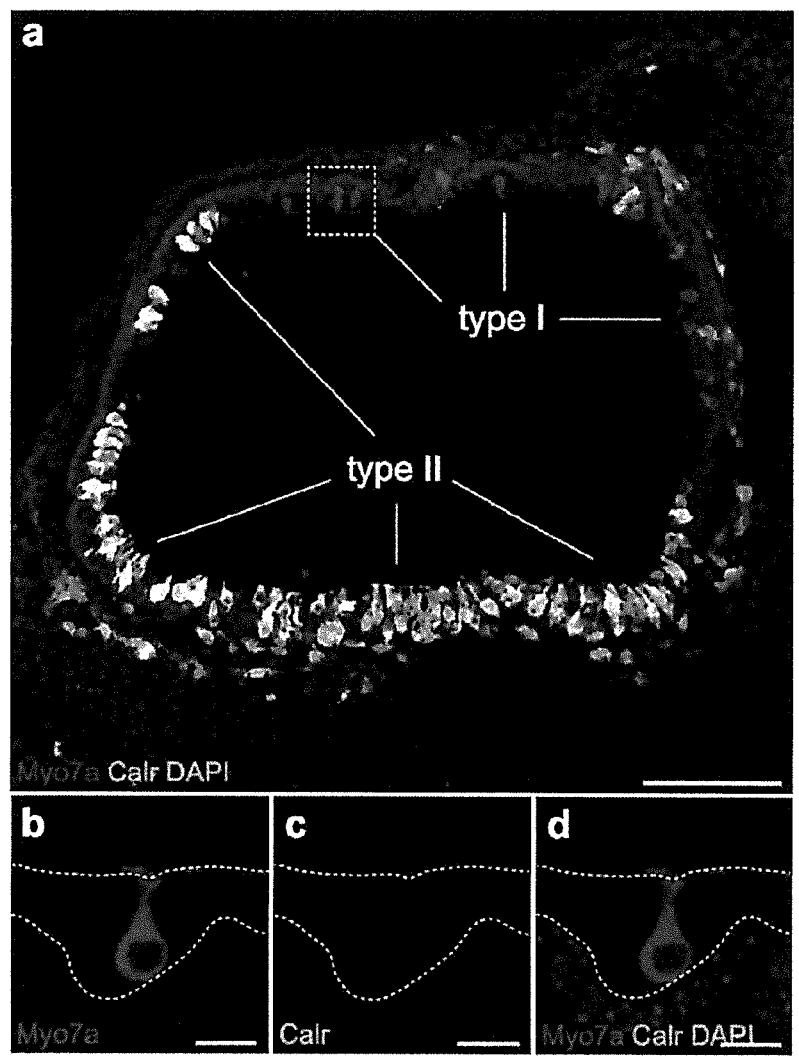
FIG. 21 Type I vestibular hair cells develop in late-stage (>day 25) BMP/SB-FGF/LDN treated aggregates. a, Representative day 27 vesicle containing Type I and Type II vestibular hair cells. b-d, Type I vestibular hair cells can be distinguished by a pear-like shape and a lack of Calretinin (Calr) expression. Type II hair cells express Calretinin. Scale bars, 100 μm (a), 25 μm (b-d).

In vivo, the prosensory domain of the otic placode (otic vesicle at later stages) gives rise to the vestibular/cochlear sensory epithelia and inner ear sensory neurons. Otic prosensory cells are defined by expression of Pax2/8, Ecad, Sox2, Jagged1 (Jag1) and Myosin VIIa (Myo7a; FIGS. 10 and 16). On day 8 of differentiation, BMP/SB-FGF/LDN aggregates were transferred to a serum-free, floating culture to allow further differentiation. In each aggregate analyzed, approximately 24 hours after transfer, the interior cell mass breached the outer-epithelium and formed a heterogeneous cell layer on the exterior of the aggregate (n=253 aggregates; FIG. 2h, m and FIG. 13). This indicated that the outer-epithelium transitions to an inner-epithelium lining the core of each aggregate. During days 9-12 we observed the continuous evagination of vesicles containing Pax2/Ecad, Pax2/8, and Sox2/Pax8+ cells from the presumptive OEPD epithelium into the exterior cell layer (FIG. 2h-k and FIGS. 13 and 14), which resulted in ~20-28 Pax2/8/Sox2+ vesicles per aggregate (FIG. 21). We hypothesized that endogenous Wnt signaling may underlie induction of vesicles bearing otic prosensory markers in our culture because Wnt signaling is necessary for otic placode formation in vivo[10]. Confirming this hypothesis, treatment of aggregates with the Wnt inhibitor XAV939 from day 8-10 significantly decreased the number of prosensory vesicles and, specifically, reduced the prevalence of Pax2+ vesicles (FIG. 2i). These data indicate that endogenous Wnt signaling induces formation of otic vesicles from the presumptive otic placode using similar mechanisms as observed in vivo. Interestingly, the remaining inner-epithelium developed into Krt5/p63+ epidermis and the exterior layer of cells gave rise to mesenchyme tissues like cartilage and adipose (FIG. 15). The basal (p63+) layer of the inner-epithelium was oriented so that the apical surface of the epithelium was facing the interior of the aggregate. Thus, the process of vesicle evagination toward the outside of the aggregate is consistent with the orientation of embryonic otic vesicle invagination into the head mesenchyme (see FIG. 15 for further explanation).

During development, the prosensory domain of the otic vesicle is destined to become sensory epithelia harboring Myo7a$^+$ sensory hair cells. Surprisingly, Myo7a$^+$ cells started to emerge in Sox2/Jag1$^+$ vesicles at day 14 without any additional treatments (FIG. 16a-f). In a subset of vesicles, we also observed distinct Myo7a$^+$ cells with p27$^{kiP1+}$ nuclei that resembled immature hair cells in the embryonic day 12-14 mouse inner ear (FIG. 3a). By day 15 and 16, we found that each aggregate contained 15.4±4.8 (d16; n=12 aggregates) vesicles lined with Myo7a/Sox2$^+$ cells bearing the stereotyped morphology of sensory hair cells with large nuclei (~8 μm long-axis diameter) positioned basal to an elongated apical end (FIG. 3b). The Myo7a/Sox2$^+$ cells were organized in a radial pattern with the apical end abutting a lumen of varying sizes (~5-1000 μm long axis diameter; FIG. 3b-d). Basal to each layer of Myo7a/Sox2$^+$ cells was a tightly arranged layer of Sox2$^+$ cells reminiscent of supporting cells (FIG. 3b-h). Mimicking the in vivo sensory epithelia, hair cells and supporting cells could be further distinguished by expression of Brn3c and Cyclin D1, respectively (FIGS. 16e, i and 17a-f). F-actin staining revealed cell-cell tight-junctions along the luminal surface as well as F-actin/Espin$^+$ stereocilia bundles (~0.5-11 μm in height; FIG. 3i-l, FIG. 17g-i and Video 2). Every Myo7a+ cell analyzed also had an acetylated-α-Tubulin+ kinocilium protruding from the apical end into the lumen (~1-18 μm in length; FIG. 3k, l). Stereocilia and kinocilium were not visible at day 16, but the average height increased from d20 to d24 and fell within the range of heights recorded from an adult mouse utricle (FIG. 3l)[23]. Electron microscopy revealed that stereocilia bundles shared a similar structural organization with in vivo hair cells (FIG. 3m and FIG. 17j-m). The hair cells also appeared to be functional based on the rapid uptake of FM1-43 dye and the diversity of voltage-dependent currents (FIG. 3n-p and FIG. 18)[24,25]. In all cells included in this study we observed outwardly rectifying potassium currents with voltage-dependent activation kinetics to amplitudes ranging from 194 pA to 3612 pA with a mean of 1003±527 pA (n=6; FIG. 3p). Additionally, some cells were distinguished by the presence of a transient inward current, likely reflecting sodium channel activity (Supplemental FIG. 14k, l). By day 20 each BMP/SB-FGF/LDN aggregate contained 1,552.3±83.1 Myo7a$^+$ cells with typical hair cell morphology, in striking contrast to other conditions that yielded no Myo7a$^+$ cells (~1-2% of all cells in the aggregate; n=12-16 aggregates per condition; FIG. 3q-s). We conclude from these data that the cytoarchitecture, cellular morphology, and functional characteristics observed in Myo7a/Sox2$^+$ vesicles are identical to sensory epithelia in the inner ear (FIG. 3t).

Figure 4:
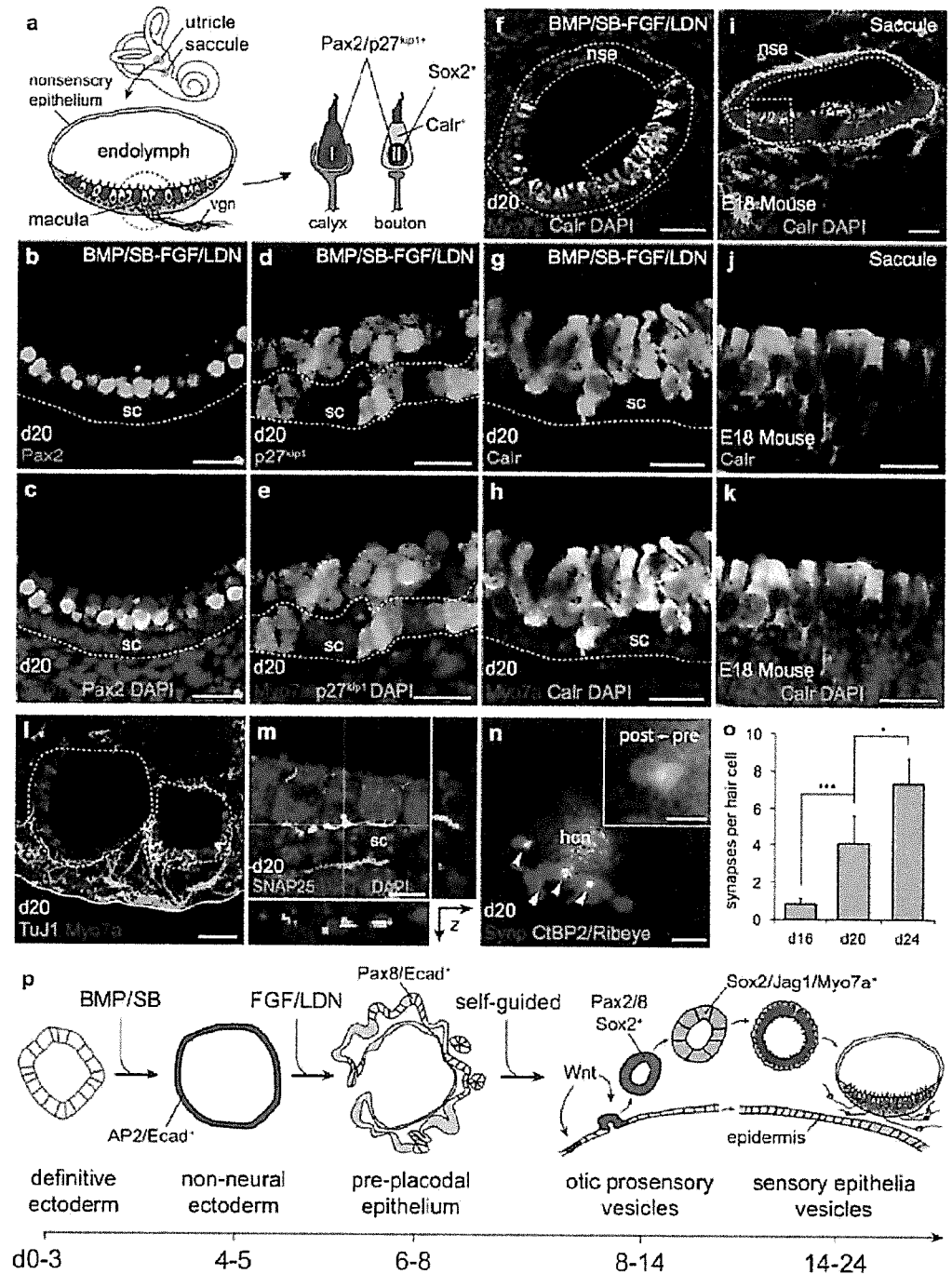
FIG. 4 shows stem cell-derived sensory epithelia are comparable to immature vestibular end organs. a, Schematic of vestibular end organs and type I/II vestibular hair cells. vgn, vestibular ganglion neurons. b, c, Pax2 is expressed in all Myo7a+ stem cell-derived hair cells on day 20. d, e, $p27^{kiP1}$ is localized to the nucleus of most Myo7a+ stem cell-derived hair cells. f-k, Calretinin is expressed in Myo7a+ stem cell-derived hair cells mimicking the E18 mouse saccule (sagittal view) in vivo. nse, non-sensory epithelium. l, TuJ1+ neurons extending processes towards epithelia containing hair cells. m, The synaptic protein SNAP-25 is localized to the basal end of hair cells. n, The post-synaptic marker synaptophysin (Synp) co-localizes with the ribbon synapse protein CtBP2/RIBEYE (arrowheads and inset). hcn, hair cell nucleus. o, Quantification of synapses on day 16, 20 and 24 hair cells (n>100 cells, *P<0.05, ***P<0.001; mean±s.d.). p, Overview of in vitro sensory epithelium induction. Scale bars, 50 µm (f, i, l), 25 µm (b-e, g, h, j, k), 10 µm (m), 5 µm (n).
Figure 20:
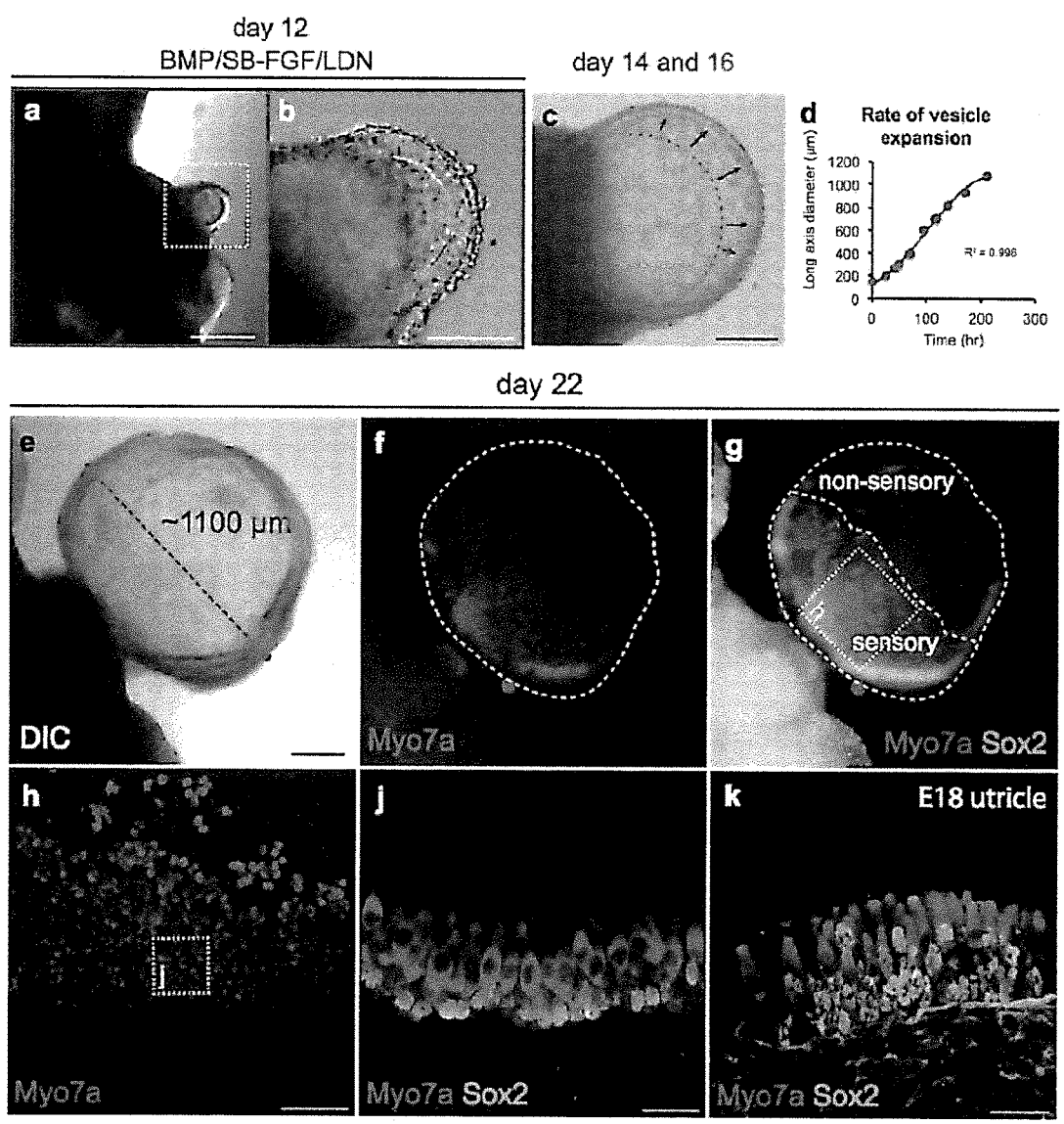
FIG. 20 shows expansion of hair cell-containing vesicles (d12-22). a, b, We tracked the development of a vesicle that erupted on the surface of the aggregate unusually early at day 12. c-e, The long-axis diameter of the aggregate grew to be ~1100 μm by day 22, which is on the scale of a typical adult mouse utricle (P30; see Li et al. 2008 for comparison). f-h, Whole-mount immunohistochemistry showed that a "sensory" region of the vesicle contained an epithelium with Sox2$^+$ supporting cells and a dense population of Myo7a/Sox2$^+$ hair cells, while a "non-sensory" region contained dispersed clusters of sensory epithelium. j, The regional organization and size of the vesicle is comparable to the E18 utricle (shown in k) and saccule (not shown). Scale bars, 250 μm (a, e-g), 100 μm (b, c, h), 25 μm (j). Note the similarities between these stem cell-derived vesicles and cysts generated by maintaining utricular explants in 3D culture (reported in Gaboyard et al., 2005).

There are four distinct populations of hair cells in the mammalian inner ear; type I/II vestibular and inner/outer cochlear hair cells. We wished to reveal which type of hair cells populated the stem cell-derived sensory epithelia in our culture. Previous studies have shown that expression of Pax2 and nuclear localization of p27$^{kiP1}$ can distinguish vestibular from cochlear hair cells[26-28]. Additionally, expression of the calcium binding protein Calretinin and Sox2 uniquely labels Type II vestibular hair cells, whereas calyceal innervation from sensory neurons identifies Type I vestibular hair cells (FIG. 4a)[26,29,30]. On day 20, nearly all stem cell-derived hair cells were Sox2/Pax2$^+$ and ~90% also had p27$^{kiP1+}$ nuclei (n>250 hair cells; FIGS. 3b-d, h and 4b-e). Moreover, every hair cell also expressed Calretinin suggesting a uniform population of Type II vestibular hair cells (FIG. 4f-k). However, by day 27, occasional Type I vestibular hair cells were observed (FIG. 2l). Intriguingly, we also observed discrete populations of Calretinin$^+$ and Brn3c/TuJ1/Neurofilament$^+$ neurons that extended processes toward the sensory epithelia (FIG. 4l and FIG. 19a-d). Unexpectedly, by day 16, hair cells exhibited punctuate expression of CtBP2/RIBEYE$^+$ co-localized with the synaptic and neuronal markers TuJ1, Synaptophysin, SNAP-25 and Rab3, indicating the formation of ribbon synapses with adjacent neurons (FIG. 4l-n and FIG. 19e-j). Remarkably, the number of ribbon synapses increased over time in culture, suggesting a maturation process similar to normal inner ear hair cells (FIG. 4o and FIG. 19h-j). We did not, however, detect the presence of mature calyceal synapses (i.e. Caspr1/2) characteristic of Type I vestibular hair cells (data not shown)[30]. Structurally, we noted the presence of larger lumen vesicles (3.7±0.3 per aggregate, n=15 aggregates, defined as >50 μm long-axis diameter vesicles) with regions of sensory (with hair cells) and non-sensory (without hair cells) epithelia identical in organization to a generic vestibular end organ (FIG. 4a, f, i and FIG. 18b, h and FIG. 20). Together, these results indicate that stem-cell derived vesicles in our culture represent immature vestibular end organs, specifically the utricle and/or saccule (FIG. 4i)[12,27,28].

Suga et al.[1] recently demonstrated that anterior pituitary gland tissue could be induced in a modified SFEBq culture. Both anterior pituitary and inner ear are derivatives of the non-neural ectoderm and, later, the pre-placodal region (PPR) of the head ectoderm. The anterior pituitary gland, however, is derived from the anterior most segment of the PPR whereas the inner ear is derived from the posterior PPR. In order to selectively induce anterior ectoderm, Suga et al. made two critical modifications to the original SFEBq culture. First, they used a medium devoid of any factors that influence tissue patterning, which has been shown previously to allow the induction of anterior neuroectoderm epithelia similar to the developing hypothalamus. Secondly, they seeded more ESCs (10,000 or greater) in each well to create a larger cell aggregate. In the large cell aggregate configuration a self-organizing non-neural epithelium was induced on the surface of the aggregate, while a neuroectoderm layer developed inside the aggregate. The authors speculated that the increased number of cells likely sets up a microenvironment permissive of the finely tuned BMP signaling that leads to non-neural and neuroectoderm induction in vivo. Importantly, they showed that treating smaller cell aggregates (3,000 cells) with BMP induced non-neural markers, however, the authors abandoned this approach for the large aggregate configuration. In the present study, we sought to gain better experimental control of non-neural ectoderm induction by applying BMP and a TGFβ inhibitor to the small cell aggregates. Additionally, we used a medium containing knockout serum replacement, which is permissive of posterior neuroectoderm induction in the presence of fibroblast growth factor[2,3] We conjectured that this posteriorizing effect would translate to non-neural ectoderm tissue. Together, the non-neural induction strategies used by Suga et al. and in the present study provide mechanistic insight into how to derive placodes along the anterior-posterior axis.

In conclusion, the present study reveals that aggregates of pluripotent stem cells can transform sequentially in vitro into non-neural, pre-placodal and inner ear sensory epithelia using precisely timed treatments of signaling proteins in a defined 3D culture system (FIG. 4*l*). Importantly, our findings underscore a previously unreported binary mechanism of BMP and TGFβ signaling underlying non-neural ectoderm induction. Furthermore, subsequent inhibition of BMP signaling concomitant with activation of FGF signaling are required for pre-placodal induction. Remarkably, formation of these precursors is sufficient to trigger self-guided induction of the sensory epithelia, from which hair cells with structural and functional properties of native mechanosensitive hair cells in the inner ear spontaneously arise in a significant number (approximately 1,500 hair cells per aggregate). This novel approach not only can be used as a potent model system to elucidate the mechanisms underlying inner ear development, but also will provide an easily accessible and reproducible means of generating hair cells for in vitro disease modeling, drug discovery or cellular therapy experiments.

Figure 22:
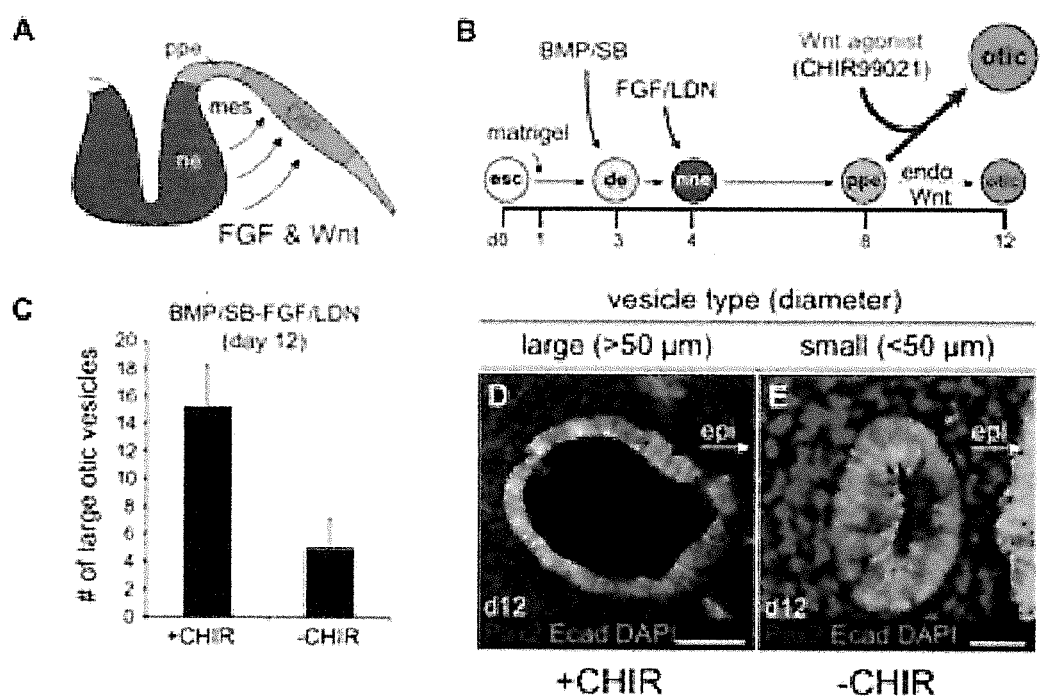
FIG. 22 Activation of Wnt signaling following BMP/SB-FGF/LDN treatment can enhance production of otic progenitors. A, Endogenous Wnt activity is necessary for otic placode formation in vivo. B, Schematic overview of Wnt agonist treatment. C, The number of large otic vesicles (defined as vesicles with a lumen larger than 50 μm) increases following Wnt activation. D, Comparison of representative large and small vesicles in Wnt agonist treated aggregates. Scale bars, 50 μm (D), 25 μm (E).

Example 3 Wnt and Shh Signaling Activation can Increase the Number of the Inner Ear Cells Derived from Preplacodal Ectoderm In our previous study we found that inhibition of Wnt signaling using a small molecule inhibitor, XAV939 (on days 8-10), blocked the generation of otic vesicles following BMP/SB-FGF/LDN treatment. This demonstrated that Wnt signaling is critical for vesicle formation in vitro mimicking in vivo otic vesicle formation. We tested whether Wnt activation could enhance the generation of otic vesicles in vitro. BMP/SB-FGF/LDN treated aggregates were transferred to a floating culture in N2 Medium containing the Wnt agonist CHIR99021 (3 μM) on day 8 (FIG. 22B). On day 10 the medium was changed to remove CHIR99021 from the medium. On day 12, CHIR99021 treated aggregates contained a higher abundance of Pax2/Ecad+ vesicles with a luminal diameter greater than 50 μm (referred to as large vesicles; FIGS. 22B and 22C). This result indicated that greater numbers of otic cells are produced in response to Wnt activation.

Figure 23:
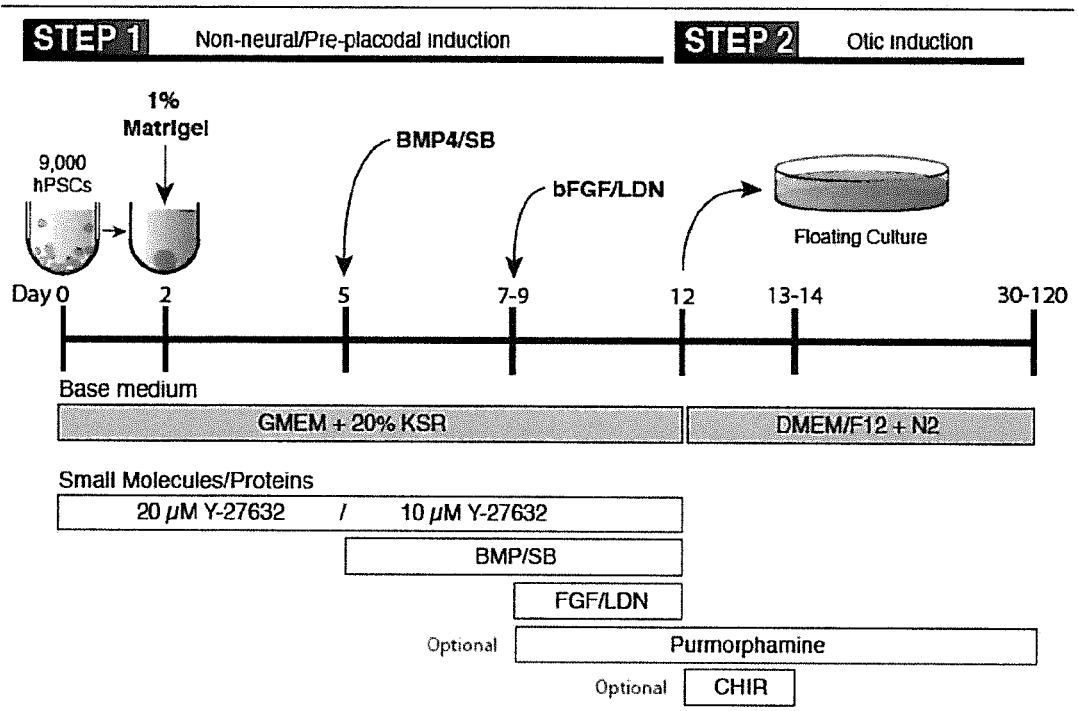
FIG. 23 shows a schematic representation of an exemplary, non-limiting embodiment, of a method for in vitro differentiation of human pluripotent stem cells into preplacodal ectoderm, otic placode, and inner ear sensory hair cells.

Example 4 Generation of Preplacodal and OEPD-Like Epithelia from Human Pluripotent Stem Cells Day 0—hPSC Dissociation and Plating in 96-Well Plates:

Prior to differentiation, human pluripotent stem cells were maintained in feeder-free conditions in dishes coated with recombinant vitronectin or an equivalent substrate (e.g. MATRIGEL™ (a gelatinous protein mixture secreted by Engelbreth-Holm-Swarm (EHS) mouse sarcoma cells)). To begin differentiation, human PSCs were dissociated into single-cells or small cell-clusters with an appropriate cell dissociation reagent (e.g. Trypsin, TrypLE, Versene, EDTA, etc.). As schematically illustrated in FIG. 23, dissociated hPSCs were resuspended in Differentiation Medium containing 20% Knockout Serum (hereafter referred to as "DMK") and counted. After counting, dissociated cells were diluted to a concentration of 90,000 cells/mL in DMK. 100 μl (i.e. 9000 cells in total) of this cell suspension is then plated in each well of a low-cell adherence 96-well plate with U or V-shaped wells (V-bottom plates are preferred). Note that 3,000-10,000 cells could be used per well, but 9,000 cells are preferred. Over a period of 24 hours the individual cells aggregated together to form a spherical cell aggregate or embryoid body. For this embodiment hPSCs were fully dissociated into single cells, therefore an inhibitor of the ROCK-signaling pathway was included in the medium to prevent apoptosis (e.g. GSK429286A, ROCK II inhibitor, Thiazovivin, Y27632, etc.). 10-20 μM Y27632 is preferred.

Day 2—Addition of MATRIGEL™ (a Gelatinous Protein Mixture Secreted by Engelbreth-Holm-Swarm (EHS) Mouse Sarcoma Cells) to Initiate Epithelia Formation After 24-48 hours, half of the medium was changed and replaced with fresh DMK containing 2% (v/v) MATRIGEL™ (a gelatinous protein mixture secreted by Engelbreth-Holm-Swarm (EHS) mouse sarcoma cells) or an equivalent reagent containing laminin. MATRIGEL™ (a gelatinous protein mixture secreted by Engelbreth-Holm-Swarm (EHS) mouse sarcoma cells) contains a high concentration of laminin that aids the formation of a basement membrane on the outer surface of the cell aggregate. The establishment of a basement membrane allowed an epithelium to form on the outer surface of the aggregates. An E-cadherin+/Nanog− epithelium, representing ectodermal tissue, was usually visible by day 3 or 4 of differentiation on the outer surface of each aggregate.

Day ~5—Addition of BMP4 and a TGFβ Inhibitor to Initiate Non-Neural Ectoderm Development Between days 3-6 (preferable day 5), 25 μl of fresh DMK containing recombinant BMP4 (1-25 ng/mL, 10 ng/mL preferred final concentration) and a TGFβ inhibitor (e.g. SB431542, ALK5 inhibitor, A83-01, etc.; 1-10 μM SB431542 preferred) was added to the medium in each well. Preferably a final concentration of 10 ng/mL BMP4 and 1 μM SB431542. This treatment induced the development of non-neural ectoderm cells in the outer-epithelium.

Figure 24:
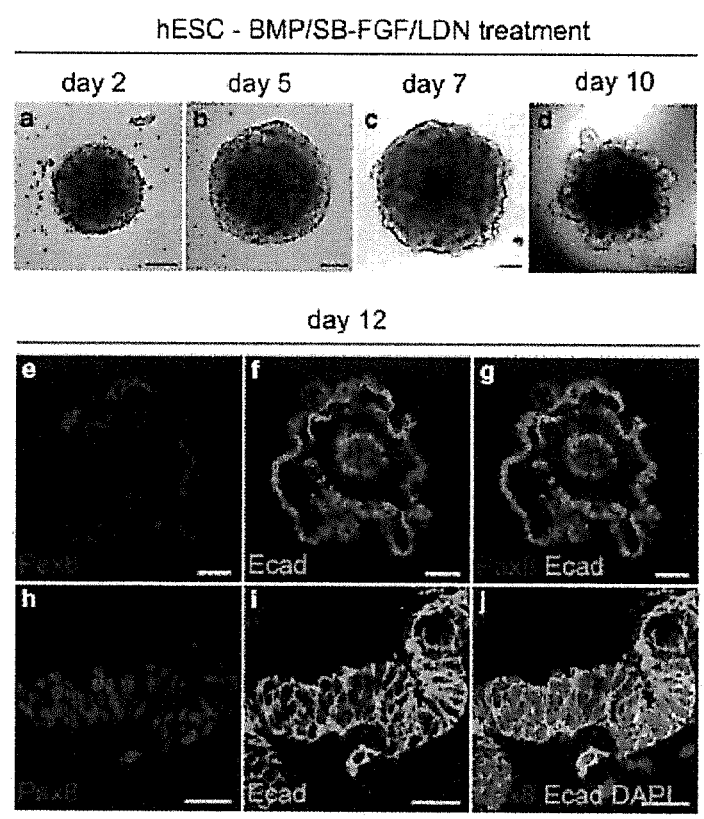
FIG. 24 shows differentiation of hESCs into otic progenitor epithelium. a-d, Representative images of hESC aggregates on days 2, 5, 7 and 10. The full treatment of BMP/SB-FGF/LDN was used for these experiments. e-j, Pax8/E-cadherin expression in the outer epithelium of hESC aggregates on day 12. Scale bars, 200 μm (d), 100 μm (a-c, e-g), 30 μm (h-j).

Day ~7—Addition of FGF and a BMP Inhibitor to Initiate Preplacodal Ectoderm Development On day 7, 25 μl of fresh DMK containing recombinant FGF2 and the BMP inhibitor, LDN193189, was added to the medium in each well. at a final concentration of 25 ng/mL FGF-2 and 1 μM LDN193189. This treatment induced the development of pre-placodal ectoderm cells in the outer-epithelium. These cells are defined by the expression of one or more of the following genes/proteins: specifically, SIX1/4, EYA1/2, IRX1/2/3, less specifically, AP2, DLX3/5/6, GATA2/3, FOXI1/3, E-cadherin. We analyzed the morphology of the outer-epithelium of each aggregate for thickening and ruffling. We found pseudostratified ECAD/PAX8+ cells in the outer-epithelium of BMP/SB-FGF/LDN treated aggregates on day 12 indicating the proper induction of preplacodal and OEPD-like epithelia (FIG. 24).

Example 5 Generation of Inner Ear Vesicles and Mechanosensitive Hair Cells from Human Pluripotent Stem Cells Day ~12—Transition of BMP/SB-FGF/LDN Treated Aggregates to Floating Culture At approximately day 12, BMP/SB-FGF/LDN-treated cell aggregates, as described in Example 4, are transferred to N2 Medium or N2 Medium containing 1-2% MATRIGEL™ (a gelatinous protein mixture secreted by Engelbreth-Holm-Swarm (EHS) mouse sarcoma cells) (or laminin and entactin) for extended culture. Half of the medium is changed every other day to maintain the health of the aggregates. In some cases, 3 μM CHIR99021 is included for 1-2 days to enhance the production of otic cells, defined by PAX2/8 and ECAD expression. Additionally, the addition of a Shh agonist to the medium for an extended period of time may induce proliferation and increase the yield of otic cells.

Days 12-20—Inner Ear Vesicle Formation

While in floating culture, vesicles containing PAX2/8 and ECAD+ cells will develop in each aggregate. These vesicles may also expresses markers of prosensory inner ear cells such as JAG1, SOX2, and/or MYO7A, which are checked by immunocytochemistry. Additionally, vesicles may express CYCLIN-D1.

Days 25-120—Generation of Hair Cells and Supporting Cells

Between days 25-120, hair cells are produced in prosensory vesicles following approximately 30-50 days of culture. Hair cells are identified by strong MYO7A expression, BRN3C, and ATOH1 expression. Hair cells also have F-ACTIN/ESPIN+ stereocilia bundles protruding from their apical ends into the lumen of the vesicle. Each hair cell also has an ACETYLATED-TUBULIN+ kinocilium associated with each stereocilia bundle. Supporting cells are distinguished by PROX1, CYCLIN-D1, P27 and/or CD326 expression.

REFERENCES

1. Bermingham-McDonogh, O. & Reh, T. A. Regulated Reprogramming in the Regeneration of Sensory Receptor Cells. *Neuron* 71, 389-405 (2011).
2. Brigande, J. V. & Heller, S. Quo vadis, hair cell regeneration? *Nat Neurosci* 12, 679-685 (2009).
3. Ouji, Y., Ishizaka, S., Nakamura-Uchiyama, F. & Yoshikawa, M. In vitro differentiation of mouse embryonic stem cells into inner ear hair cell-like cells using stromal cell conditioned medium. *Cell Death Dis* 3, e314 (2012).
4. Oshima, K. et al. Mechanosensitive Hair Cell-like Cells from Embryonic and Induced Pluripotent Stem Cells. *Cell* 141, 704-716 (2010).
5. Kondo, T. et al. Tlx3 exerts context-dependent transcriptional regulation and promotes neuronal differentiation from embryonic stem cells. *Proc Natl Acad Sci USA* 105, 5780-5785 (2008).
6. Reyes, J. H. et al. Glutamatergic neuronal differentiation of mouse embryonic stem cells after transient expression of neurogenin 1 and treatment with BDNF and GDNF: in vitro and in vivo studies. *J Neurosci* 28, 12622-12631 (2008).
7. Chen, W. et al. Restoration of auditory evoked responses by human ES-cell-derived otic progenitors. *Nature* 490, 278-282 (2012).
8. Schlosser, G. Induction and specification of cranial placodes. *Dev Biol* 294, 303-351 (2006).
9. Pieper, M., Ahrens, K., Rink, E., Peter, A. & Schlosser, G. Differential distribution of competence for panplacodal and neural crest induction to non-neural and neural ectoderm. *Development* 139, 1175-1187 (2012).
10. Groves, A. K. & Fekete, D. M. Shaping sound in space: the regulation of inner ear patterning. *Development* 139, 245-257 (2011).
11. Grocott, T., Tambalo, M. & Streit, A. The peripheral sensory nervous system in the vertebrate head: A gene regulatory perspective. *Dev Biol* 370, 3-23 (2012).
12. Eiraku, M. et al. Self-organizing optic-cup morphogenesis in three-dimensional culture. *Nature* 472, 51-56 (2011).
13. Suga, H. et al. Self-formation of functional adenohypophysis in three-dimensional culture. *Nature* 480, 57-62 (2011).
14. Eiraku, M. et al. Self-organized formation of polarized cortical tissues from ESCs and its active manipulation by extrinsic signals. *Cell Stem Cell* 3, 519-532 (2008).
15. Nakano, T. et al. Self-Formation of Optic Cups and Storable Stratified Neural Retina from Human ESCs. *Cell Stem Cell* 10, 771-785 (2012).
16. Kamiya, D. et al. Intrinsic transition of embryonic stem-cell differentiation into neural progenitors. *Nature* 470, 503-509 (2011).
17. Wilson, P. A. & Hemmati-Brivanlou, A. Induction of epidermis and inhibition of neural fate by Bmp-4. *Nature* 376, 331-333 (1995).
18. Bernardo, A. S. et al. BRACHYURY and CDX2 mediate BMP-induced differentiation of human and mouse pluripotent stem cells into embryonic and extraembryonic lineages. *Cell Stem Cell* 9, 144-155 (2011).
19. Chambers, S. M. et al. Highly efficient neural conversion of human ES and iPS cells by dual inhibition of SMAD signaling. *Nat Biotechnol* 27, 275-280 (2009).
20. Kwon, H.-J., Bhat, N., Sweet, E. M., Cornell, R. A. & Riley, B. B. Identification of early requirements for preplacodal ectoderm and sensory organ development. *PLoS Genet* 6, (2010).
21. Kwon, H.-J. & Riley, B. B. Mesendodermal signals required for otic induction: Bmp-antagonists cooperate with Fgf and can facilitate formation of ectopic otic tissue. *Dev Dyn* 238, 1582-1594 (2009).
22. Ladher, R. K., O'Neill, P. & Begbie, J. From shared lineage to distinct functions: the development of the inner ear and epibranchial placodes. *Development* 137, 1777-1785 (2010).
23. Li, A., Xue, J. & Peterson, E. H. Architecture of the mouse utricle: macular organization and hair bundle heights. *J Neurophysiol* 99, 718-733 (2008).
24. Meyers, J. R. et al. Lighting up the senses: FM1-43 loading of sensory cells through nonselective ion channels. *Journal of Neuroscience* 23, 4054-4065 (2003).
25. Géléoc, G. S. G., Risner, J. R. & Holt, J. R. Developmental Acquisition of Voltage-Dependent Conductances and Sensory Signaling in Hair Cells of the Embryonic Mouse Inner Ear.
26. Oesterle, E. C., Campbell, S., Taylor, R. R., Forge, A. & Hume, C. R. Sox2 and Jagged1 Expression in Normal and Drug-Damaged Adult Mouse Inner Ear. *J Assoc Res Otolaryngol* 9, 65-89 (2007).
27. Laine, H., Sulg, M., Kirjavainen, A. & Pirvola, U. Cell cycle regulation in the inner ear sensory epithelia: role of cyclin D1 and cyclin-dependent kinase inhibitors. *Dev Biol* 337, 134-146 (2010).
28. Warchol, M. E. & Richardson, G. P. Expression of the Pax2 transcription factor is associated with vestibular phenotype in the avian inner ear. *Dev Neurobiol* 69, 191-202 (2009).
29. Desai, S. S., Zeh, C. & Lysakowski, A. Comparative morphology of rodent vestibular periphery. I. Saccular and utricular maculae. *J Neurophysiol* 93, 251-266 (2005).
30. Lysakowski, A. et al. Molecular microdomains in a sensory terminal, the vestibular calyx ending. *Journal of Neuroscience* 31, 10101-10114 (2011).
31. Ying, Q.-L. et al. The ground state of embryonic stem cell self-renewal. *Nature* 453, 519 (2008).
32. Eiraku, M. & Sasai, Y. Mouse embryonic stem cell culture for generation of three-dimensional retinal and cortical tissues. *Nat Protoc* 7, 69-79 (2012).
33. Koehler, K. R. et al. Extended passaging increases the efficiency of neural differentiation from induced pluripotent stem cells. *BMC Neurosci* 12, 82 (2011).
34. Hama, H. et al. Scale: a chemical approach for fluorescence imaging and reconstruction of transparent mouse brain. *Nat Neurosci* 14, 1481-1488 (2011).
35. Jegalian, B. G. & De Robertis, E. M. Homeotic transformations in the mouse induced by overexpression of a human Hox3.3 transgene. *Cell* 71, 901-910 (1992).

36. Coate, T. M. et al. Otic Mesenchyme Cells Regulate Spiral Ganglion Axon Fasciculation through a Pou3f4/EphA4 Signaling Pathway. *Neuron* 73, 49-63 (2012).

37. Gale, J. E., Marcotti, W., Kennedy, H. J., Kros, C. J. & Richardson, G. P. FM1-43 dye behaves as a permeant blocker of the hair-cell mechanotransducer channel. *Journal of Neuroscience* 21, 7013-7025 (2001).

38. Hu, Z. & Corwin, J. T. Inner ear hair cells produced in vitro by a mesenchymal-to-epithelial transition.

What is claimed is:

1. A method for producing preplacodal ectoderm cells, the method comprising the steps of:
   (i) culturing pluripotent stem cells selected from the group consisting of human pluripotent stem cells and mouse pluripotent stem cells for between 1 to 2 days under conditions that result in formation of embryoid bodies from the cultured pluripotent stem cells;
   (ii) adding laminin and one or more extracellular matrix proteins selected from entactin, type IV collagen, fibronectin, vitronectin, and a gelatinous protein mixture secreted by Engelbreth-Holm-Swarm (EHS) mouse sarcoma cells to the cultured embryoid bodies formed in step (i);
   (iii) culturing the embryoid bodies of step (ii) for about 2 days to about 3 days in the presence of BMP2, BMP4, or BMP7 and a TGFβ inhibitor to form non-neural ectoderm; and
   (iv) culturing the non-neural ectoderm formed in (iii) for about 3 days to about 5 days in the absence of the BMP2, BMP4, or BMP7 and the TGFβ inhibitor, and in the presence of an exogenous FGF and a BMP inhibitor, in floating culture, to generate a cell population comprising preplacodal ectoderm cells, wherein human preplacodal ectoderm cells express one or more of SIX1/4, EYA1/2, IRX1/2/3, AP2, DLX3/5/6, GATA2/3, FOXI1/3 and E-cadherin or wherein mouse preplacodal ectoderm cells express at least one of Dlx3, Dlx5, Pax2, Pax8 and Eya1.

2. The method of claim 1, wherein step (iii) comprises culturing the embryoid bodies in the presence of BMP4.

3. The method of claim 1, wherein the pluripotent stem cells are human pluripotent stem cells.

4. The method of claim 3, wherein the BMP2, BMP4, or BMP7, and the TGFβ inhibitor are added to the cultured embryoid bodies on day 1 of culturing step (iii).

5. The method of claim 1, wherein the one or more extracellular matrix proteins are added to the cultured embryoid bodies on day 1 of culturing step (iii).

6. The method of claim 1, wherein the one or more extracellular matrix proteins comprise laminin or a gelatinous protein mixture secreted by Engelbreth-Holm-Swarm (EHS) mouse sarcoma cells.

7. The method of claim 6, wherein the one or more extracellular matrix proteins comprise entactin.

8. A method for producing otic placode cells, the method comprising the steps of:
(i) culturing pluripotent stem cells selected from the group consisting of human pluripotent stem cells and mouse pluripotent stem cells for between 1 to 2 days under conditions that result in formation of embryoid bodies from the cultured pluripotent stem cells;
(ii) adding laminin and one or more extracellular matrix proteins selected from entactin, type IV collagen, fibronectin, vitronectin, and a gelatinous protein mixture secreted by Engelbreth-Holm-Swarm (EHS) mouse sarcoma cells to the embryoid bodies formed in step (i);
(iii) culturing the embryoid bodies of step (ii) for about 2 days to about 3 days in the presence of BMP2, BMP4, or BMP7, and a TGFβ inhibitor to form non-neural ectoderm;
(iv) culturing the non-neural ectoderm formed in (iii) for about 3 days to about 5 days in the absence of a BMP and the TGFβ inhibitor, and in the presence of an exogenous FGF and a BMP inhibitor, in floating culture, to generate a cell population comprising preplacodal ectoderm cells, wherein human preplacodal ectoderm cells express one or more of SIX1/4, EYA1/2, IRX1/2/3, AP2, DLX3/5/6, GATA2/3, FOXI1/3 and E-cadherin, or wherein mouse preplacodal ectoderm cells express at least one of Dlx3, Dlx5, Pax2, Pax8 and Eya1; and
(v) culturing the preplacodal ectoderm cells formed in (iv), in floating culture, in the absence of the exogenous FGF and BMP inhibitor to obtain a cell population comprising otic placode cells, wherein human otic placode cells express one or more of Pax2, Pax8 and ECAD, or wherein mouse otic placode cells express one or more of Pax2, Pax8 and Sox2.

9. The method of claim 8, wherein the preplacodal ectoderm cells in the floating culture of (v) are cultured in the presence of an activator of Wnt/β-catenin signaling.

10. The method of claim 9, wherein the activator of Wnt/β-catenin signaling is a Gsk3 inhibitor.

11. The method of claim 8, wherein the exogenous FGF is any of FGF1-FGF23.

12. The method of claim 8, wherein the pluripotent stem cells are human pluripotent stem cells.

13. The method of claim 12, wherein the BMP2, BMP4, or BMP7 and the TGFβ inhibitor are added on day 1 of culturing step (iii), and the exogenous FGF and the BMP inhibitor are added on day 1 of culturing step (iv).

14. A method for producing inner ear sensory hair cells, the method comprising the steps of:
(i) culturing pluripotent stem cells selected from the group consisting of human pluripotent stem cells and mouse pluripotent stem cells for between 1 to 2 days under conditions that result in formation of embryoid bodies from the cultured pluripotent stem cells;
(ii) adding laminin and one or more extracellular matrix proteins selected from entactin, type IV collagen, fibronectin, vitronectin, and a gelatinous protein mixture secreted by Engelbreth-Holm-Swarm (EHS) mouse sarcoma cells to the embryoid bodies formed in step (i);
(iii) culturing the embryoid bodies of step (ii) for about 2 days to about 3 days in the presence of BMP2, BMP4, or BMP7 and a TGFβ inhibitor to form non-neural ectoderm;
(iv) culturing the non-neural ectoderm formed in (iii) for about 3 days to about 5 days in the absence of a BMP and the TGFβ inhibitor, and in the presence of an exogenous FGF and a BMP inhibitor, in floating culture, to generate preplacodal ectoderm, wherein human preplacodal ectoderm cells express one or more of SIX1/4, EYA1/2, IRX1/2/3, AP2, DLX3/5/6, GATA2/3, FOXI1/3 and E-cadherin, or wherein mouse preplacodal ectoderm cells express at least one of Dlx3, Dlx5, Pax2, Pax8 and Eya1;
(v) culturing the preplacodal ectoderm cells formed in (iv), in floating culture, in the absence of the exogenous FGF and BMP inhibitor to obtain otic placode cells; and
(vi) culturing the otic placode cells formed in (v) in floating culture in N2 medium comprising one or more extracellular matrix proteins for a time sufficient to form inner ear sensory hair cells, wherein human hair cells express MYO7A, BRN3C, and ATOH1, or wherein mouse hair cells express MYO7A.

15. The method of claim 14, wherein the exogenous FGF is FGF2.

16. The method of claim 14, further comprising culturing the preplacodal ectoderm in (v) in the presence of an activator of Wnt/β-catenin signaling.

17. The method of claim 16, wherein the activator of Wnt/β-catenin signaling is a Gsk3 inhibitor.

18. The method of claim 14, wherein the inner ear sensory hair cells comprise Type II vestibular hair cells.

19. The method of claim 14, wherein the pluripotent stem cells are human pluripotent stem cells.

* * * * *

UNITED STATES PATENT AND TRADEMARK OFFICE
CERTIFICATE OF CORRECTION

PATENT NO. : 10,308,911 B2
APPLICATION NO. : 15/446552
DATED : June 4, 2019
INVENTOR(S) : Eri Hashino et al.

Page 1 of 1

It is certified that error appears in the above-identified patent and that said Letters Patent is hereby corrected as shown below:

In the Specification

Column 25, Line 60, "MO" should be --M$\Omega$--.

Column 25, Line 66, "MO" should be --M$\Omega$--.

Column 27, Line 18, "(FIG. j)" should be --(FIG. 1i, j)--.

Column 28, Line 39, "Vila" should be --VIIa--.

Signed and Sealed this
Ninth Day of July, 2019

Andrei Iancu
*Director of the United States Patent and Trademark Office*